(12) United States Patent
Fussenegger et al.

(10) Patent No.: US 7,273,723 B2
(45) Date of Patent: Sep. 25, 2007

(54) ANTIBIOTIC-BASED GENE REGULATION SYSTEM

(76) Inventors: Martin Fussenegger, Bergacker 72, Zürich (CH) 8046; Wilfried Weber, Lachenacker 16, Zurich (CH) 8049

(\*) Notice: Subject to any disclaimer, the term of this patent is extended or adjusted under 35 U.S.C. 154(b) by 61 days.

(21) Appl. No.: 09/949,470

(22) Filed: Sep. 7, 2001

(65) Prior Publication Data
US 2004/0018490 A1 Jan. 29, 2004

(51) Int. Cl.
C12N 5/00 (2006.01)
C12N 5/02 (2006.01)
C12N 15/861 (2006.01)
C12N 15/00 (2006.01)
C12N 15/86 (2006.01)
C07H 21/04 (2006.01)

(52) U.S. Cl. ............... 435/69.1; 435/320.1; 435/455; 435/456; 435/41; 435/325; 536/24.1

(58) Field of Classification Search ............... 435/69.1, 435/6, 320.1, 325, 7, 455, 456, 41; 536/24.1; 530/351
See application file for complete search history.

(56) References Cited

U.S. PATENT DOCUMENTS

| | | | |
|---|---|---|---|
| 6,287,813 B1 | 9/2001 | Fussenegger et al. | |
| 6,509,152 B1* | 1/2003 | Berlin et al. | 435/6 |
| 2002/0102722 A1* | 8/2002 | Lo et al. | 435/320.1 |
| 2002/0155430 A1* | 10/2002 | Marsco et al. | 435/5 |
| 2002/0160514 A1* | 10/2002 | Goncz et al. | 435/455 |
| 2003/0206891 A1* | 11/2003 | Clackson et al. | 424/93.21 |

FOREIGN PATENT DOCUMENTS

WO     WO 00/65080     11/2000

OTHER PUBLICATIONS

Protein structure prediciton- Wikipedia, downloaded Oct. 14, 2005.*
Tertiary structures- Biology Pages, downloaded Oct. 14, 2005.*
Smith et al, Surface point mutations that significantly alter the structure and stability of a protein's denatured state, Protein Scinece, 1996, vol. 5, pp. 2009-2019.*
Houdebine LM. Transgenic animal bioreactors. Transgenic Res. 2000;9(4-5):305-20.*
Doetschman T. Interpretation of phenotype in genetically engineered mice.Lab Anim Sci. Apr. 1999;49(2):137-43.*
Noguchi et al. "Regulation of Transcription of the *mph*(A) Gene for Macrolide 2'-Phosphotransferase I in *Escherichia coli*: Characterization of the Regulatory Gene *mphR*(A)", Journal of Bacteriology, Sep. 2000, p. 5052-5058.
Fux et al. "Streptogramin- and tetracyline-responsive dual regulated expression p27$^{Kip1}$ sense and antisense enables positive and negative growth control of Chinese hamster ovary cells", Nucleic Acids Research , 2001, vol. 29, No. 4 e19, pp. 1-7.
Weber et al. "macrolide-based transgene control in mammalian cells and mice", Nature Biotechnology, Sep. 2002, vol. 20, pp. 901-907.
Norihasa et al. "Nucleotide Sequence and Characterization of Erythromycin Resistance Determinant That Enclodes Macrolide 2'—Phosphotransferase I in *Escherichia coli*", Antimicrobial Agents and Chemotherapy, Oct. 1995, pp. 2359-2363.
Macrina et al., "An International Journal Focusing on Gene cloning and Gene Structure and Function", Gene Elsevier Biomedical, Sep. 1982 vol. 19 No. 2, pp. 345-353.
"Everything You Need to Know About the Yeast Two-Hybrid System", www.nature.com, Aug. 2003, pp. 3-6.
Mendelsohn et al. "Applications of interaction traps/two hybrid systems to biotechnology research", www.xanadu.mgh.harvard.edu:/brentlabweb/andywb/m&b.html, Aug. 11, 2003.
Benson et al., 2006, "GenBank," *Nucleic Acids Research* (*Database issue*) 34:D16-20.
GenBank record for GenBank Accession No. AB038042, printed from NCBI website on Nov. 7, 2006.

\* cited by examiner

*Primary Examiner*—Joseph Woitach
*Assistant Examiner*—Maria Marvich
(74) *Attorney, Agent, or Firm*—Jones Day

(57) ABSTRACT

The invention relates to a novel system for gene regulation in eukaryotic cells, and methods of using the same for protein production, tissue engineering and gene therapy. In particular, the invention provides a new system for antibiotic-regulated gene expression in eukaryotic cells based on sequences from *Enterobacteriaceae* antibiotic resistance promoters, polypeptides that bind to the same in an antibiotic responsive manner, and nucleotides encoding such polypeptides. Further, the invention provides novel and sensitive methods of screening for candidate antibiotics.

42 Claims, 28 Drawing Sheets

Figure 4b

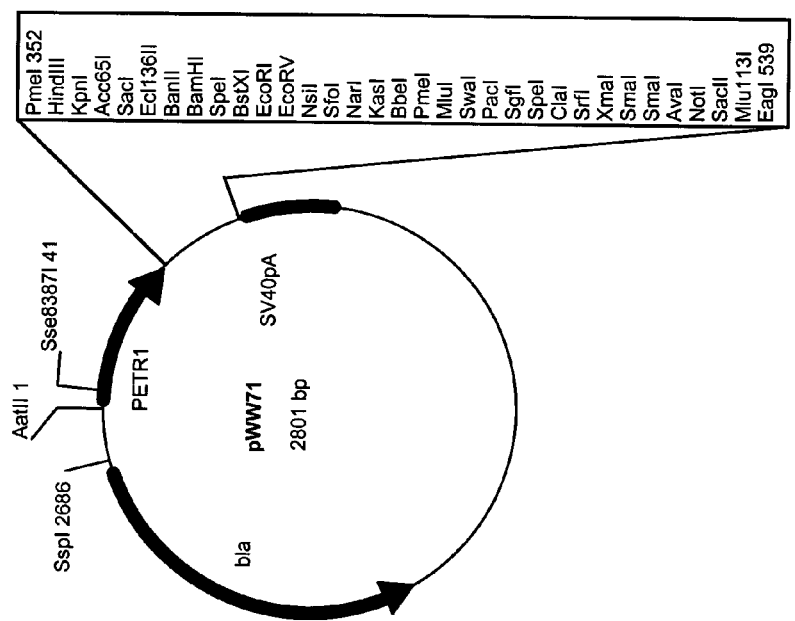
Figure 8a-a

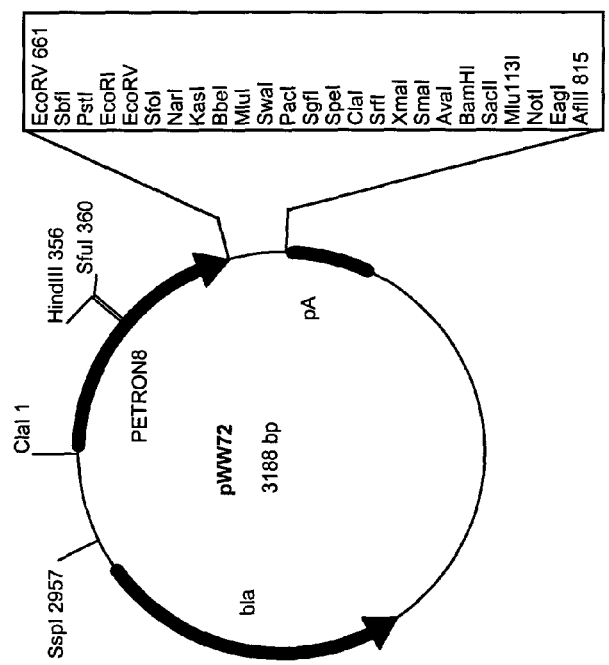
Figure 8a-b

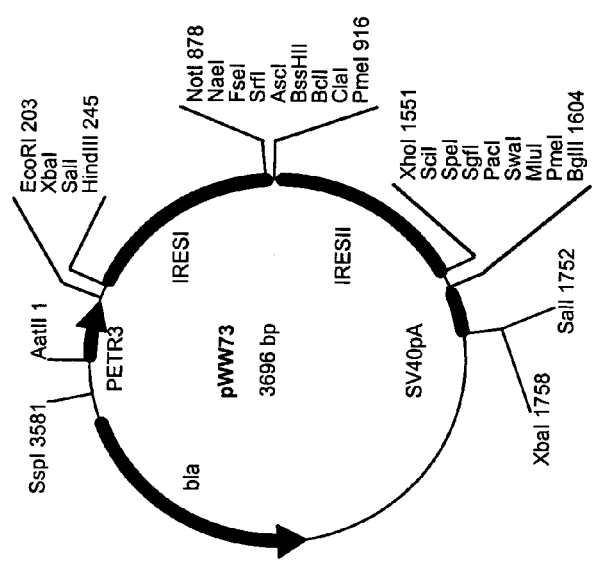
Figure 8b-a

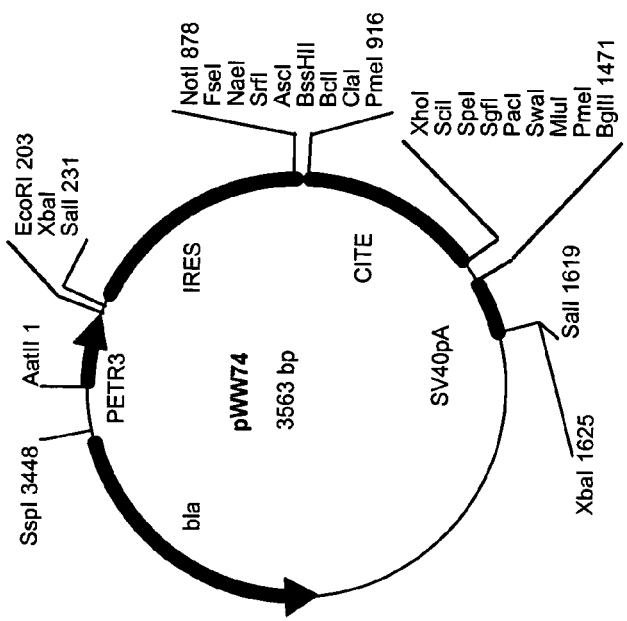
Figure 8b-b

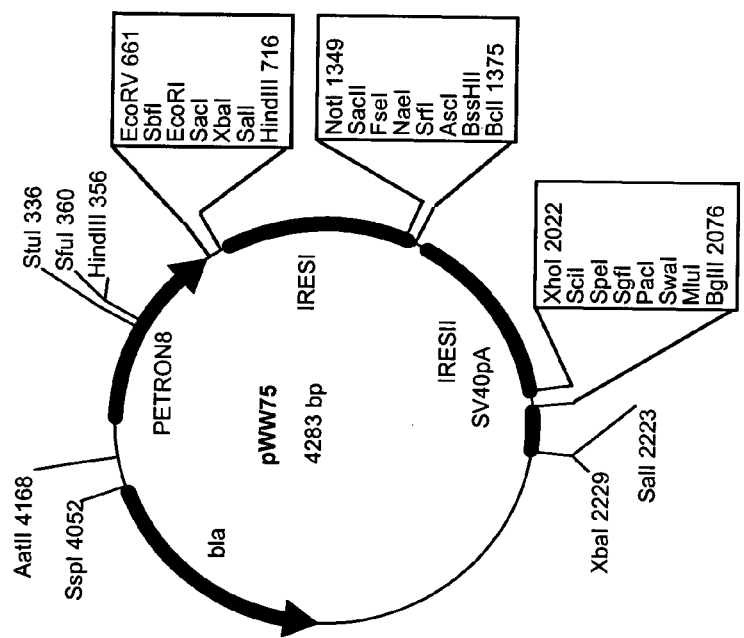
Figure 8b-c

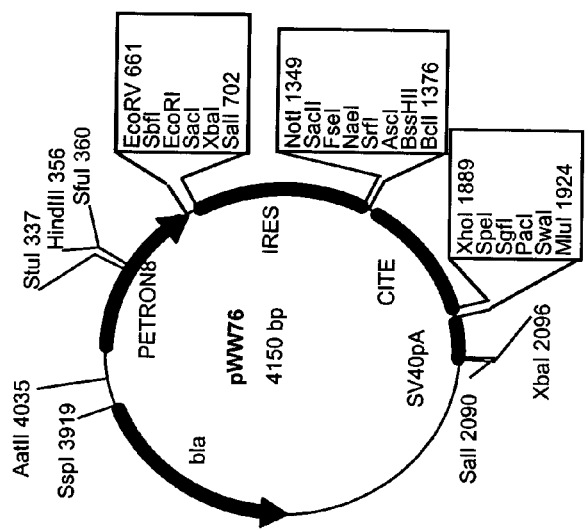
Figure 8b-d

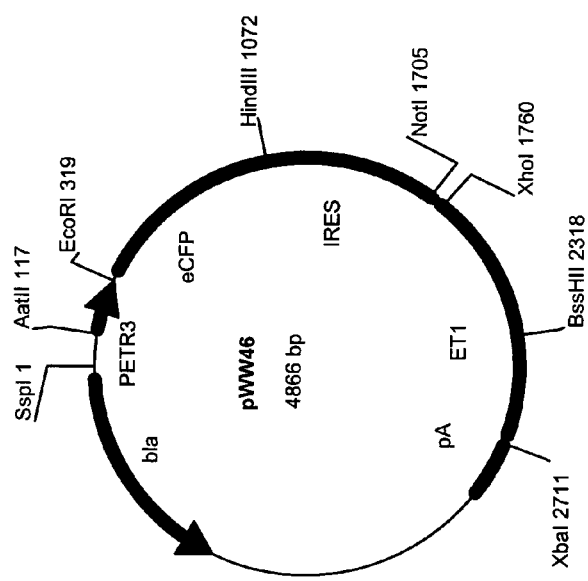
Figure 8c-a

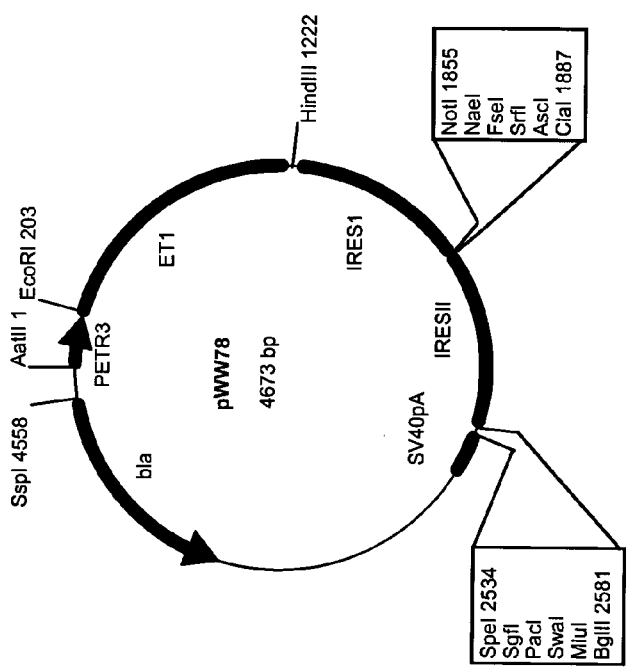
Figure 8c-b

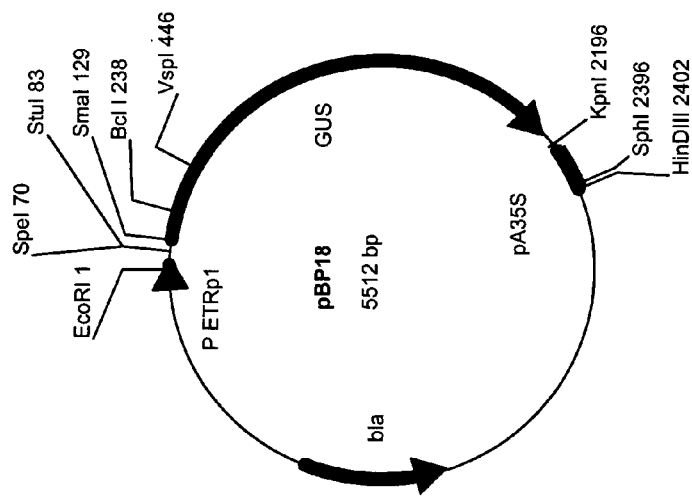
Figure 9b-a

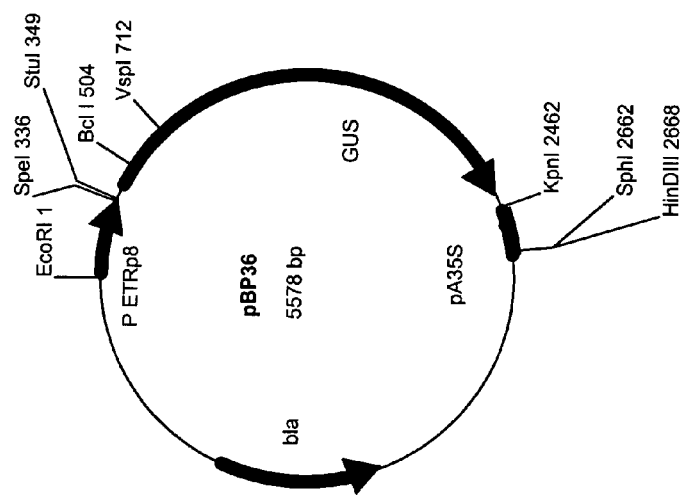
Figure 9b-b

SEQUENCE LISTING

```
<160> NUMBER OF SEQ ID NOS: 33

<210> SEQ ID NO 1
<211> LENGTH: 586
<212> TYPE: DNA
<213> ORGANISM: Shigella flexneri
<220> FEATURE:
<223> OTHER INFORMATION: Description of sequence: sequence fragment
      comprising nucleotides
      12452 through 13037

<400> SEQUENCE: 1
tttacgcatg tgcctggagg agttggaaat cgtcgtgttc gggaaacatt aaacacagga      60
tggcagcgat ctgagccagc acatgatcag ctagctcacc atccggatcg acggcccact     120
gcatctgtcg cgccagcgat gaccgagtgc aggagcaact cagctgccgc aggagcacct     180
gggggcagtc gcttgcggat cccctccacc accgcgcggt tccgctggat cgcaagcgtg     240
cgtagctccg gcacctggag ctcgtaccag gagatgagat agttcaccga gaagtcgttg     300
cgagtgttca tgctccgaac gagcacctgc aaaaattccc agagcccttg cggccctgcg     360
```

```
cctatcggta tcgcattcag gtaatgccgc acctgctcga cgccgcgctc catcatcctc    420
accagcagcg tatcgcggtt ggtgaagcgc tggattaacg ctgcgcggga gagcccacc     480 tcctttgcta ctccgctgag cgtgaactct atgggaccgc aacgcttcag cactacggtg    540
gcggcctcga gtacctcgtc atcggacttg agcttggggc ggggca                   586
```

<210> SEQ ID NO 2
<211> LENGTH: 35
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 2

```
gtacgaattc ccaccatgcc ccgccccaag ctcaa                               35
```

<210> SEQ ID NO 3
<211> LENGTH: 43
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 3

```
gcgcgcggct gtacgcggac gcatgtgcct ggaggagttg gaa                      43
```

<210> SEQ ID NO 4
<211> LENGTH: 616
<212> TYPE: DNA
<213> ORGANISM: Artificial Sequence
<220> FEATURE:
<223> OTHER INFORMATION: Description of artificial sequence:
      MphR(A)-containing EcoRI/BssHII
      fragment of pWW29

<400> SEQUENCE: 4

```
gtacgaattc ccaccatgcc ccgccccaag ctcaagtccg atgacgaggt actcgaggcc    60
gccaccgtag tgctgaagcg ttgcggtccc atagagttca cgctcagcgg agtagcaaag    120 gaggtgggggc tctcccgcgc agcgttaatc cagcgcttca ccaaccgcga tacgctgctg   180
gtgaggatga tggagcgcgg cgtcgagcag gtgcggcatt acctgaatgc gataccgata    240
ggcgcagggc cgcaagggct ctgggaattt ttgcaggtgc tcgttcggag catgaacact    300
cgcaacgact tctcggtgaa ctatctcatc tcctggtacg agctccaggt gccggagcta    360
cgcacgcttg cgatccagcg gaaccgcgcg gtggtggagg ggatccgcaa gcgactgccc    420
ccaggtgctc ctgcggcagc tgagttgctc ctgcactcgg tcatcgctgg cgcgacgatg    480
cagtgggccg tcgatccgga tggtgagcta gctgatcatg tgctggctca gatcgctgcc    540
atcctgtgtt taatgtttcc cgaacacgac gatttccaac tcctccaggc acatgcgtcc    600
gcgtacagcc gcgcgc                                                    616
```

<210> SEQ ID NO 5
<211> LENGTH: 972
<212> TYPE: DNA
<213> ORGANISM: Artificial Sequence
<220> FEATURE:
<223> OTHER INFORMATION: Description of artificial sequence:
      transactivator ET1

<400> SEQUENCE: 5

```
atgccccgcc ccaagctcaa gtccgatgac gaggtactcg aggccgccac cgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgatggag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgcccccagg tgctcctgcg     420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg     540
tttcccgaac acgacgattt ccaactcctc caggcacatg cgtccgcgta cagccgcgcg     600
cgtacgaaaa caattacgg gtctaccatc gagggcctgc tcgatctccc ggacgacgac     660
gcccccgaag aggcggggct ggcggctccg cgcctgtcct ttctccccgc gggacacacg     720
cgcagactgt cgacggcccc cccgaccgat gtcagcctgg gggacgagct ccacttagac     780
ggcgaggacg tggcgatggc gcatgccgac gcgctagacg atttcgatct ggacatgttg     840
ggggacgggg attccccggg tccgggattt accccccacg actccgcccc ctacggcgct     900
ctggatatgg ccgacttcga gtttgagcag atgtttaccg atgcccttgg aattgacgag     960
tacggtgggt ag                                                         972
```

```
<210> SEQ ID NO 6
<211> LENGTH: 1179
<212> TYPE: DNA
<213> ORGANISM: Artificial Sequence
<220> FEATURE:
<223> OTHER INFORMATION: Description of artificial sequence:
      transactivator ET2

<400> SEQUENCE: 6
```

```
atgccccgcc ccaagctcaa gtccgatgac gaggtactcg aggccgccac cgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgatggag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgcccccagg tgctcctgcg     420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg     540
tttcccgaac acgacgattt ccaactcctc caggcacatg cgtccgcgta cagccgcgcg     600
catgatgagt ttcccaccat ggtgtttcct tctgggcaga tcagccaggc ctcggccttg     660
gccccggccc ctccccaagt cctgccccag gctccagccc ctgccctgc tccagccatg     720 gtatcagctc tggcccaggc ccagcccct gtcccagtcc tagccccagg ccctcctcag     780
gctgtggccc cacctgcccc caagcccacc caggctgggg aaggaacgct gtcagaggcc     840
ctgctgcagc tgcagtttga tgatgaagac ctgggggcct tgcttggcaa cagcacagac     900
ccagctgtgt tcacagacct ggcatccgtc gacaactccg agtttcagca gctgctgaac     960
cagggcatac ctgtggcccc ccacacaact gagcccatgc tgatggagta ccctgaggct    1020
```

```
ataactcgcc tagtgacagg ggcccagagg ccccccgacc cagctcctgc tccactgggg      1080
gccccggggc tccccaatgg cctcctttca ggagatgaag acttctcctc cattgcggac      1140
atggacttct cagccctgct gagtcagatc agctcctaa                             1179
```

<210> SEQ ID NO 7
<211> LENGTH: 23
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 7

```
gcgcgcggcc actgcagtct tct                                              23
```

<210> SEQ ID NO 8
<211> LENGTH: 30
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 8

```
ggtctagagg atcctcagag gttgagaaca                                       30
```

<210> SEQ ID NO 9
<211> LENGTH: 942
<212> TYPE: DNA
<213> ORGANISM: Artificial Sequence
<220> FEATURE:
<223> OTHER INFORMATION: Description of artificial sequence:
      Transactivator ET3

<400> SEQUENCE: 9

```
atgccccgcc ccaagctcaa gtccgatgac gaggtactcg aggccgccac cgtagtgctg       60
aagcgttgcg gtcccataga gttcacgctc agcggagtag caaaggaggt ggggctctcc      120
cgcgcagcgt taatccagcg cttcaccaac cgcgatacgc tgctggtgag gatgatggag      180
cgcggcgtcg agcaggtgcg gcattacctg aatgcgatac cgataggcgc agggccgcaa      240
gggctctggg aattttttgca ggtgctcgtt cggagcatga acactcgcaa cgacttctcg      300
gtgaactatc tcatctcctg gtacgagctc caggtgccgg agctacgcac gcttgcgatc      360
cagcggaacc gcgcggtggt ggaggggatc cgcaagcgac tgcccccagg tgctcctgcg      420
gcagctgagt tgctcctgca ctcggtcatc gctggcgcga cgatgcagtg ggccgtcgat      480
ccggatggtg agctagctga tcatgtgctg gctcagatcg ctgccatcct gtgtttaatg      540
tttcccgaac acgacgattt ccaactcctc caggcacatg cgtccgcgta cagccgcgcg      600
cggccactgc agtcttctgc cctgctggac agcagcagca gcagcagcag cagcagcagc      660
agcagcagca acagtaacag cagcagttcg tccggaccca acccttctac ctcctttgag      720
cccatcaagg cagaccccac aggtgttttg gaactcccca aagagctgtc agaaatcttt      780
gatcccacac gagagtgcat gagctcggag ctgctggagg agttgatgtc ctcagaagtg      840
tttgcccctc tgcttcgtct ttctccaccc ccggggagacc acgattatat ctacaacctg      900
gacgagagtg aaggtgtctg tgtgcctgtt ctcaaccctct ga                        942
```

<210> SEQ ID NO 10
<211> LENGTH: 1044
<212> TYPE: DNA

<210> ORGANISM: Artificial Sequence
<220> FEATURE:
<223> OTHER INFORMATION: Description of artificial sequence:
      transrepressor ET4

<400> SEQUENCE: 10

```
atgccccgcc ccaagctcaa gtccgatgac gaggtactcg aggccgccac cgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgatggag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg     300
gtgaactatc tcatctcctg gtacgagctc caggtgccgg agctacgcac gcttgcgatc     360
cagcggaacc gcgcggtggt ggaggggatc cgcaagcgac tgccccagg tgctcctgcg      420
gcagctgagt tgctcctgca ctcggtcatc gctggcgcga cgatgcagtg ggccgtcgat     480
ccggatggtg agctagctga tcatgtgctg gctcagatcg ctgccatcct gtgtttaatg    540
tttcccgaac acgacgattt ccaactcctc caggcacatg cgtccgcgta cagccgcgcg    600
ccagatccaa aaagaagag aaggtagat ccaaaaaaga agagaaaggt agatccaaaa        660
aagaagagaa aggtaatgga tgctaagtca ctaactgcct ggtcccggac actggtgacc     720
ttcaaggatg tatttgtgga cttcaccagg gaggagtgga agctgctgga cactgctcag     780
cagatcgtgt acagaaatgt gatgctggag aactataaga acctggtttc cttgggttat     840
cagcttacta agccagatgt gatcctccgg ttggagaagg agaagagcc ctggctggtg       900
gagagagaaa ttcaccaaga gacccatcct gattcagaga ctgcatttga aatcaaatca     960
tcagtttcca gcaggagcat tttaaagat aagcaatcct gtgacattaa aatggaagga    1020
atggcaagga atgatctctg gtaa                                             1044
```

<210> SEQ ID NO 11
<211> LENGTH: 31
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 11

```
gggacccgc atgtgcctgg aggagttgga a                                      31
```

<210> SEQ ID NO 12
<211> LENGTH: 714
<212> TYPE: DNA
<213> ORGANISM: Artificial Sequence
<220> FEATURE:
<223> OTHER INFORMATION: Description of artificial sequence:
      transactivator ET5

<400> SEQUENCE: 12

```
atgccccgcc ccaagctcaa gtccgatgac gaggtactcg aggccgccac cgtagtgctg      60
aagcgttgcg gtcccataga gttcacgctc agcggagtag caaaggaggt ggggctctcc     120
cgcgcagcgt taatccagcg cttcaccaac cgcgatacgc tgctggtgag gatgatggag     180
cgcggcgtcg agcaggtgcg gcattacctg aatgcgatac cgataggcgc agggccgcaa     240
gggctctggg aattttttgca ggtgctcgtt cggagcatga acactcgcaa cgacttctcg    300
gtgaactatc tcatctcctg gtacgagctc caggtgccgg agctacgcac gcttgcgatc     360
```

```
cagcggaacc gcgcggtggt ggaggggatc cgcaagcgac tgcccccagg tgctcctgcg    420
gcagctgagt tgctcctgca ctcggtcatc gctggcgcga cgatgcagtg ggccgtcgat    480
ccggatggtg agctagctga tcatgtgctg gctcagatcg ctgccatcct gtgtttaatg    540
tttcccgaac acgacgattt ccaactcctc caggcacatg cggggtcccc ggccgacgcc    600
ctggacgact tcgacctgga catgctgccg ccgacgccc tggacgactt cgacctggac    660
atgctgccgg ccgacgccct ggacgacttc gacctggaca tgctgccggg gtaa          714
```

<210> SEQ ID NO 13
<211> LENGTH: 678
<212> TYPE: DNA
<213> ORGANISM: Artificial Sequence
<220> FEATURE:
<223> OTHER INFORMATION: Description of artificial sequence:
      transactivator ET6

<400> SEQUENCE: 13

```
atgccccgcc ccaagctcaa gtccgatgac gaggtactcg aggccgccac cgtagtgctg     60
aagcgttgcg gtcccataga gttcacgctc agcggagtag caaggaggt ggggctctcc    120 cgcgcagcgt taatccagcg cttcaccaac cgcgatacgc tgctggtgag gatgatggag    180
cgcggcgtcg agcaggtgcg gcattacctg aatgcgatac cgataggcgc agggccgcaa    240
gggctctggg aattttttgca ggtgctcgtt cggagcatga acactcgcaa cgacttctcg    300
gtgaactatc tcatctcctg gtacgagctc caggtgccgg agctacgcac gcttgcgatc    360
cagcggaacc gcgcggtggt ggaggggatc cgcaagcgac tgcccccagg tgctcctgcg    420
gcagctgagt tgctcctgca ctcggtcatc gctggcgcga cgatgcagtg ggccgtcgat    480
ccggatggtg agctagctga tcatgtgctg gctcagatcg ctgccatcct gtgtttaatg    540
tttcccgaac acgacgattt ccaactcctc caggcacatg cggggtcccc ggccgacgcc    600
ctggacgact cgacctgga catgctgcct gctgatgctc tcgatgattt cgatctcgat    660
atgctcccgg gtaactaa                                                   678
```

<210> SEQ ID NO 14
<211> LENGTH: 717
<212> TYPE: DNA
<213> ORGANISM: Artificial Sequence
<220> FEATURE:
<223> OTHER INFORMATION: Description of artificial sequence:
      transactivator ET7

<400> SEQUENCE: 14

```
atgccccgcc ccaagctcaa gtccgatgac gaggtactcg aggccgccac cgtagtgctg     60
aagcgttgcg gtcccataga gttcacgctc agcggagtag caaggaggt ggggctctcc    120 cgcgcagcgt taatccagcg cttcaccaac cgcgatacgc tgctggtgag gatgatggag    180
cgcggcgtcg agcaggtgcg gcattacctg aatgcgatac cgataggcgc agggccgcaa    240
gggctctggg aattttttgca ggtgctcgtt cggagcatga acactcgcaa cgacttctcg    300
gtgaactatc tcatctcctg gtacgagctc caggtgccgg agctacgcac gcttgcgatc    360
cagcggaacc gcgcggtggt ggaggggatc cgcaagcgac tgcccccagg tgctcctgcg    420
gcagctgagt tgctcctgca ctcggtcatc gctggcgcga cgatgcagtg ggccgtcgat    480
ccggatggtg agctagctga tcatgtgctg gctcagatcg ctgccatcct gtgtttaatg    540
tttcccgaac acgacgattt ccaactcctc caggcacatg cggggtcccc ggccgacgcc    600
ctggacgacg gcgacctgga catgctgcct gctgatgctc tcgatgattt cgatctcgat    660
```

```
atgctcccgg ccgacgccct ggacgactac gacctggaca tcctcccggg taactaa      717
```

```
<210> SEQ ID NO 15
<211> LENGTH: 78
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 15
gatcgacgtc gattgaatat aaccgacgtg actgttacat ttagggtaca cctgcaggtc   60
gagctcggta cccgggtc                                                 78

<210> SEQ ID NO 16
<211> LENGTH: 27
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 16
gctagaattc cgcggaggct ggatcgg                                       27

<210> SEQ ID NO 17
<211> LENGTH: 208
<212> TYPE: DNA
<213> ORGANISM: Artificial Sequence
<220> FEATURE:
<223> OTHER INFORMATION: Description of artificial sequence:
      erythromycin regulatable promoter
      Petr3

<400> SEQUENCE: 17
gacgtcgatt gaatataacc gacgtgactg ttacatttag ggtacacctg caggtcgagc   60
tcggtacccg gtcgagtag gcgtgtacgg tgggaggcct atataagcag agctcgttta   120
gtgaaccgtc agatcgcctg gagacgccat ccacgctgtt ttgacctcca tagaagacac  180
cgggaccgat ccagcctccg cggaattc                                     208

<210> SEQ ID NO 18
<211> LENGTH: 72
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 18
gatcgacgtc gattgaatat aaccgacgtg actgttacat ttaggcctgc agggagtacc   60
ctcgaccgcc gg                                                       72

<210> SEQ ID NO 19
<211> LENGTH: 107
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 19
gatcgacgtc gattgaatat aaccgacgtg actgttacat ttaggattg aatataaccg    60
```
acgtgactgt tacatttagg cctgcaggga gtaccctcga ccgccgg        107

<210> SEQ ID NO 20
<211> LENGTH: 73
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 20
gatcgacgtc gattgaatat aaccgacgtg actgttacat ttaggcctgc aggtcgagct   60
cggtacccgg gtc                                                     73

<210> SEQ ID NO 21
<211> LENGTH: 31
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 21
gcctgcagga ttcgagctcg gtacccgggt c                                 31

<210> SEQ ID NO 22
<211> LENGTH: 33
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 22
gcctgcagga tcgtcgagct cggtacccgg gtc                               33

<210> SEQ ID NO 23
<211> LENGTH: 35
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 23
gcctgcagga tcgtatcgag ctcggtaccc gggtc                             35

<210> SEQ ID NO 24
<211> LENGTH: 37
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 24
gcctgcagga tcgtaattcg agctcggtac ccgggtc                           37

<210> SEQ ID NO 25
<211> LENGTH: 39
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 25

```
gcctgcagga tcgtaatcgt cgagctcggt acccgggtc                                39
```

<210> SEQ ID NO 26
<211> LENGTH: 179
<212> TYPE: DNA
<213> ORGANISM: Artificial Sequence
<220> FEATURE:
<223> OTHER INFORMATION: Description of artificial sequence:
      independent operator sequence

<400> SEQUENCE: 26

```
gacgtcttcg aagtttaaac gattgaatat aaccgacgtg actgttacat ttagggattg         60
aatataaccg acgtgactgt tacatttagg gattgaatat aaccgacgtg actgttacat        120
ttagggattg aatataaccg acgtgactgt tacatttagg gatatcctgc agggaattc         179
```

<210> SEQ ID NO 27
<211> LENGTH: 287
<212> TYPE: DNA
<213> ORGANISM: Artificial Sequence
<220> FEATURE:
<223> OTHER INFORMATION: Description of artificial sequence:
      independent operator sequence

<400> SEQUENCE: 27

```
gattgaatat aaccgacgtg actgttacat ttagggattg aatataaccg acgtgactgt         60
tacatttagg gattgaatat aaccgacgtg actgttacat ttagggattg aatataaccg        120
acgtgactgt tacatttagg gataaacgat tgaatataac cgacgtgact gttacattta        180
gggattgaat ataaccgacg tgactgttac atttagggat tgaatataac cgacgtgact        240
gttacattta gggattgaat ataaccgacg tgactgttac atttagg                     287
```

<210> SEQ ID NO 28
<211> LENGTH: 70
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 28

```
gcgaattcga ttgaatataa ccgacgtgac tgttacattt agggttaaca ttcgagctcg         60
gtacaactcc                                                               70
```

<210> SEQ ID NO 29
<211> LENGTH: 22
<212> TYPE: DNA
<213> ORGANISM: Artificial Sequence
<220> FEATURE:
<223> OTHER INFORMATION: Description of artificial sequence:
      amplification oligonucleotide

<400> SEQUENCE: 29

```
tccaaggttg agcagaacct ac                                                 22
```

<210> SEQ ID NO 30
<211> LENGTH: 4070
<212> TYPE: DNA
<213> ORGANISM: Escherichia coli

<400> SEQUENCE: 30

```
ctgcaggaga tgctggctga acgcggagtg aatgtcgatc actccacgat ttaccgctgg         60
```

```
gttcagcgtt atgcgcctga aatggaaaaa cggctgcgct ggtactggcg taacccttcc      120
gatctttgcc cgtggcacat ggatgaaacc tacgtgaagg tcaatggccg ctgggcgtat      180
ctgtaccggg ccgtcgacag ccggggccgc actgtcgatt tttatctctc ctcccgtcgt      240
aacagcaaag ctgcataccg gtttctgggt aaaatcctca acaacgtgaa gaagtggcag      300
atcccgcgat tcatcaacac ggataaagcg cccgcctatg gtcgcgcgct tgctctgctc      360
aaacgcgaag gccggtgccc gtctgacgtt gaacaccgac agattaagta ccggaacaac      420
gtgattgaat gcgatcatgg caaactgaaa cggataatcg cgccacgct gggatttaaa       480 tccatgaaga cggcttacgc caccatcaaa ggtattgagg tgatgcgtgc actacgcaaa      540
ggccaggcct cagcatttta ttatggtgat cccctgggcg aaatgcgcct ggtaagcaga      600 gttttgaaa tgtaaggcct ttgaataaga caaaaggctg cctcatcgct aactttgcaa       660
cagtgccgga ttgaatataa ccgacgtgac tgttacattt aggtggctaa acccgtcaag      720
ccctcaggag tgaatcatga ccgtagtcac gaccgccgat acctcccaac tgtacgcact      780
tgcagcccga catgggctca agctccatgg cccgctgact gtcaatgagc ttgggctcga      840
ctataggatc gtgatcgcca ccgtcgacga tggacgtcgg tgggtgctgc gcatcccgcg      900
ccgagccgag gtaagcgcga aggtcgaacc agaggcgcgg gtgctggcaa tgctcaagaa      960
tcgcctgccg ttcgcggtgc cggactggcg cgtggccaac gccgagctcg ttgcctatcc     1020
catgctcgaa gactcgactg cgatggtcat ccagcctggt tcgtccacgc ccgactgggt     1080
cgtgccgcag gactcggagg tcttcgcgga gagcttcgcg accgcgctcg ccgccctgca     1140
tgccgtcccc atttccgccg ccgtggatgc ggggatgctc atccgtacac cgacgcaggc     1200
ccgtcagaag gtggccgacg acgttgaccg cgtccgacgc gagttcgtgg tgaacgacaa     1260
gcgcctccac cggtggcagc gctggctcga cgacgattcg tcgtgccag atttctccgt      1320 ggtggtgcat ggcgatctct acgtgggcca tgtgctcatc gacaacacgg agcgcgtcag     1380
cgggatgatc gactggagcg aggcccgcgt tgatgaccct gccatcgaca tggccgcgca     1440
ccttatggtc tttggtgaag aggggctcgc gaagctcctc ctcacgtatg aagcggccgg     1500
tggccgggtg tggccgcggc tcgcccacca catcgcggag cgccttgcgt tcggggcggt     1560
cacctacgca ctcttcgccc tcgactcggg taacgaagag tacctcgctg cggcgaaggc     1620
gcagctcgcc gcagcggaat gagcgaacgt cgatatagcc cgctcgcgac gctgttcgcg     1680
gcgacctttc tcttccggat cggcaacgcg gtggcggccc tcgcgcttcc atggttcgtc     1740
ctgtctcata caaagagcgc ggcctgggcg gcgccacgg ccgctagcag cgtcatcgcg      1800
accatcatcg gcgcgtgggt tggtggtggc ctcgtcgatc ggttcgggcg cgcgcccgtc     1860
gcattgatct cgggtgtggt gggcggcgtg gccatggcga gcatcccact gctcgatgcc     1920
gttggcgccc tctcgaacac tgggctgatc gcttgcgtgg tgctcggtgc gcgttcgac      1980 gcacccgta tggccgcgca ggacagtgag ctgcccaaac tcgccacgt cgccgggctc       2040 tccgttgagc gcgtctcgtc actgaaagcg gtgatcggga acgtcgcgat tctaggtggc     2100
ccggcccttg gggggccgc aatcggcctg cttggcgctg cgccaacgct cgggctgacg      2160
gcgttctgct ccgtccttgc aggtctgctc ggcgcgtggg tgcttcccgc gcgtgccgct     2220
cggacgatga ccacgacggc gactctctcc atgcgcgccg cgtcgctttt ctctggagc      2280 gaacccctgc tgcgccctct ctttggtata gtgatgatct tcgtgggcat cgttggcgcc     2340
aacggcagcg tcatcatgcc tgcgctgttt gtagatgcag gacgcaagt agcagagctc      2400 gggctgttct cctcaatgat gggggctggt ggtctccttg gcattgccat tcatgcgtcg     2460
```

```
gtcggcgccc ggatatcagc gcagaactgg ctggcggtgg cattttgtgg ctctgcggtg     2520
ggctcgcttc tgctttcaca gttgccaggc gtgccggtgc tgatgttgtt gggcgcgctc     2580
gtgggactgc tgaccggctc agtctctccc attctcaacg ctgccatcta caaccgcacg     2640
ccgccagaac ttctcggccg ggtactcggc acggtctcgg cggtgatgct gtcagcctcg     2700
cccatggtta tgcttgcggc cggcgcgttt gtcgaccttg ctggtccgct ccctggcctc     2760
gttgtatcgg ccgtgtttgc ggggctcgtg gctctactct cgctccgtct tcaatttgct     2820
acaatggcgg cggcagccac agcctccgcc caacccata cagaaggtga acactgatgc      2880
cccgccccaa gctcaagtcc gatgacgagg tactcgaggc cgccaccgta gtgctgaagc     2940
gttgcggtcc catagagttc acgctcagcg gagtagcaaa ggaggtgggg ctctcccgcg     3000
cagcgttaat ccagcgcttc accaaccgcg atacgctgct ggtgaggatg atggagcgcg     3060
gcgtcgagca ggtgcggcat tacctgaatg cgataccgat aggcgcaggg ccgcaagggc     3120
tctgggaatt tttgcaggtg ctcgttcgga gcatgaacac tcgcaacgac ttctcggtga     3180
actatctcat ctcctggtac gagctccagg tgccggagct acgcacgctt gcgatccagc     3240
ggaaccgcgc ggtggtggag gggatccgca agcgactgcc cccaggtgct cctgcggcag     3300
ctgagttgct cctgcactcg gtcatcgctg gcgcgacgat gcagtgggcc gtcgatccgg     3360
atggtgagct agctgatcat gtgctggctc agatcgctgc catcctgtgt ttaatgtttc     3420
ccgaacacga cgatttccaa ctcctccagg cacatgcgta aacggaggtg tgcagagtcc     3480
ctgcggcagg cgacgaacac gaccgtcgtc gattagtacc ggtacggtcg gtggtatcga     3540
agtcttgatc accactcagg tctacggctt acaaatggtg accatcccga tacttgcgtc     3600
agagcaccgg gccgattctt tgacagtgaa tcactcccgt aaggttgtgc cggtgtgggt     3660
gtcccgggtc gagacgatac tccgccaatg cgcccagcaa acaacctggc catcgcaggt     3720
ggtggggagc ggtgtggcgg atgagttgga caagttggtg tagcagcacg agcacggcga     3780
gataacatcg caggagttcg acatgctcaa gagacagctg attgcgaatc gcgatgcaga     3840
ttcataaccc gattgcgggt tggcttcact ccaccatcac cgagcagact agcacggcgg     3900
gctctgttgc aaagattggc ggcagtcaga ggtaggctgt cgctctgcgc cgatcaggcg     3960
gctgctgcga aatggtggtt gagcatgccc atggcctccg tcagcgccga gggcccaatg     4020
ccaaaagctc tctccacaag gcgcacctcg cccctgatgc cgggctgcag                4070
```

<210> SEQ ID NO 31
<211> LENGTH: 35
<212> TYPE: DNA
<213> ORGANISM: Artificial Sequence
<220> FEATURE:
<223> OTHER INFORMATION: Description of artificial sequence: ETR
      Sequence

<400> SEQUENCE: 31
gattgaatat aaccgacgtg actgttacat ttagg                                 35

<210> SEQ ID NO 32
<211> LENGTH: 194
<212> TYPE: PRT
<213> ORGANISM: Artificial Sequence
<220> FEATURE:
<223> OTHER INFORMATION: Description of artificial sequence: Amplified
      Sequence of MphR(A)

<400> SEQUENCE: 32

```
Met Pro Arg Pro Lys Leu Lys Ser Asp Asp Glu Val Leu Glu Ala Ala
1               5                   10                  15

Thr Val Val Leu Lys Arg Cys Gly Pro Ile Glu Phe Thr Leu Ser Gly
                20                  25                  30

Val Ala Lys Glu Val Gly Leu Ser Arg Ala Ala Leu Ile Gln Arg Phe
            35                  40                  45

Thr Asn Arg Asp Thr Leu Leu Val Arg Met Met Glu Arg Gly Val Glu
        50                  55                  60

Gln Val Arg His Tyr Leu Asn Ala Ile Pro Ile Gly Ala Gly Pro Gln
65                  70                  75                  80

Gly Leu Trp Glu Phe Leu Gln Val Leu Val Arg Ser Met Asn Thr Arg
                85                  90                  95

Asn Asp Phe Ser Val Asn Tyr Leu Ile Ser Trp Tyr Glu Leu Gln Val
                100                 105                 110

Pro Glu Leu Arg Thr Leu Ala Ile Gln Arg Asn Arg Ala Val Val Glu
                115                 120                 125

Gly Ile Arg Lys Arg Leu Pro Pro Gly Ala Pro Ala Ala Ala Glu Leu
        130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
                165                 170                 175

Leu Cys Leu Met Phe Pro Glu His Asp Asp Phe Gln Leu Leu Gln Ala
                180                 185                 190

His Ala

<210> SEQ ID NO 33
<211> LENGTH: 27
<212> TYPE: PRT
<213> ORGANISM: Artificial Sequence
<220> FEATURE:
<223> OTHER INFORMATION: Description of Sequence:  Nuclear Localization
      Signal (NLS) Derived From The Plant Transcription Factor TGA1b

<400> SEQUENCE: 33

Pro Glu Lys Lys Arg Ala Arg Leu Val Arg Asn Arg Glu Ser Ala Gln
1               5                   10                  15

Leu Ser Arg Gln Arg Lys Lys Leu Glu Ser Thr
                20                  25
```

ANTIBIOTIC-BASED GENE REGULATION SYSTEM

FIELD OF THE INVENTION

The invention relates to a novel system for gene regulation in eukaryotic cells, and methods of using the same, for example, for protein production. In particular, the invention provides a new system for antibiotic-regulated gene expression in eukaryotic cells, including mammalian and plant cells, based on sequences from *Enterobacteriaceae* antibiotic resistance promoters, polypeptides that bind to the same in an antibiotic-responsive manner, and nucleotides encoding such polypeptides.

BACKGROUND OF THE INVENTION

Citation of any reference in this section or any section hereof is not to be construed as an admission that such reference is available as prior art to this invention.

Controlled expression of transgenes or of target endogenous genes is essential for success of many genetic therapies. Constitutive expression of transgenes has often resulted in down-regulation of effector systems and/or cellular toxicity in animal studies (see, e.g., Efrat et al., 1995, Proc. Natl. Acad. Sci. USA 92, 3576-3580).

The expression of endogenous eukaryotic genes is often regulated by, for example, metabolic, hormonal, or environmental signals. In order to mimic natural physiological expression patterns with transgenes, and to minimize interactions with human gene regulation signals, binary promoter/transactivator configurations of heterologous origin which respond to heterologous stimuli have been developed in recent years. However, many exogenous stimuli which modulate these artificial mammalian regulons have proven to be incompatible with human therapeutic use due to cytotoxicity or undesired side effects (Baim et al., 1991, Proc. Natl. Acad. Sci. USA 88, 5072-5076; Braselmann et al., 1993, Proc. Natl. Acad. Sci. USA 90, 1657-1661; No D. et al., 1996, Proc. Natl. Acad. Sci. USA 93, 3346-3351; Rivera et al., 1996, Nat. Medicine 2, 1028-1032; Suhr et al., 1998, Proc. Natl. Acad. Sci. USA 95, 7999-8004; Wang et al., 1994, Proc. Natl. Acad. Sci. USA 91, 8180-8184; Fussenegger et al., 2000, Nat. Biotech. 18, 1203-1208).

Two systems have had some success for regulation of expression of transgenes in mammalian cells. In particular, the streptogramin-regulated mammalian expression system and the tetracycline-regulated mammalian expression system have avoided some of the problems associated with previous efforts. Streptogramin-regulated systems and tetracycline-regulated systems are described in U.S. Pat. Nos. 5,888,981; 5,866,755; 5,789,156; 5,654,168; and 5,650,298; PCT application no. WO 00/65080, to name just a few examples. However, the tetracycline-regulated system can fail to achieve the desired regulatory effects like low leakyness under repressed conditions or maximum expression in the induced state.

Moreover, gene therapy strategies often require independent control of multiple different transgenes or sets of transgenes which are cotranscribed in a multicistronic configuration. For example, many tissue expansion and ex vivo gene therapy scenarios require a two-step process beginning with expression of growth-promoting genes to enable expansion of grafted tissues in culture, followed by induction of growth suppressors to prevent tumorigenic behavior of treated cells after reimplantation. Sustained proliferation control is also required for stem cell-based technologies currently evaluated for eventual cell and tissue replacement therapy, since stem cells are tumorigenic (Rossant et al., 1999, Nat. Biotechnol. 17, 23-24; Solter et al., 1999, Science 283, 1468-1470). A second, independent gene regulation system could be used in such cells for pharmacologic control of one or several secreted therapeutic proteins, such as insulin, to enable titration of circulating proteins into the therapeutic range or adapt expression to optimal daily dosing regimes.

There is, therefore, a need for new mammalian gene regulation systems that employ modern, therapeutically proven antibiotics as controlling agents, and which can be used in combination with the tetracycline and/or streptogramin regulation systems, with minimal interaction between either tetracycline control or streptogramin control, or both, and the new control modality. However, dual-regulated expression technology is not sufficient to enable construction of complex artificial regulatory networks and cascades required for more sophisticated multigene interventions in next-generation human therapies and biopharmaceutical manufacturing. A novel mammalian gene regulation system that is independent of the streptogramin and tetracycline-regulated systems is needed to enable the regulation of such complex networks and cascades.

SUMMARY OF THE INVENTION

Accordingly, the present invention provides new systems for antibiotic-regulated gene expression in eukaryotic cells. The systems can be used to regulate the expression of genes in eukaryotic cells, including mammalian cells with antibiotics such as erythromycin, clarithromycin, azithromycin, tylosin, roxithromycin, and oleandomycin. Advantageously, the systems can be used in conjunction with streptogramin-regulated systems and/or tetracycline-regulated systems for the regulation of multiple genes. In certain embodiments, the present invention provides antibiotic-regulated gene expression systems based on sequences from *Enterobacteriaceae* antibiotic resistance promoters, and polypeptides that bind to the same in an antibiotic responsive manner. The systems are generally responsive to a family of macrolide antibiotics including, for example, erythromycin, clarithromycin, azithromycin, tylosin, roxithromycin, and oleandomycin. The systems typically comprise a polynucleotide having an erythromycin-responsive ("ETR") operator sequence. According to the present invention, an ETR is any operator sequence that is responsive to macrolide antibiotics such as erythromycin, clarithromycin, azithromycin, tyolosin, roxithromycin and oleandomycin.

In one aspect, the invention provides a method for regulating expression of an ETR-linked gene in a eukaryotic cell. The ETR-linked gene can be any gene operably linked to an ETR. Exemplary ETRs include sequences derived from an *Enterobacteriaceae* antibiotic responsive operon, in particular from an antibiotic responsive operon which occurs in an *Escherichia coli* bacterium as well as in a transposon of *Shigella flexneri*, (see, e.g., Genbank accession No. AF188331, nucleotides 15245 to 15211, encoded on complementary strand). The method entails introducing into the cell a nucleic acid molecule encoding an erythromycin-dependent transactivator or transrepressor (ET). The ET can be an ETR-binding protein, or can comprise an ETR-binding protein operably linked to a polypeptide that activates or represses transcription in eukaryotic cells, thereby rendering the ETR-linked gene capable of regulation by an antibiotic that binds to the ETR-binding protein in the cell. Exemplary ETs include the repressor protein MphR(A) (Noguchi et al., 2000, J. Bacteriol. 182, 5052-5058; Genbank accession no. AB038042, both of which are hereby incorporated by reference in their entirety). One can modulate the level of the antibiotic in the cell to regulate expression of the ETR-linked gene.

In another aspect, the invention is directed to a fusion ET polypeptide, which binds to an ETR sequence in the absence of its cognate antibiotic. A fusion ET polypeptide of the invention comprises a first polypeptide that binds to an ETR sequence in the absence of its cognate antibiotic operatively linked to a second polypeptide that activates or represses transcription in eukaryotic cells. Fusion ET polypeptides can be used to activate or repress transcription from a desired nucleotide sequence that is operatively linked to an ETR sequence. The present invention also provides an isolated nucleic acid encoding a fusion ET polypeptide.

The invention also includes host cells that contain nucleic acids encoding the polypeptides and fusion polypeptides of the invention. Such host cells optionally contain a desired nucleotide sequence to be transcribed operatively linked to an ETR sequence. The nucleotide sequence to be transcribed can be endogenous or exogenous to the host cell. Suitable host cells include, for example, mammalian cells such as CHO-K1, BHK-21, HeLa, COS-7, HEK 293, HEK 293T, HT1080, PC12, MDCK, C2C12, Jurkat, NIH3T3, K-562, TF-1, P19 and human embryonic stem cells like clone H9 (Wicell, Madison, Wis., USA) or plant cells such as those derived from barley, wheat, rice, soybean, potato, arabidopsis and tobacco (e.g. *Nicotiana tabacum* SR1). Suitable hosts also include plant-derived hairy root cultures such as, for example, hairy root cultures derived from Artemisia, Atropa, Beta, Brugmansia, and others such as those described in Shanks and Morgan, 1999, Curr. Opin. Biotechnol. 10:151-155. Other suitable cell lines of mammalian and plant origin are well known to those of skill in the art and include, for example, those described in *ATCC Cell Lines and Hybridomas* $8^{th}$ *Edition,* 1994, American Type Culture Collection, Rockville, Md. The present invention also provides transgenic animals comprising the nucleic acids of the invention. Preferred transgenic animals include transgenic mice.

Yet another aspect of the invention provides an isolated nucleic acid having an ETR sequence operatively linked to a first eukaryotic promoter. The isolated nucleic acid can have one or more ETR sequences. For instance, the isolated nucleic acid can have 4, 8, 12 or more ETR sequences in tandem. The first eukaryotic promoter can also be operatively linked to a first coding sequence. Optionally, the nucleic acid can also contain at least one tetracycline-responsive operator sequence ("tet") and/or at least one pristinamycin-responsive-operator sequence ("pip") operatively linked to a second and/or third eukaryotic promoter, which in turn can be operatively linked to a second and/or third coding sequence. Either coding sequence can encode any protein of interest for which regulated expression is desired. In certain embodiments, at least one of the coding sequences can encode a tumor suppressor gene product or a gene product which activates or represses cell proliferation, differentiation or apoptosis. Still further, at least one of the promoters can be operatively linked to more than one coding sequence through the use of, for example, an internal ribosome entry site (IRES). Host cells genetically engineered to contain these nucleic acids are also provided by the invention. Another aspect of the invention provides vectors for ETR-regulated expression of a gene in a eukaryotic cell. Suitable vectors for ETR-regulated expression include mammalian expression vectors, plant expression vectors, retroviral expression vectors, adenoviral expression vectors, adeno-associated viral expression vectors, alphaviral expression vectors and lentiviral expression vectors and other vectors known to those of skill in the art.

Still another aspect of the invention is a process for producing a protein by culturing a eukaryotic cell containing an ETR-linked gene that encodes the protein and a nucleic acid molecule encoding an ET. The ET can be an ETR-binding protein, or can comprise an ETR-binding protein operably linked to a polypeptide that activates or represses transcription in eukaryotic cells. Expression of the ETR-linked gene is then regulated by modulating the level of an antibiotic that binds to the ETR-binding protein in the cell. Optionally, the process entails the step of collecting the protein produced by the cell.

Another aspect of the invention is a method of screening for candidate antibiotics and other substances with potential immunomodulatory activity. The method entails incubating the host cells of the invention, the host cells containing an ETR-linked reporter gene and a sequence encoding an ETR-binding protein, in the presence of a test compound, wherein a change in the transcription of the reporter gene indicates that the test compound is a candidate antibiotic or potential immunomodulatory substance.

Another aspect of the invention is a method for detection of macrolide antibiotics in samples of different origin such as food samples like milk, meat etc. The method entails incubating the host cells of the invention, the host cells containing an ETR-linked reporter gene and a sequence encoding an ETR-binding protein (ET) in the presence of a test sample, wherein a change in the transcription of the reporter gene indicates that the sample contains probably macrolide antibiotics or other substances modulating the binding activity of ET.

Another aspect of the invention is a method of screening for candidate antibiotics and other substances with potential immunomodulatory activity. The method entails the in-vitro binding analysis of an ETR-containing nucleic acid and an ETR-binding protein, wherein both binding partners can be fused to other compounds (such as reporter enzymes, dyes) in order to facilitate in vitro binding analysis. A change in the binding state of the ETR-containing nucleic acid and an ETR-binding protein indicates the presence of a candidate compound such as an antibiotic or an immunomodulatory substance.

The invention also relates to the construction of transgenic animals in which the expression of one or more genes can be controlled externally by the macrolide regulatory system. Such genes include human genes whose expression, failure of expression or other defects are involved in human diseases. Such transgenic animals can serve as models for human diseases in therapeutic studies and for the screening of compounds of pharmaceutical interest.

The invention also relates to a kit comprising a carrier means having in close confinement therein at least one container means such as tubes, vials, bottles and the like, which contains a polynucleotide molecule that can be used in the practice of the invention. The invention also relates to kits comprising prokaryotic or eukaryotic cells containing at least one polynucleotide molecule of the invention. The invention also relates to transgenic organisms, which incorporate in a stable or transient way a polynucleotide molecules of the invention.

BRIEF DESCRIPTION OF THE FIGURES

The patent or application file contains at least one drawing executed in color. Copies of this patent or patent application publication with color drawing(s) will be provided by the Office upon request and payment of necessary fee.

FIG. 4b: Multiregulated multigene expression by combination of an erythromycin-responsive system with the streptogramin-(PIP) and tetracycline-(TET) responsive expression systems. The cell line CHO-Triplet$_{42}$ containing ET1, the streptogramin-(PIT) and tetracycline-(tTA) dependent transactivators was transfected with $P_{ETR3}$-driven CFP expression unit and a dual-regulated expression vector encoding a Tet-responsive RFP (red fluorescent protein) and a PI-responsive YFP (yellow fluorescent protein) expression unit ($P_{hCMV*-1}$-RFP-pA$_I$-/-P$_{PIR}$-YFP-pA$_{II}$). 48 h following transfection, expression of CFP, YFP and RFP was assessed by fluorescence microscopy in cultures containing different combinations of erythromycin (EM, 2 μg/ml), pristinamycin I (PI; 2 μg/ml) or tetracycline (Tet; 2 μg/ml). In the absence of all antibiotics CFP, YFP and RFP are simultaneously expressed. Selective repression is achieved by addition of the respective antibiotics.

FIGS. 8a-a and 8a-b: Graphical representation of multipurpose expression vectors pWW71 (FIG. 8a-a) and pWW72 (FIG. 8a-b). pWW71 contains the macrolide-repressible promoter $P_{ETR1}$ followed by a large multiple cloning site for facilitated insertion of different transgenes. pWW72 encodes the macrolide-inducible promoter $P_{ETR}$ON8 followed by a large multiple cloning site.

FIGS. 8b-a, 8b-b, 8b-c and 8b-d: Graphical representation of tricistronic multi-purpose expression vectors pWW73 (FIG. 8b-a), pWW74 (FIG. 8b-b). pWW75 (FIG. 8b-c) and pWW76 (FIG. 8b-d) controlled by macrolide-responsive promoters. pWW73 (pTRIDENT20) and pWW74 (pTRIDENT21) allow macrolide-repressible expression ($P_{ETR3}$), whereas pWW75 (pTRIDENT 22) and pWW76 (pTRIDENT23) contain the macrolide inducible promoter $P_{ETR}$ON8. Whereas the first cistron of the tricistronic expression unit is transcribed in a cap-dependent manner, the subsequent genes rely on cap-independent translation initiation based on internal ribosome entry sites of polioviral (IRES) origin or of encephalomyocarditis virus. A polyadenylation site (pA) of the SV40 virus terminates the multicistronic expression unit.

FIGS. 8c-a and 8c-b: Graphical representation of autoregulated multi-purpose expression vectors: pWW46 expresses the cyan fluorescent protein (CFP) in a dicistronic unit together with the macrolide-repressible transactivator ET1 (FIG. 8c-a). This autoregulated setup allows compact genetic design for macrolide-regulated expression. The same concept applies to pWW78, an autoregulated, macrolide-repressible vector with two empty cistrons containing two large multiple cloning sites for insertion of various transgenes (FIG. 8c-b).

FIGS. 9b-a and 9b-b: Graphical representation of the erythromycin-repressible EP$_{OFF}$ plant expression vectors pBP18 (FIG. 9b-a) and pBP36 (FIG. 9b-b). pBP18 and pBP36 are β-glucuronidase (GUS) expression vectors which are driven by the macrolide-repressible promoters which contain one (ETR, pBP 18) or eight (ETR8, pBP36) copies of the ETR binding sequence fused to a PCaMV35S minimal promoter.

DETAILED DESCRIPTION OF THE INVENTION

Figure 1:
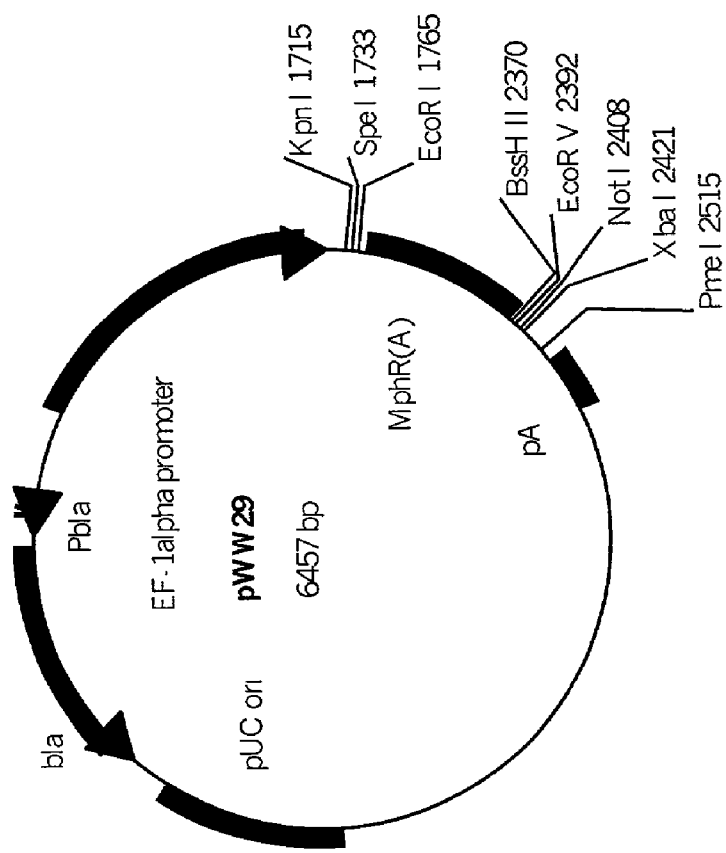
FIG. 1: Graphical representation of vector pWW29, which encodes an ETR binding protein under control of the elongation factor 1α promoter (Uetsuk et al., 1989. J. Biol. Chem. 264, 5791-5798).

The present invention is directed to new systems for antibiotic-regulated gene expression in eukaryotic cells based on sequences from macrolide antibiotic resistance promoters derived from *Enterobacteriaceae* and polypeptides that bind to the same in an antibiotic responsive manner. The systems of the present invention provide gene regulation in eukaryotic cells with antibiotics of the macrolide class such as erythromycin, clarithromycin, azithromycin, tylosin, roxithromycin and oleandomycin.

Erythromycin (EM), the prototype of macrolide antibiotics, has been successfully used for over half a century as broad-spectrum antibiotic against Gram-positive and a few Gram-negative human pathogenic bacteria including *Helicobacter, Bordetella* and *Legionella* spp. (Guay, 1996. Drugs 51, 515-536). Recently, a 14-member ring macrolide-inactivating 2'-phosphotransferase I (mph(A)) has been cloned from a transposon (Noguchi et at., 2000. FEMS Microb. Lett. 192: 175-178) of the clinical *E. coli* isolate Tf481A (Noguchi et al., 1995, Antimicrob Agents Chemother. 39, 2359-2363). mph(A) expression is regulated by a repressor protein MphR(A) (sequence disclosed in Noguchi et al., 2000. J. Bacteriol. 182, 5052-5058, Genbank accession no. AB038042) (SEQ ID NO: 30) which binds to a 35-bp erythromycin-responsive operator sequence overlapping the mph(A) promoter (Noguchi et al., 2000. J. Bacteriol. 182, 5052-5058). Binding of EM to MphR(A) disrupts the MphR (A)-ETR interaction and results in derepression of mph(A).

For purposes of the invention, an ETR sequence is a sequence from an *Enterobacteriaceae* macrolide antibiotic resistance promoter that binds a particular polypeptide, an erythromycin-dependent transactivator or transrepressor (also referred to herein as an "ET" or "a first polypeptide which binds to an ETR sequence in the absence of its cognate antibiotic"), in an antibiotic-dependent manner. The antibiotic resistance promoter can be derived from a chromosomal promoter but is preferably derived from a naturally-occurring episome. Preferably, the ET binds to the ETR sequence in the absence of its cognate antibiotic, and is released from the ETR sequence when antibiotic is present, although the reverse situation is also within the scope of the invention. Accordingly, in the presence of the ET, expression from the antibiotic resistance promoter containing the ETR sequence is regulated by the presence or absence of antibiotic. Thus, for purposes of the invention, the term "cognate antibiotic" means the antibiotic which when bound to the ET results in the release of the protein from its ETR binding site. Preferred antibiotics include those of the macrolide class such as erythromycin, clarithromycin, azithromycin, tylosin, roxithromycin and oleandomycin.

Preferred macrolide-dependent transactivators and transrepressors ("ETs") include MphR(A) (Noguchi et al., 2000, J. Bacteriol 182, 5052-5058) and related polypeptides. ETs can be, for the purposes of the invention, derived from or related to MphR(A) proteins produced by *Enterobacteriaceae*. By "derived from" MphR(A) proteins produced by *Enterobacteriaceae*, is meant, in this context, that the amino acid sequence is identical to a naturally occurring MphR(A), or contains only conservative amino substitutions and but remains at least 70%, preferably 80%, more preferably 90%, and most preferably 95% identical at the amino acid level. By "related to" MphR(A) proteins produced by *Enterobacteriaceae* is meant, for purposes of the invention, that the polynucleotide sequence that encodes the amino acid sequence hybridizes to a naturally occurring MphR(A) produced by *Enterobacteriaceae* under at least low stringency conditions, more preferably moderate stringency conditions, and most preferably high stringency conditions, and binds to an ETR recognition sequence. Conservative substitutions known in the art and described by Dayhof, M. D., 1978, Nat. Biomed. Res. Found., Washington, D.C., Vol. 5, Sup. 3, among others. Genetically encoded amino acids are generally divided into four groups: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. A substitution of one amino acid in a particular group with another amino acid in the same group is generally regarded as a conservative substitution.

The *Enterobacteriaceae* include bacteria from the following taxonomic groups: *Enterobacter, Escherichia, Klebsiella, Kluyvera, Pantoea, Salmonella, Shigella, Yersinia* and unclassified *Enterobacteriaceae* (see, e.g., references "*Enterobacteriaceae*" in Bergey's Manual Of Systematic Bacteriology, Vols. I to IV, 8t$^h$ edition", Williams and Williams, Baltimore, Md., 1984). Preferred *Enterobacteriaceae* include *Escherichia* and *Shigella*.

*Enterobacteriaceae* antibiotic-resistant promoters that contain ETR sequences can be identified by generating *Enterobacteriaceae* gene libraries in a heterologous host, and growing the heterologous host under conditions containing selective antibiotics. Emerging resistant clones containing antibiotic resistant determinants can be identified by their characteristic protein binding motifs following sequence analysis and are also included within the scope of this invention.

Polynucleotide sequences encoding an ET can be used to clone homologous ETs in other organisms. Thus, the invention also is directed to nucleic acids hybridizable to or complementary to ETs such as MphR(A) described herein. Such ETs are at least 50%, preferably 60%, more preferably 70%, even more preferably 80%, yet more preferably 90%, and most preferably 95% identical at the amino acid sequence level to MphR(A) described herein. Homology can be calculated using, for example, the BLAST computer program (Altschul et al., 1997, Nucleic Acids Res. 25:3389-

402). Typical parameters for determining the similarity of two sequences using BLAST 2.0 are a reward for match of 1, penalty for mismatch of −2, open gap and extension gap penalties of 5 and 2, respectively, a gap dropoff of 50, and a word size of 11.

In a specific embodiment, a nucleic acid, which is hybridizable to an nucleic acid encoding an ET such as a nucleic acid encoding MphR(A) under conditions of low stringency is provided. By way of example and not limitation, procedures using such conditions of low stringency are as follows (see also Shilo and Weinberg, 1981, Proc. Natl. Acad. Sci. USA 78:6789-6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency, which can be used are well known in the art (e.g., as employed for cross-species hybridizations).

In another specific embodiment, a nucleic acid, which is hybridizable to an ET-encoding nucleic acid, such as a MphR(A)-encoding nucleic acid under conditions of moderate stringency is provided. By way of example and not limitation, procedures using such conditions of moderate stringency are as follows: Filters containing DNA are pretreated for 6 h at 55° C. in a solution containing 6×SSC, 5× Denhart's solution, 0.5% SDS and 100 μg/ml denatured salmon sperm DNA. Hybridizations are carried out in the same solution and 5-20×10$^6$ cpm $^{32}$P-labeled probe is used. Filters are incubated in hybridization mixture for 18-20 h at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 h in a solution containing 2×SSC, 0.1% SDS.

In another specific embodiment, a nucleic acid which is hybridizable to an ET-encoding nucleic acid, such as a MphR(A)-encoding nucleic acid under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which can be used are well known in the art.

New ETs can also be isolated by binding to ETR sequences. For example, a polynucleotide comprising an ETR sequence can be immobilized on a matrix and ideally packed in a column. Bacterial or eukaryotic extracts can be applied to the column under conditions, which allow ETs to bind to the immobilized target sequence. Following appropriate washing steps, the ET can be eluted by suitable conditions (e.g., addition of antibiotic). The corresponding gene can be cloned, and the sequence of the purified protein can be determined.

ETs of the invention include polypeptides that bind to ETR sequences, as well as fusion proteins containing a first polypeptide that binds to ETR sequences operatively linked to a second polypeptide which activates or represses transcription in eukaryotic cells. In this context, operatively linked means that the two proteins are covalently or non-covalently bound to one another in such a manner that they retain their functional activities of binding to ETR sequence (first polypeptide) and activating or repressing transcription (second polypeptide).

The fusion proteins of the invention comprise the first polypeptide, which binds to an ETR sequence in the absence of its cognate antibiotic, and a second polypeptide which activates or represses transcription in eukaryotic cells. By activating transcription is meant that the rate of transcription is increased from the nucleotide sequence to be transcribed that is operatively linked to an ETR sequence when the fusion protein that activates transcription is bound to the ETR sequence, as opposed to when it is not bound. Similarly, by repression of transcription is meant that the rate of transcription is decreased from the nucleotide sequence to be transcribed that is operatively linked to an ETR sequence when the fusion protein that represses transcription is bound to the ETR sequence, as opposed to when it is not bound.

Accordingly, in one aspect, the first polypeptide of the fusion protein that activates transcription is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). The first and second polypeptides can be in any order. The second polypeptide of the transactivator can itself possess transcriptional activation activity (i.e., the second polypeptide directly activates transcription) or it can activate transcription by an indirect mechanism, through recruitment of transcriptional activation proteins to interact with the fusion protein. Accordingly, the term "a polypeptide which activates transcription in eukaryotic cells" includes polypeptides which either directly or indirectly activate transcription.

Polypeptides which can function to activate transcription in eukaryotic cells are well known in the art and are described, for example, in U.S. Pat. No. 5,654,168. Such polypeptides include the herpes simplex virus virion protein 16 (VP16, the amino acid sequence of which is disclosed in Triezenberg, S. J. et al., 1988, Genes Dev. 2:718-729), particularly the 127 amino acid C-terminus or the 11 amino acid C-terminus. Suitable C-terminal peptide portions of VP16 are described in Seipel, K. et al. (EMBO J., 1992, 11:4961-4968) and in Baron et al., Nucleic Acids Res. 1997, 25: 2723-2729. Another suitable polypeptide with activating potential on transcription in eukaryotic cells is the activating domain of E2F4 which is described in Akagi et al., Nucleic Acids Res. 2001, 29: e23.

Acidic transcription activation domains, proline-rich transcription activation domains, serine/threonine-rich transcription activation domains and glutamine-rich transcription activation domains can all be used in the compositions and methods of the invention. VP16 polypeptides and amino acid residues 753-881 of GAL4 are acidic activating domains. Another polypeptide that activates transcription is the p65 domain of NF-κB (Schmitz and Baeuerle, 1991, EMBO J. 10:3805-3817). Examples of proline-rich activation domains include amino acid residues 399-499 of CTF/NF1 and amino acid residues 31-76 of AP2. Examples of serine/threonine-rich transcription activation domains include amino acid residues 1-427 of ITF1 and amino acid residues 2-451 of ITF2. Examples of glutamine-rich activation domains include amino acid residues 175-269 of Oct1 and amino acid residues 132-243 of Sp1. The amino acid sequences of each of the above described regions, and of other useful transcriptional activation domains, are disclosed in Seipel, K. et al. (EMBO J., 1992, 11:4961-4968). This reference also describes methods of identifying new transcriptional activation domains which are within the scope of the invention.

In another embodiment, the second polypeptide of the fusion protein indirectly activates transcription by forming a non-covalent association with a transcriptional activator. For example, an ET of the invention can be fused to a polypeptide domain (e.g., a dimerization domain) capable of mediating a protein-protein interaction with a transcriptional activator protein, such as an endogenous activator present in a host cell. Non-covalent interactions between DNA binding domains and transactivation domains are known in the art (see e.g., Fields and Song, 1989, Nature 340:245-247; Chien et al, 1991, Proc. Natl. Acad. Sci. USA 88:9578-9582; Gyuris et al., 1993, Cell 75:791-803; and Zervos, A. S., 1993, Cell 72:223-232). Examples of suitable interaction (or dimerization) domains include leucine zippers (Landschulz et al., 1989, Science 243:1681-1688), helix-loop-helix domains (Murre, C. et al., 1989, Cell 58:537-544) and zinc finger domains (Frankel, A. D. et al., 1988, Science 240: 70-73; Beerli et al., J. Biol. Chem. 2000, 275: 32617-32627).

In another aspect, the polypeptide that binds ETR can be used by itself to repress transcription in the absence of antibiotic. In this manner, the polypeptide that binds ETR prevents transcription when bound to the ETR sequence, presumably by interfering with binding of activating transcription factors or by blocking the RNA polymerase. In the absence of antibiotic, transcription from the ETR linked promoter is absent or minimal. When antibiotic is added, however, the polypeptide that binds ETR is released, thereby allowing transcription to occur.

In an alternative embodiment, a fusion protein that binds ETR can be used to repress transcription. In one aspect, the first polypeptide is operatively linked, as described above, to a second polypeptide which directly or indirectly represses transcription in eukaryotic cells. Proteins and polypeptide domains within proteins which can function to repress transcription in eukaryotic cells have been described in the art (for reviews see, e.g., Renkawitz, R., 1990, Trends in Genetics 6:192-197; and Herschbach, B. M. and Johnson, A. D., 1993, Annu. Rev. Cell. Biol. 9:479-509). Such domains can have a direct inhibitory effect on the transcriptional machinery or can repress transcription indirectly by inhibiting the activity of activator proteins. Accordingly, the term "a polypeptide that represses transcription in eukaryotic cells" as used herein is intended to include polypeptides which act either directly or indirectly to repress transcription. As used herein, "repression" of transcription is intended to mean a diminution in the level or amount of transcription of a target gene compared to the level or amount of transcription prior to regulation by the transcriptional inhibitor protein. Transcriptional inhibition may be partial or complete.

A transcriptional "repressor" or "silencer" domain as described herein is a polypeptide domain that retains its ability to repress transcription when the domain is transferred to a heterologous protein. Proteins which have been demonstrated to have repressor domains that can function when transferred to a heterologous protein include the v-erbA oncogene product (Baniahmad, A. et al., 1992, EMBO J. 11: 1015-1023) (e.g., approximately amino acid residues 362-632 of the native v-erbA oncogene product), the thyroid hormone receptor (Baniahmad, supra), the retinoic acid receptor (Baniahmad, supra), the *Drosophila* Krueppel (Kr) protein (Licht, J. D. et al, 1990, Nature 346:76-79; Sauer, F. and Jackle, H., 1991, Nature 353:563-566; Licht, J. D. et al., 1994, Mol. Cell. Biol. 14:4057-4066) (such as C64KR, which is amino acids 403-466 of the native protein, or amino acids 26-110 of Kr), and the KRAB domain of the kox1 gene family (Deuschle et al., 1995, Mol. Cell. Biol. 15:1907-1914). Other proteins which have transcriptional repressor activity in eukaryotic cells include the *Drosophila* homeodomain protein even-skipped (eve) (Han and Manley, 1993, Genes & Dev. 7: 491-503), the *S. cerevisiae* Ssn6/Tup1 protein complex (Herschbach and Johnson, supra), the yeast SIRI protein (see Chien et al., 1993, Cell 75:531-541), NeP1 (see Kohne et al., 1993, J. Mol. Biol. 232:747-755), the *Drosophila* dorsal protein (see Kirov et al., 1994, Mol. Cell. Biol. 14:713-722; Jiang, et al., 1993, EMBO J. 12:3201-3209), TSF3 (see Chen, et al., 1993, Mol. Cell. Biol. 13:831-840), SF1 (see Targa, et al., 1992, Biochem. Biophys. Res. Comm. 188:416-423), the *Drosophila* hunchback protein (see Zhang, et al., 1992, Proc. Natl. Acad. Sci. USA 89:7511-7515), the *Drosophila* knirps protein (see Gerwin, et al., 1994, Mol. Cell. Biol. 14:7899-7908), the WT1 protein (Wilm's tumor gene product) (see Anant, et al., 1994, Oncogene 9:3113-3126; Madden et al., 1993, Oncogene 8:1713-1720), Oct-2.1 (see Lillycrop, et al., 1994, Mol. Cell. Biol. 14:7633-7642), the *Drosophila* engrailed protein (see Badiani, et al., 1994, Genes Dev. 8:770-782; Han and Manley, 1993, EMBO J. 12:2723-2733), E4BP4 (see Cowell and Hurst, 1994, Nucleic Acids Res. 22:59-65) and ZF5 (see Numoto, et al., 1993, Nucleic Acids Res. 21:3767-3775).

Non-limiting examples of polypeptide domains that can be used as silencing domains include: amino acid residues 120-410 of the thyroid hormone receptor alpha (THR.alpha.), amino acid residues 143-403 of the retinoic acid receptor alpha (RAR.alpha.), amino acid residues 186-232 of knirps, the N-terminal region of WT 1 (see Anant, supra), the N-terminal region of Oct-2.1 (see Lillycrop, supra), a 65 amino acid domain of E4BP4 (see Cowell and Hurst, supra) and the N-terminal zinc finger domain of ZF5 (see Numoto, supra). Moreover, shorter or longer polypeptide fragments encompassing these regions that still retain full or partial repression activity are also contemplated.

In addition to previously described transcriptional repressor domains, novel transcriptional repressor domains, which can be identified by standard techniques (e.g., reporter gene constructs), are within the scope of the invention.

Construction of the nucleic acids of the invention can be accomplished by those of skill in the art using standard molecular biology techniques (see, for example, Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). Typically, manipulation and generation of nucleic acids is performed using prokaryotic host cells, but the invention also encompasses chemical synthetic methods of nucleic acid generation and manipulation.

The host cells for use in the methods and compositions of the invention include any eukaryotic cell such as mammalian cells, fungal cells, plant cells, insect cells and microbial parasites. The invention is illustrated below by way of non-limiting examples using a variety of mammalian cells. However, other types of eukaryotic cells can also be used. For example, the tetracycline-regulatable promoter system has been adapted for use in yeast (Gari et al., 1997, Yeast 13:837-848); similarly, the methods and compositions of the invention can also be used in such cells. Suitable host cells include, for example, mammalian cells such as CHO-K1, BHK-21, HeLa, COS-7, HEK 293, HEK 293T, HT1080, PC12, MDCK, C2C12, Jurkat, NIH3T3, K-562, TF-1 or human embryonic stem cells like clone H9 (WiCell, Madison, Wis., USA) or plant cells such as those derived from barley, wheat, rice, soybean, potato, tobacco (e.g. *Nicotiana tabacum* SR1) and arabidopsis. Suitable hosts also include plant-derived hairy roots such as those derived from Artemisia, Atropa, Beta, Brugmansia and others such as those described in Shanks and Morgan, 1999, Curr. Opin. Biotechnol. 10:151-155. Other suitable cell lines of mammalian and plant origin are well known to those of skill in the art and include, for example, those described in *ATCC Cell Lines and Hybridomas* 8th *Edition,* 1994, American Type Culture Collection, Rockville, Md.

Methods of genetically engineering a host cell to contain the nucleic acids of the invention are well known to those of skill in the art and include transformation, transfection, transduction and electroporation. The nucleic acids can be carried extrachromasomally or on the chromosome. Integration can be random, homologous, or site-specific recombination. Culturing a host cell is understood to include both in vitro culture and in vivo culture (for example, growing eukaryotic cells in tissue culture, growing cells in a host organism such as by implantation in a body cavity or graft, removing cells from a particular individual and replacing them after genetically engineering the cells to contain the nucleic acids of the invention, or by performing in vivo gene transfer by appropriate vector systems (e.g. viral vectors, etc.).

Furthermore, the present invention provides non-human transgenic animals having cells comprising nucleic acids encoding the proteins and fusion proteins of the invention. Such host cells optionally contain a desired nucleotide sequence to be transcribed operatively linked to an ETR sequence. The non-human transgenic animals contemplated by the present invention generally include any vertebrates, and preferably mammals. Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig, and non-human primates, such as chimpanzee, may be used to practice the present invention. Particularly preferred animals are rats, rabbits, guinea pigs, and most preferably mice.

Detailed methods for generating non-human transgenic animals are known to those of skill in the art and include, for example, those described in Schnieke et al., Science, 1997, 278: 2130-2133, Chan et al., Science, 2001, 291: 309-312 and Hogan et al., 1994, Manipulating the mouse embryo, 2nd edition, Cold Spring Harbor Laboratory Press, Cold Spring Harbor, N.Y.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor.

Introduction of a transgene into an embryo can be accomplished by any means known in the art such as, for example, microinjection, electroporation, or lipofection. For example, a construct can be introduced into a mammal by microinjection of the construct into a mammalian oocyte to cause one or more copies of the construct to be retained in the cells of the developing mammal. Following introduction of the transgene construct into the oocyte, the oocyte may be incubated in vitro for varying amounts of time, or implanted into a surrogate host, or both. In vitro incubation to maturity is within the scope of this invention. One common method is to incubate embryos in vitro for about 1-7 days, depending on the species, and then reimplant them into a surrogate host.

The progeny of transgenically manipulated embryos can be tested for the presence of the construct by any means known to those of skill in the art including, for example, Southern blot analysis or PCR analysis of a segment of tissue. If one or more copies of the exogenous cloned construct is stably integrated into the genome of such transgenic embryos, it is possible to establish permanent transgenic mammalian lines carrying the transgenically added construct.

The litters of transgenically altered mammals can be assayed after birth for the incorporation of the construct into the genome of the offspring. Preferably, this assay is accomplished by PCR analysis or by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

The number of copies of the transgene constructs which are added to the oocyte is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents. Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

A variety of vectors may be used to engineer host cells and transgenic animals to contain the nucleic acids of the invention. Suitable mammalian expression vectors include pSG5, pCMV-Script, pEF6, pcDNA3.1, pcDNA4 series, pEF1, pBK-CMV, pBK-RSV, pSBC-1, pSBC-2. Suitable viral vectors include adenoviral vectors, adeno-associated viral vectors, retroviral vectors, alphaviral vectors, lentiviral vectors and other viral vectors known to those of skill in the art. Suitable retroviral and/or lentiviral vectors include, for example, pLAPSN, pLHCX, pLIB, pLNCX2, pLNHX, pLBCX, pLXRN, pLXSN, pMSCVneo, pSIR and lentiviral vectors such as those described by Reiser et al., Proc. Natl. Acad. Sci, 1996, 93: 15266-15271; Reiser et al., J. Virol., 2000, 74: 10589-10599; Mochizuki et al., J. Virol., 1998, 72:8873-8883; Naldini and Verma, 1999, 47-60 (and references therein) in Friedman (ed.) The development of human gene therapy. Cold Spring Harbor Laboratory Press, Cold Spring Harbor, N.Y.). Vectors constructed according to methods described in Coffin et al., 1997, Retroviruses, Cold Spring Harbor Laboratory Press, New York are also within the scope of this invention.

Suitable plant expression vectors include, for example, pBI, pRT99, pGPTV series, pGSV4, pBI 121, pBI221, pBI101, pKIVI105, pBIN19, pPZP121, and the pCAMBIA family).

Additional suitable vectors will be apparent to those of skill in the art and include, for example, those described in *ATCC Catalogue of Recombinant DNA Materials $3^{rd}$ Edition,* 1993, American Type Culture Collection, Rockville, Md., and those listed on the internet page of the American Type Culture Collection.

An ETR-linked gene is defined herein as a promoter which directs the expression of a coding sequence, wherein the promoter and coding sequence are operatively linked to an ETR sequence. Preferably, the promoter is a eukaryotic promoter. By operatively linked in this context is meant that the ETR sequence is placed proximal to the promoter, either 5' to, or 3' to, or within the sequence of the promoter, such that when a fusion protein that modulates transcription is bound to the ETR sequence, initiation of transcription at the promoter is affected.

The coding sequence operatively linked to the promoter can encode for any gene product for which regulated expression is desired, and can be exogenous to the host cell or endogenous. By endogenous coding sequence is meant coding sequence that is naturally present in the host cell and not introduced into the host cell via transformation techniques. Exogenous coding sequence is not endogenous coding sequence. Coding sequences include not only sequences encoding proteins, but also other coding sequences, e.g., encoding antisense gene products, ribozymes, etc. Further, the coding sequences can be multicistronic (see, for example, U.S. Pat. No. 6,274,341).

Production of any gene product can be regulated using the compositions and methods of the present invention. For example, production of a marker gene product, such as green fluorescent protein (GFP), or of a model secreted gene product, such as SEAP (human placental secreted alkaline phosphatase) or SAMY (secreted amylase, Moser et al., 2001 Journal of Gene Medicine 3, 1-23), may be regulated. Other marker gene products useful with the compositions and methods of the invention include of beta-glucuronidase (GUS), red fluorescent protein (RFP), yellow fluorescent protein (YFP), cyan fluorescent protein (CFP) (see, e.g., Hawley et al., 2001, Biotechniques 30:1028-34; Lansford et al., 2001, J Biomed Opt. 6:311-8; Ottenschlager et al., 1999, Transgenic Res. 8:279-94). Naturally, the invention finds particular use in the production of products of industrial or pharmaceutical interest such as industrial enzymes (e.g. proteases, cellulases, glycosidases, or ligninases), interferons (e.g. β-INF, α-INF, γ-INF), hGH, insulin, erythropoietin, tissue plasminogen activator (tPA), DNAse, monoclonal antibodies, Factor VIII, Factor VII, Factor IX, HSA, IL-2, glucagon, EGF, GCSF, GMCSF, thrombopoietin, gp160, HbSAg, and other viral antigenic proteins and peptides (rotavirus, HIV, p53ras).

Another aspect of the invention is the use of tumor suppressor gene products to regulate proliferation of host cells of the invention. Regulated expression of tumor suppressor gene products are particularly useful for a variety of applications. For example, one may want the host cells to undergo a rapid proliferation phase followed by a production phase where cellular energies are devoted to protein production, or a rapid proliferation phase in vitro followed by regulated growth in vivo (see, for example, U.S. Pat. No. 6,274,341, the disclosure of which is incorporated by reference). For purposes of the invention, tumor suppressor gene products include proteins that block the cell cycle at a cell cycle checkpoint by interaction with cyclins, Cdks or cyclin-Cdk complexes, or by induction of proteins that do so. Thus, these tumor suppressor gene products inhibit the cyclin-dependent progression of the cell cycle. Particularly preferred tumor suppressor gene products act on the G1-S transition of the cell cycle. The invention encompasses the use of any tumor suppressor gene product which performs this function, whether known or yet to be discovered. Examples of tumor suppressor genes include p21, p27, p53

(and particularly, the p53175P mutant allele), p57, p15, p16, p18, p19, p73, GADD45, and APC1.

Optionally, one can also use the methods and compositions of the invention to express survival factors in the host cells. Survival factors are intracellular proteins that prevent apoptosis such as bcl-2, bcl-$x_L$, E1B-19K, mcl-1, crmA, abl, p35, bag-1, A20, LMP-1, Tax, Ras, Rel and NF-κB-like factors, and a dominant negative mutant of caspase-9 (Angelastro et al., J. Biol. Chem., 2001.276:12190-12200). Additionally, all known survival factors, as well as survival factors yet to be discovered, are useful in the methods and compositions of the invention. In yet another embodiment, the tumor suppressor gene(s) can be expressed concomitantly with a factor that stabilizes the tumor suppressor gene product in the cell. Examples of stabilizing factors are members of the CAAT enhancer binding protein family. For example, p21 protein activity is stabilized when coexpressed with C/EBPα. Additionally, C/EBPα specifically induces transcription of the endogenous p21 gene. Thus, C/EBPα functions as both a stabilizing factor and as a specific inducer of p21.

Still another aspect of the invention is the use of the nucleotides and methods of the invention to express a gene product that activates cell proliferation. For example genetic determinants exerting positive control of mammalian cell cycle that can be used as a protein that activates cell proliferation are cyclins (e.g., cyclin E), Ras, Raf, the MAP kinase family (e.g., MAP, Erk, Sap) E2F, Src, Jak, Jun, Fos, pRB, Mek2, EGF, TGF, PDGF, and a polynucleotide that is antisense to a tumor suppressor gene (e.g., p27 anti-sense expression has been shown to stimulate proliferation of quiescent fibroblasts and enable growth in serum-free medium (Rivard et al., 1996, J. Biol. Chem. 271: 18337-18341, Fux et al., 2001. Nucleic Acids Res. 29: e19, PCT application no. 00/65080) and nedd5 which is known as positive growth controlling gene (Kinoshita et al., 1997, Genes Dev. 11: 1535-1547).

One exemplary embodiment of the present invention is illustrated below by the development of a new system for antibiotic-regulated gene expression in eukaryotic cells based on the repressor of a macrolide resistance operon of E. coli (MphR(A)) (Noguchi et al., 2000. supra). A chimeric protein (ET) comprised of MphR(A) fused to a eukaryotic transactivator was able to control expression of a synthetic eukaryotic promoter ($P_{ETR}$) containing the MphR(A) binding site (ETR). Genes placed under the control of this ET/$P_{ETR}$ system were responsive to clinically approved therapeutic compounds belonging to the macrolide group (erythromycin, clarithromycin, roxithromycin and tylosin) in a variety of mammalian cell lines (CHO-K1, COS-7, HEK-293T and HeLa) and plant cells (Nicotania tabacum SR-1). This novel system exhibited superior inducibility and lower background expression properties compared to the well-established tetracycline-based system in CHO cells engineered to provide three independent regulation systems including macrolide-, streptogramin- and tetracycline-responsive regulation. In these cells therapeutically relevant concentrations of pristinamycin and tetracycline have only minor effects on expression from the macrolide-responsive ET/$P_{ETR}$ system. The presence of erythromycin resulted in an increase of maximum expression for the tetracycline and streptogramin responsive promoters. As a result of these studies, these three different systems can be used together in advanced future therapies requiring independent regulation of different transgenes. In addition, responsiveness of the ET/$P_{ETR}$ system to all macrolide antibiotics tested indicates that reporter gene expression from $P_{ETR}$ can be used as an efficient high-throughput assay for discovery of new macrolides. The same concept applies to other eukaryotic antibiotic-responsive transcription regulation systems, which can be linked to a reporter gene for the discovery of new antibiotics.

Still another aspect of the invention includes multipurpose expression vectors, as well as cells and methods using the same, which take advantage of the antibiotic dependent activator and repressor systems of the invention. Such vectors can be mono, di- or multicitronic. Non-limiting examples of such vectors are described below by way of working embodiments.

Although the regulated gene expression invention described herein was originally designed for general applications in functional genomic research, gene therapy and tissue engineering, the finding that the macrolide system illustrated below by way of nonlimiting example responds to all tested commercially available macrolides, including clarithromycin and tylosin, indicates its use as a powerful screening tool for the discovery of novel antibiotics. Accordingly, still another aspect of the invention is a method of screening for candidate antibiotics. The method entails incubating the host cells of the invention, the host cells containing a $P_{ETR}$-linked reporter gene and a sequence encoding a $P_{ETR}$-binding protein, in the presence of a test compound, wherein a change in the transcription of the reporter gene indicates that the test compound is a candidate antibiotic.

For example, detection of macrolides is based on addition of metabolic libraries of any prokaryotic, fungal or plant origin to cultured mammalian cells containing the erythromycin-responsive reporter system. The presence of macrolides or structurally related compounds will downregulate expression of the reporter protein, for example SEAP, driven by $P_{ETR}$. By using an alternative expression configuration (see example 4) presence of macrolides induces expression of the reporter gene. This screening approach offers three decisive advantages over classical screening technology using indicator bacteria-based antibiogram tests: (i) Antibiotic screening is not limited by the sensitivity of indicator bacteria to a yet uncharacterized macrolides (sensitivity of bacteria to antibiotics greatly varies between strains and even isolates), and (ii) the mammalian cell-based macrolide detection concept shows at least one order of magnitude higher sensitivity to this class of antibiotics than antibiogram tests based on bactericidal activity and iii) when the test compound is applied to isogenic cells with constitutive expression of the same reporter-gene, a decrease in reporter-gene activity indicates possible undesired cytotoxic side-effects of the tested compounds.

The use of this macrolide antibiotic detection assay is not only limited to the screening for novel macrolide compounds, but can be also used for the sensitive and specific detection of residual macrolide antibiotics in food and other samples of different origin.

Detection of macrolide compounds can also be performed in cell free systems by analyzing the interaction of ETR-binding proteins with their cognate DNA-sequence. In such an embodiment presence of macrolides in the test sample induces dissociation of the ETR-binding protein from its cognate DNA-sequence, whereas absence of macrolides results in binding of the two components. Preferred systems are those, in which one binding partner (ETR-binding protein or its cognate DNA-sequence) is immobilized on a solid support like beads, magnetic beads, microtiter plates, test strips and other devices known to those of skill in the art. The second binding partner is preferably labeled with compounds for its facilitated detection like reporter-enzymes, dyes, fluorophores and radioactivity. These compounds can be coupled to the second binding partner either covalently or by affinity via a linker.

The assay is performed by incubating a test sample with the ETR-binding protein and its cognate DNA-sequence with subsequent removal of the first binding partner coupled to the solid phase. Absence of the second binding partner on the solid phase (as detected via its label) shows dissociation of the ETR-binding protein from its cognate DNA-sequence and indicates therefore the presence of macrolide compounds in the test sample.

In extension to this solid-phase based assay other setups are possible, for example where interaction of the ETR-binding protein with its cognate DNA sequence is analyzed by other methods known in the art like fluorescence resonance energy transfer (FRET) or BiaCore binding analysis. These methods are also within the scope of the invention.

Also, extension of these detection concepts to include antibiotic-responsive reporter gene expression using other resistance operons from other *Enterobacteriaceae* and transposons of *Enterobacteriaceae* is within the scope of this invention.

In another aspect the present invention provides kits for regulated expression of a gene in a eukaryotic cell. The kits typically comprise a first polynucleotide and a second polynucleotide. The first polynucleotide can encode a polypeptide capable of macrolide-responsive regulation of the expression of the gene in eukaryotes. The polypeptide can be any polypeptide of the invention as described above including, for example, a transactivator or transrepressor fusion polypeptide. The fusion polypeptide can comprise a macrolide responsive repressor polypeptide and a polypeptide capable of activating or repressing expression in eukaryotes. The second polynucleotide can comprise a minimal promoter operably linked to at least one ETR operator sequence capable of being linked to the gene to be regulated. The kits can optionally further comprise eukaryotic cells for the regulated expression of the gene and a macrolide antibiotic for regulation of the expression of the gene, other materials known to those of skill in the art to be useful in the kits such as materials for linking the second polynucleotide to the gene to be regulated, for transfection of cells, and so forth.

The invention also provides kits for macrolide-regulated expression of a gene in a eukaryotic cell. The kits typically comprise a eukaryotic cell, wherein the cell is transfected with a first polynucleotide, and a second polynucleotide. The first polynucleotide typically encodes a polypeptide capable of modulating the expression of the gene in a eukaryotic cell in response to a macrolide antibiotic. The polypeptide can be any polypeptide of the invention capable of macrolide-responsive gene regulation as described above. For instance, the polypeptide can be a transactivator or transrepressor fusion polypeptide comprising a prokaryotic macrolide-responsive repressor polypeptide and a polypeptide capable of activating or repressing transcription in eukaryotes. The second polynucleotide can comprise a promoter operably linked to at least one ETR operator sequence. The second polynucleotide can be capable of being linked to the gene so that expression of the gene can be modulated with a macrolide antibiotic. The kit can optionally comprise a macrolide antibiotic and other materials known to those of skill in the art to be useful in the kit such as materials for linking the second polynucleotide to the gene to be regulated, for transfection of cells, and so forth.

The invention having been described, the following examples are offered by way of illustration and not limitation.

Example 1

Macrolide-repressible Mammalian Gene Regulation System (E.REX)

This example describes the use of MphR(A) and ETR to design a novel macrolide-responsive mammalian gene regulation system with excellent regulatory properties which is functionally compatible with the streptogramin (PIP-system)- and tetracycline-based (tet-system) transcription regulation systems most widely used.

Methods

Construction of the Macrolide-dependent Transactivators (ET) and the Erythromycin-Regulatable Promoter $P_{ETR}$ ET1, the fusion protein of MphR(A) and the VP16 C-terminal transactivation domain of Herpes simplex (Triezenberg et al., 1988, Genes Dev. 2, 718-729) was constructed by amplifying MphR(A) from pTZ3509 (Noguchi et al., 2000. J. Bacteriol. 182, 5052-5058) with oligos: OWW18: 5'-GTACGAATTCCCACCatgccccgc-cccaagctcaa-3' (SEQ ID NO 2) and OWW19: 5'-GCGCGCGGCTGTACGCGGAcgcatgtgc-ctggaggagttggaa-3' (SEQ ID NO 3) and cloned into pEF6/V5/His-TOPO (Invitrogen) under control of the human elongation factor 1α promoter, $P_{EF1\alpha}$ (pWW29 (FIG. 1), Uetsuki et al., 1989. J. Biol. Chem. 264, 5791-5798)

Amplified sequence of MphR(A) (SEQ ID NO 4).

```
gtacgaattcccaccATGCCCCGCCCCAAGCTCAAGTCCGATGACGAGGT

ACTCGAGGCCGCCACCGTAGTGCTGAAGCGTTGCGGTCCCATAGAGTTCA

CGCTCAGCGGAGTAGCAAAGGAGGTGGGGCTCTCCCGCGCAGCGTTAATC

CAGCGCTTCACCAACCGCGATACGCTGCTGGTGAGGATGATGGAGCGCGG

CGTCGAGCAGGTGCGGCATTACCTGAATGCGATACCGATAGGCGCAGGGC

CGCAAGGGCTCTGGGAATTTTTGCAGGTGCTCGTTCGGAGCATGAACACT

CGCAACGACTTCTCGGTGAACTATCTCATCTCCTGGTACGAGCTCCAGGT

GCCGGAGCTACGCACGCTTGCGATCCAGCGGAACCGCGCGGTGGTGGAGG

GGATCCGCAAGCGACTGCCCCCAGGTGCTCCTGCGGCAGCTGAGTTGCTC

CTGCACTCGGTCATCGCTGGCGCGACGATGCAGTGGGCCGTCGATCCGGA

TGGTGAGCTAGCTGATCATGTGCTGGCTCAGATCGCTGCCATCCTGTGTT

TAATGTTTCCCGAACACGACGATTTCCAACTCCTCCAGGCACATGCGtcc gcgtacagccgcgcgc
```

The MphR(A)-containing EcoRI/BssHII fragment of pWW29 was subsequently cloned into pSAM200 (Fussenegger et al., 2000. Nat. Biotechnol. 18, 1203-1208) (EcoRI/BssHII), replacing the TetR domain of tTA by MphR(A) (ET1, pWW35, MphR(A)-VP16, FIG. 2).

The resulting plasmid has the following coding sequence:

ET1 sequence (SEQ ID NO 5)

```
ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

CGCGATACGCTGCTGGTGAGGATGATGGAGCGCGGCGTCGAGCAGGTGCG
```

-continued
GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

TCATGTGCTGGCTCAGATCGCTGCCATCCTGTGTTTAATGTTTCCCGAAC

ACGACGATTTCCAACTCCTCCAGGCACATGCGtccgcgtacagccgcgcg cGTACGAAAAACAATTACGGGTCTACCATCGAGGGCCTGCTCGATCTCCC

GGACGACGACGCCCCCGAAGAGGCGGGGCTGGCGGCTCCGCGCCTGTCCT

TTCTCCCCGCGGGACACACGCGCAGACTGTCGACGGCCCCCCCGACCGAT

GTCAGCCTGGGGACGAGCTCCACTTAGACGGCGAGGACGTGGCGATGGC

GCATGCCGACGCGCTAGACGATTTCGATCTGGACATGTTGGGGGACGGGG

ATTCCCCGGGTCCGGGATTTACCCCCCACGACTCCGCCCCCTACGGCGCT

CTGGATATGGCCGACTTCGAGTTTGAGCAGATGTTTACCGATGCCCTTGG

AATTGACGAGTACGGTGGGTAG

For construction of ET2 (pWW42, FIG. 2) the VP16 domain of pWW35 was replaced by BssHII/HindIII restriction with the p65 transactivation domain of NF-κB (of pMF197 (disclosed in PCT application no. WO 00/65080). pWW42 contains the following coding sequence:

Sequence of ET2 (SEQ ID NO: 6):

ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

CGCGATACGCTGCTGGTGAGGATGATGGAGCGCGGCGTCGAGCAGGTGCG

GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

TCATGTGCTGGCTCAGATCGCTGCCATCCTGTGTTTAATGTTTCCCGAAC

ACGACGATTTCCAACTCCTCCAGGCACATGCGTCCGCGTACAGCCGCGCG

CATGATGAGTTTCCCACCATGGTGTTTCCTTCTGGGCAGATCAGCCAGGC

CTCGGCCTTGGCCCCGGCCCCTCCCCAAGTCCTGCCCCAGGCTCCAGCCC

CTGCCCCTGCTCCAGCCATGGTATCAGCTCTGGCCCAGGCCCCAGCCCCT

GTCCCAGTCCTAGCCCCAGGCCCTCCTCAGGCTGTGGCCCCACCTGCCCC

CAAGCCCACCCAGGCTGGGGAAGGAACGCTGTCAGAGGCCCTGCTGCAGC

TGCAGTTTGATGATGAAGACCTGGGGGCCTTGCTTGGCAACAGCACAGAC

CCAGCTGTGTTCACAGACCTGGCATCCGTCGACAACTCCGAGTTTCAGCA

-continued
GCTGCTGAACCAGGGCATACCTGTGGCCCCCCACACAACTGAGCCCATGC

TGATGGAGTACCCTGAGGCTATAACTCGCCTAGTGACAGGGGCCCAGAGG

CCCCCCGACCCAGCTCCTGCTCCACTGGGGGCCCCGGGGCTCCCCAATGG

CCTCCTTTCAGGAGATGAAGACTTCTCCTCCATTGCGGACATGGACTTCT

CAGCCCTGCTGAGTCAGATCAGCTCCTAA

Figure 2A:
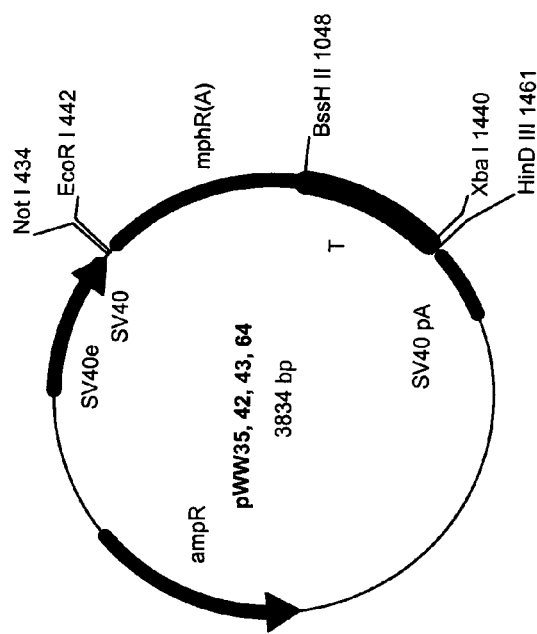
FIGS. 2a and 2b: Graphical representation of vectors pWW35, pWW42, pWW43, and pWW64 (shown in FIG. 2a), and vectors pBP37, pBP38, and pBP39 (shown in FIG. 2b) which encode different ET-proteins where ET is a fusion protein of an ETR-binding protein and proteins with transcriptional-activating or -repressing activity: T stands for: VP16 transactivation domain of the herpes simplex virus (pWW35) (the amino acid sequence of which is disclosed in Triezenberg et al., 1988, Genes Dev. 2: 718-729); for the p65 transactivation domain of NF-κB (pWW42) (Schmitz and Baeuerle, 1991, EMBO J. 10: 3805-3817); for the KRAB transrepressor domain of the human kox gene (pWW43) (Moosmann et al., 1997, Biol. Chem., 387: 669-677); for the transactivation domain of the human E2F4 transcription factor (pWW64) (Akagi et al., 2001, Nucleic Acids Res., 29: e23); for the repeated FFF domain of the VP 16 transactivation domain (pBP37); for the repeated FF domain of the VP16 transactivation domain (pBP38); for the GFY domain of the VP16 transactivation domain (pBP39) (Baron et al., 1997. Nucleic Acids Res., 25, 2723-2729).
Figure 2B:
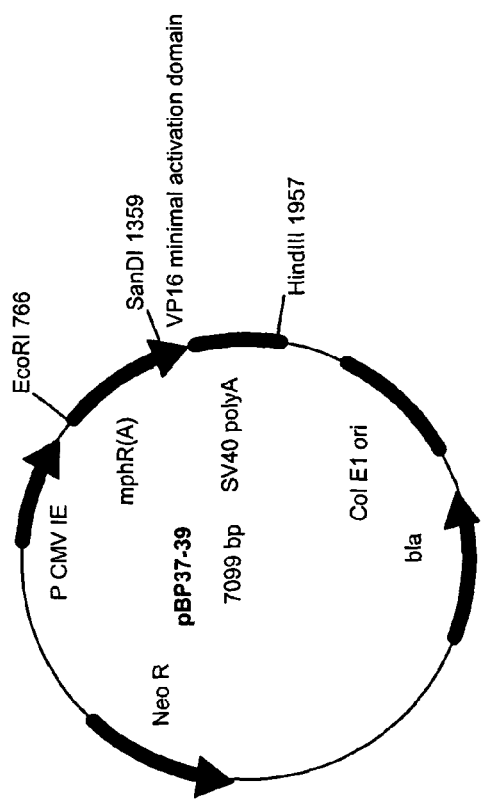

For construction of ET3 (FIG. 2, pWW64, MphR(A)-E2F4) the human transactivation domain of E2F4 was amplified from prTE4d38neo (Akagi et al., 2001. Nucleic Acids Res 29, e23) with OWW27: 5'-gcgcgCGGCCACT-GCAGTCTTCT-3' (SEQ ID NO 7) and OWW28: 5'-ggtcta-gaggatccTCAGAGGTTGAGAACA-3' (SEQ ID NO 8) and ligated (BssHII/XbaI) into pWW35 thus replacing the VP16 domain and resulting in the following coding sequence:

Sequence of ET3 (SEQ ID NO 9):

ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

CGCGATACGCTGCTGGTGAGGATGATGGAGCGCGGCGTCGAGCAGGTGCG

GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

TCATGTGCTGGCTCAGATCGCTGCCATCCTGTGTTTAATGTTTCCCGAAC

ACGACGATTTCCAACTCCTCCAGGCACATGCGtccgcgtacagccgcgcg

CGGCCACTGCAGTCTTCTGCCCTGCTGGACAGCAGCAGCAGCAGCAGCAG

CAGCAGCAGCAGCAGCAGCAACAGTAACAGCAGCAGTTCGTCCGGACCCA

ACCCTTCTACCTCCTTTGAGCCCATCAAGGCAGACCCCACAGGTGTTTTG

GAACTCCCCAAAGAGCTGTCAGAAATCTTTGATCCCACACGAGAGTGCAT

GAGCTCGGAGCTGCTGGAGGAGTTGATGTCCTCAGAAGTGTTTGCCCCTC

TGCTTCGTCTTTCTCCACCCCCGGGAGACCACGATTATATCTACAACCTG

GACGAGAGTGAAGGTGTCTGTGTGCCTGTTCTCAACCTCTGA

For construction of the transrepressor ET4 (MphR(A)-KRAB, pWW43, FIG. 2) the KRAB-KRAB-containing BssHII/HinDIII of pMF203 (Fussenegger et al., 2000. Nat. Biotechnol. 18, 1203-1208) was inserted into the corresponding sites of pWW35 thus replacing the VP16 domain and resulting in the following sequence:

Sequence of ET4: (SEQ ID NO 10):

ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

-continued
CGCGATACGCTGCTGGTGAGGATGATGGAGCGCGGCGTCGAGCAGGTGCG

GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

TCATGTGCTGGCTCAGATCGCTGCCATCCTGTGTTTAATGTTTCCCGAAC

ACGACGATTTCCAACTCCTCCAGGCACATGCGTCCGCGTACAGCCGCGCG

CCAGATCCAAAAAAGAAGAGAAAGGTAGATCCAAAAAAGAAGAGAAAGGT

AGATCCAAAAAAGAAGAGAAAGGTAATGGATGCTAAGTCACTAACTGCCT

GGTCCCGGACACTGGTGACCTTCAAGGATGTATTTGTGGACTTCACCAGG

GAGGAGTGGAAGCTGCTGGACACTGCTCAGCAGATCGTGTACAGAAATGT

GATGCTGGAGAACTATAAGAACCTGGTTTCCTTGGGTTATCAGCTTACTA

AGCCAGATGTGATCCTCCGGTTGGAGAAGGGAGAAGAGCCCTGGCTGGTG

GAGAGAGAAATTCACCAAGAGACCCATCCTGATTCAGAGACTGCATTTGA

AATCAAATCATCAGTTTCCAGCAGGAGCATTTTTAAAGATAAGCAATCCT

GTGACATTAAAATGGAAGGAATGGCAAGGAATGATCTCTGGTAA

Construction of the Transactivator ET5 (FIG. 2).

MphR(A) was amplified of pTZ3509 (Noguchi et al., 2000. J. Bacteriol. 182: 5052-5058) with oligos OWW18 (SEQ ID NO 2, supra) and OBK8: GGGACCCcgcatgtgcctggaggagt-tggaa (SEQ ID NO 11) and subsequently cloned into pEF6/V5-His TOPO (Invitrogen) without taking care of orientation thus resulting in pBP27. The MphR(A) containing fragment was excised (EcoRI/SanDI) from pBP27 and cloned (EcoRI/SanDI) into ptTA2 (Clontech) thus resulting in pBP37 encoding ET5 which is a fusion protein of MphR(A) and the trimeric FFF transactivation domain of the herpes simplex VP16 transactivator (Baron et al., 1997. Nucleic Acids Res. 25: 2723-2729). ET5 has the following coding sequence (Sequence ID 12):

ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

CGCGATACGCTGCTGGTGAGGATGATGGAGCGCGGCGTCGAGCAGGTGCG

GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

TCATGTGCTGGCTCAGATCGCTGCCATCCTGTGTTTAATGTTTCCCGAAC

ACGACGATTTCCAACTCCTCCAGGCACATGCGgggtcccCGGCCGACGCC

CTGGACGACTTCGACCTGGACATGCTGCCGGCCGACGCCCTGGACGACTT

CGACCTGGACATGCTGCCGGCCGACGCCCTGGACGACTTCGACCTGGACA

TGCTGCCGGGGTAA

The transactivator ET6 (FIG. 2) was constructed by excising (EcoRI/SanDI) the MphR(A) containing fragment of pBP27 (supra) and cloning (EcoRI/SanDI) into ptTA3 (Clontech) thus resulting in pBP38 encoding ET6, which is a fusion protein of MphR(A) and the dimeric FF-transactivation domains of the herpes simplex VP16 transactivator (Baron et al., 1997. Nucleic Acids Res. 25: 2723-2729). ET6 has the following coding sequence (Sequence ID 13):

ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

CGCGATACGCTGCTGGTGAGGATGATGGAGCGCGGCGTCGAGCAGGTGCG

GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

TCATGTGCTGGCTCAGATCGCTGCCATCCTGTGTTTAATGTTTCCCGAAC

ACGACGATTTCCAACTCCTCCAGGCACATGCGgggtcccCGGCCGACGCC

CTGGACGACTTCGACCTGGACATGCTGCCTGCTGATGCTCTCGATGATTT

CGATCTCGATATGCTCCCGGGTAACTAA

The transactivator ET7 (FIG. 2) was constructed by excising (EcoRI/SanDI) the MphR(A) containing fragment of pBP27 (supra) and cloning (EcoRI/SanDI) into ptTA4 (Clontech, Palo Alto, Calif.) thus resulting in pBP39 encoding ET7, which is a fusion protein of MphR(A) and the trimeric GFY-transactivation domains of the herpes simplex VP16 transactivator (Baron et al., 1997. Nucleic Acids Res. 25: 2723-2729). ET7 has the following coding sequence (Sequence ID 14):

ATGCCCCGCCCCAAGCTCAAGTCCGATGACGAGGTACTCGAGGCCGCCAC

CGTAGTGCTGAAGCGTTGCGGTCCCATAGAGTTCACGCTCAGCGGAGTAG

CAAAGGAGGTGGGGCTCTCCCGCGCAGCGTTAATCCAGCGCTTCACCAAC

CGCGATACGCTGCTGGTGAGGATGATGGAGCGCGGCGTCGAGCAGGTGCG

GCATTACCTGAATGCGATACCGATAGGCGCAGGGCCGCAAGGGCTCTGGG

AATTTTTGCAGGTGCTCGTTCGGAGCATGAACACTCGCAACGACTTCTCG

GTGAACTATCTCATCTCCTGGTACGAGCTCCAGGTGCCGGAGCTACGCAC

GCTTGCGATCCAGCGGAACCGCGCGGTGGTGGAGGGGATCCGCAAGCGAC

TGCCCCCAGGTGCTCCTGCGGCAGCTGAGTTGCTCCTGCACTCGGTCATC

GCTGGCGCGACGATGCAGTGGGCCGTCGATCCGGATGGTGAGCTAGCTGA

-continued

TCATGTGCTGGCTCAGATCGCTGCCATCCTGTGTTTAATGTTTCCCGAAC

ACGACGATTTCCAACTCCTCCAGGCACATGCGgggtccccGGCCGACGCC

CTGGACGACGGCGACCTGGACATGCTGCCTGCTGATGCTCTCGATGATTT

CGATCTCGATATGCTCCCGGCCGACGCCCTGGACGACTACGACCTGGACA

TCCTCCCGGGTAACTAA

TCCTCCCGGGTAACTAA $P_{ETR3}$ was constructed by amplification Of $P_{hCMVmin}$ from pRevTRE (Clontech, Palo Alto, Calif.) with oligos OWW23: 5'
GATCGACGTCGATTGAATATAAC-CGACGTGACTGTTACATTTAGGGTACACCTGC AGGtcgagctcggtacccgggtc-3' (SEQ ID NO 15) and OWW22: 5'-gctagaattcCGCGGAGGCTGGATCGG-3' (SEQ ID NO 16) and subsequently cloned into PEF6/V5-His TOPO (Invitrogen). The sequence of $P_{ETR3}$ (contained in pWW32) is the following:

Sequence of $P_{ETR3}$ (ETR motif in bold)(SEQ ID NO 17):

GACGTCGATTGAATATAACCGACGTGACTGTTACATTTAGGGTACACCTG

CAGGTCGAGCTCGGTACCCGGGTCGAGTAGGCGTGTACGGTGGGAGGCCT

ATATAAGCAGAGCTCGTTTAGTGAACCGTCAGATCGCCTGGAGACGCCAT

CCACGCTGTTTTGACCTCCATAGAAGACACCGGGACCGATCCAGCCTCCG

CGGAATTC.

Construction of the Erythromycin-Responsive Reporter Plasmids pWW38 and pWW44.

Figure 3A:
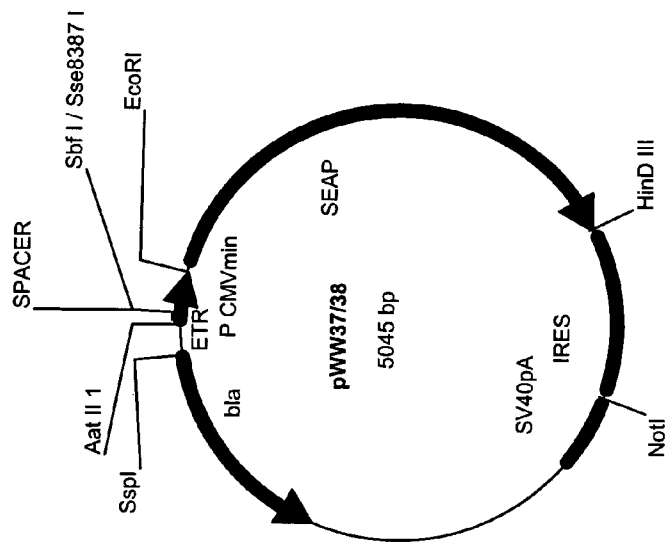
FIGS. 3a and 3b: Graphical representation of vectors pWW37 and pWW38 (shown in FIG. 3a), and vectors pBP10, pBP11, pBP12, pBP13 and pBP14 (shown in FIG. 3b). These vectors contain ETR-sequences functionally linked to the minimum human cytomegalovirus promoter $P_{hCMVmin}$ and the SEAP reporter gene (human placental secreted alkaline phosphatase). Spacers of different length separate the ETR-sequence and the minimal promoter sequence: pWW37: 0 bp; pBP10: 2 bp; pBP11: 4 bp; pWW38: 5 bp; pBP12: 6 bp; pBP13: 8 bp; pBP14: 10 bp.
Figure 3B:
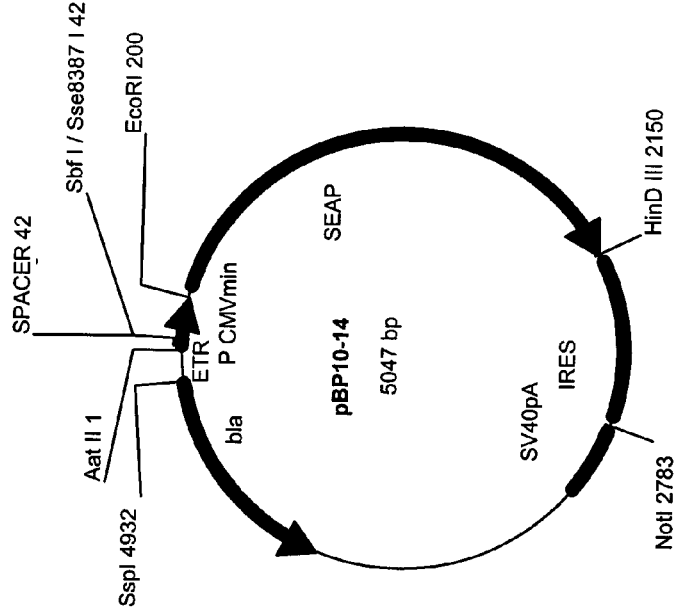

For construction of pWW38 (FIG. 3) the $P_{ETR3}$-containing fragment was excised from pWW32 by AatII and EcoRI and ligated to the corresponding sites (AatII/EcoRI) of pMF111 (disclosed PCT application no. 00/65080), thereby replacing the tet-responsive promoter $P_{hCMV*-1}$ and resulting in an erythromycin-responsive SEAP (human placental secreted alkaline phosphatase) driven expression vector. Similarly, pWW44 was constructed for qualitative analysis by inserting (EcoRI/HindIII) the cyan fluorescent protein (CFP, excised (EcoRI/HindIII) from pTFT2, (Moser et al., 2000. Biotechnol. Prog. 16, 724-735) under control of $P_{ETR3}$ thus replacing SEAP.

Cell Culture, Transfection, Construction of Stable Cell Lines and SEAP Activity Test.

Chinese hamster ovary cells (CHO-K1, ATCC: CCL 61), and HeLa cells (ATCC: CRL-7923) as well as stable cell lines derived thereof were cultured as described before (Fussenegger et al., 1998, Nat. Biotechnol. 16,468-472) in the presence of appropriate antibiotics: G418 400 µg/ml; zeocin 100 µg/ml. Optimized $CaPO_4$ protocols were used for high efficiency transient transfection of all cell lines (Fussenegger et al., 1998. Nat. Biotechnol. 16: 468-472). Transiently transfected cells were routinely analyzed after 48 h for CFP or SEAP expression using fluorescence microscopy and p-nitrophenolphosphate-based light absorbance timecourse, respectively, as described before (Fussenegger et al., 1998, Nat. Biotechnol. 16, 468-472; Berger et al., 1988, Gene 66, 1-10 b). For construction of stable CHO-ET1 and CHO-Triplet$_{42}$ cell lines, CHO-Ki and CHO-TWIN1$_{108}$ (Disclosed in PCT application no. 00/65080) were cotransfected with pWW35 and pZeoSV2 (invitrogen). CHO-ET1$_1$-SEAP was constructed by cotransfection of pWW38 and pSV2neo (Clontech) into CHO-ET1$_1$. The mixed populations were cloned using FACS-mediated single-cell-sorting (FACStar$^{Plus}$; Beckton Dickinson). For assessment of dose-response characteristics of $P_{ETR3}$-regulated gene expression, CHO-ET1$_1$-SEAP were cultured at cell densities of 50,000/ml for 48 h at various EM concentrations.

Regulating Macrolides

Erythromycin (Fluka, Buchs, Switzerland) was used as a stock solution of 2 mg/ml in ethanol. Other antibiotics were eluted from antibiotic test discs (Mast Diagnostica GmbH, Reinfeld, Germany, or bioMérieux, Geneva Switzerland) in cell culture medium at 37° C. for 12 h to reach a final concentration of 30 µg/ml. All macrolide antibiotics were used at a 2 µg/ml concentration unless indicated otherwise. For control experiments Pyostacin (PI, Aventis, lot RP 27404) and tetracycline (Sigma refs. T3383 and D9891) were used at 2 g/ml.

Results

Construction and Functional Studies of the Macrolide-based Gene Regulation System in CHO Cells In order to analyze the potential of the MphR(A)/ETR system for the design of a novel mammalian gene regulation system, we adapted these regulatory elements for use in a eukaryotic context by construction of a set of two chimeric determinants: the EM-inhibited transactivators (ET, MphR (A) fused to different eukaryotic transactivation domains: ET1: MphR(A)-VP16; ET2: MphR(A)-p65; ET3: MphR (A)-E2F4) and the EM-responsive promoter ($P_{ETR3}$) (ETR fused to the minimal cytomegalovirus $P_{hCMVmin}$; Gossen et al., (1992). Proc. Natl. Acad. Sci. USA 89, 5547-5551). Following transfection of a $P_{ETR3}$-driven CFP expression construct (pWW44) into CHO cells, no cyan fluorescence could be observed by fluorescence microscopy, indicating that no endogenous host factors activate $P_{ETR3}$. CFP-expression could only be detected when pWW44 was cotransfected with an ET1-encoding pWW35, showing that the chimeric ET1 protein functions as a transactivator for $P_{ETR3}$ in mammalian cells. Transactivation of CFP expression was strictly EM-dependent and could not be achieved by cotransfection of pWW44 with vectors containing other transactivators such as the tetracycline-(tet-) or streptogramin-dependent transactivators (pUHD15-1 encoding the tetracycline-repressible transactivator tTA; pUHD17-1neo encoding the tetracycline-inducible reverse tTA (rtTA; Gossen et al., 1995. Science 268: 1766-1769); pMF156 encoding the streptogramin responsive transactivators (Fussenegger et al., 2000, supra.). Also ET1 did not activate SEAP expression from tet- or streptogramin-dependent promoters (pMF111; pMF172 (Fussenegger et al., 2000, supra). When CHO cells were cotransfected with plasmids encoding an erythromycin dependent transactivator (ET1, ET2, ET3, ET5, ET6, ET7) and a plasmid containing and a $P_{ETR3}$-SEAP (human placental secreted alkaline phosphatase) reporter construct (pWW38), the SEAP expression was greatly decreased when erythromycin (10 µg/ml) was present in the culture medium compared to control cultures. The corresponding SEAP-activities are shown in Table 1.

TABLE 1

Comparison of the regulation characteristics of the erythromycin-dependent transactivators ET1, ET2, ET3, ET5, ET6, ET7 in combination with the $P_{ETR3}$-SEAP reporter construct. CHO-K1 cells were simultaneously cotransfected with the plasmids indicated and the SEAP activity was measured (p-nitrophenolphosphate-based absorbance time course) in the presence and absence of erythromycin (10 µg/ml) 48 hr post transfection.

| Cell line and plasmids | SEAP activity [U/L] no inducer | SEAP activity [U/L] + Erythromycin [10 µg/ml] |
|---|---|---|
| CHO + pWW35 + pWW38 (ET1 + PETR3) | 106.4 ± 11.4 | 5.2 ± 0.5 |
| CHO + pWW42 + pWW38 (ET2 + PETR3) | 24.2 ± 1.0 | 2.5 ± 0.6 |
| CHO + pWW64 + pWW38 (ET3 + PETR3) | 13.5 ± 1.6 | 1.0 ± 0.4 |
| CHO + pBP37 + pWW38 (ET5 + PETR3) | 104.1 ± 12.4 | 12.1 ± 1.5 |
| CHO + pBP38 + pWW38 (ET6 + PETR3) | 41.2 ± 4.1 | 5.8 ± 0.5 |
| CHO + pBP39 + pWW38 (ET7 + PETR3) | 14.9 ± 1.1 | 2.3 ± 0.2 |

This experiment indicates that external erythromycin can enter mammalian cells and exert control of ET/$P_{ETR3}$-regulated gene expression there. However, erythromycin has no influence on expression levels of $P_{SV40}$ or $P_{hCMV}$-driven SEAP expression constructs (data not shown). Similar EM-dependent gene expression using the ET/$P_{ETR3}$ system has also been observed in HeLa, COS-7 and HEK-293-T cells (not shown) No deleterious effects on CHO cell morphology and growth were observed at EM concentrations of 2 µg/ml, which were found to be effective for repression of the ET/$P_{ETR3}$ system.

Stable Expression of ET1 in CHO Cells

Two representative clones, CHO-ET1$_1$ and CHO-ET1$_2$, were chosen at random among ET1-expressing CHO cell clones stably transfected with a constitutive ET1 expression construct (pWW35). Both cell lines showed no unusual cell morphologies and display similar growth behavior compared to wild-type CHO-K1 cells, indicating that sustained constitutive ET1 expression does not have obvious deleterious physiological effects on CHO cells. Transient transfection of CHO-ET1$_1$ and CHO-ET1$_2$ with a $P_{ETR3}$-SEAP expression vector (pWW38) resulted in high level SEAP expression in the absence of EM and significant repression in the presence of 2 µg/ml EM as shown in Table 2.

TABLE 2

Erythromycin (EM) dependent SEAP production of ET1-(EM-dependent transactivator) expressing stable cell lines CHO-ET1$_1$ and CHO-ET1$_2$ transiently transfected with the SEAP-encoding, EM-responsive reporter plasmid pWW38.

| Cell line and plasmid | SEAP Production (%) −EM | SEAP Production (%) +EM |
|---|---|---|
| CHO-ET1$_1$ + $P_{ETR3}$-SEAP (pWW38) | 100 | 1.75 ± 0.1 |
| CHO-ET1$_2$ + $P_{ETR3}$-SEAP (pWW38) | 100 | 4.67 ± 0.8 |

Induction factors (the ratio of SEAP activity without EM to SEAP activity with EM) reach 57 and 21 for CHO-ET1$_1$ and CHO-ET1$_2$, respectively. EM-responsive SEAP regulation of both CHO-ET1 derivatives is fully reversible following repeated cycles of addition and withdrawal of this macrolide antibiotic, indicating reversible EM-ET interaction in mammalian cells.

This characteristic is necessary to achieve fluctuating daily dosing regimes optimal for many therapeutic proteins such as insulin.

Dose-Dependence of EM-Mediated Gene Regulation in CHO Cells

Figure 4A:
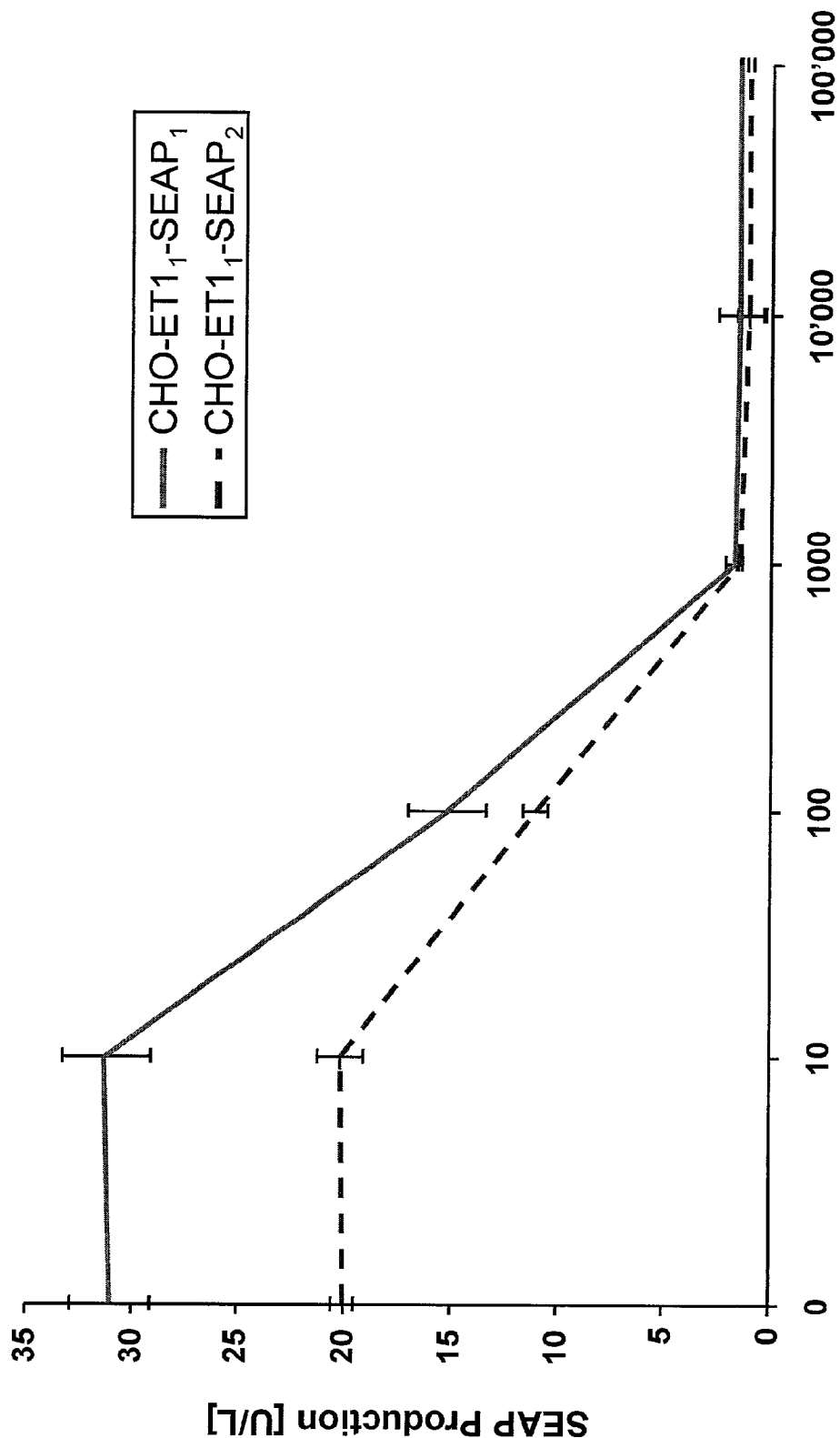
FIG. 4a: Dose-response curve for erythromycin (EM)-dependent gene expression. The cell line CHO-ET1-SEAP$_1$ was grown for 48 h at different EM concentrations (ng/ml). The relative SEAP production is shown over 5 orders of magnitude of EM concentration.

Varying the concentrations of EM used for induction could control the levels of $P_{ETR3}$-regulated gene expression. This was assessed using a stable CHO cell line (CHO-ET1$_1$-SEAP) which expresses $P_{ETR3}$-SEAP (pWW38) and stably contains also a constitutive ET1 expression vector (pWW35). FIG. 4a shows the dose-response curve for EM-dependent SEAP expression of CHO-ET1$_1$-SEAP cultures over 5 orders of magnitude of EM concentration. Beyond the concentration window of 10-1000 ng/ml, the ET1/$P_{ETR3}$ is either fully induced (<10 ng/ml) or repressed (>1000 ng/ml), while gene expression can be adjusted to different levels within this window of concentrations. Increasing EM concentration above 10 ng/ml leads to a gradual decrease in SEAP expression, with lowest SEAP expression levels at EM concentrations over 1000 ng/ml. Besides the response plateaus of the ET1/$P_{ETR3}$ system at EM concentrations below 10 ng/ml and above 1000 ng/ml, this system shows a broad window between these two concentrations in which the gene expression can be adjusted to intermediate levels. Such adjustable gene expression characteristics are particularly important for clinical applications, which require titration of circulating proteins into the therapeutic range. The effective regulating concentrations are the same as found in most tissues during antibiotic therapy.

Regulation Efficiency of Different Antibiotics

Access to alternative effective antibiotics would expand the spectrum of regulating agents available for future use in human cell and gene therapy. Accordingly, several commercially available antibiotic sources were tested for their potential to regulate the ET1/$P_{ETR3}$ system as shown below in Table 3. Among available ones, erythromycin proved to be the most efficient regulating agent, showing an induction factor of 57 followed by clarithromycin (23-fold induction).

TABLE 3

Regulation potential of different antibiotics. CHO-ET1$_1$ was transiently transfected with the SEAP-encoding plasmid pWW38 and grown for 48 h in the absence or presence of different macrolides at a concentration of 2 µg/ml.

| Antibiotic | SEAP production [%] |
|---|---|
| No macrolide | 100 ± 2.7 |
| Azithromycin | 57.6 ± 4.4 |
| Ceftriaxone | 28.8 ± 1.8 |
| Clarithromycin | 4.3 ± 0.3 |
| Erythromycin | 1.7 ± 0.1 |
| Roxithromycin | 18.1 ± 0.9 |
| Tylosin | 30.9 ± 3.2 |

Clarithromycin is very similar in structure to erythromycin, it differs only in the methylation of the hydroxyl group at position 6 on the lactone ring. The pharmacokinetic advantages of clarithromycin over erythromycin include increased oral bioavailability (52 to 55%), increased plasma concentrations (mean maximum concentrations range from 1.01 to 1.52 mg/L and to 1.52 to 2.85 mg/L after multiple 250 and 500 mg doses, respectively) and a longer half-life (3.3 to 4.9 hrs) to allow longer time intervals between two administrations. In addition, clarithromycin has extensive diffusion into saliva, sputum, lung tissue, epithelial lining fluid, alveolar macrophages, neutrophils, tonsils, nasal mucosa and middle ear fluid (Rodvold, 1999. Clin. Pharmacokinet. 37, 385-98).

Comparison and Compatibility Studies of the Erythromycin Based Gene Regulation System With the Streptogramin- and Tetracycline-based Ones in CHO Cells.

The regulation performance of the EM-based regulation system was compared directly with the widely used TET- and PIP responsive expression concepts. To this end, we have constructed a stable CHO-K1-derived cell line expressing ET1, PIT and tTA (CHO-Triplet$_{42}$). CHO-Triplet$_{42}$ showed no difference in cell morphology and specific growth rate compared to parental CHO-K1. CHO-Triplet$_{42}$ was transfected with either isogenic (i) $P_{ETR3}$-(pWW38), (ii) a $P_{PIR}$-(pristinamycin-responsive promoter, pMF172, Fussenegger et al., 2000. supra.), or (iii) a $P_{hCMV*-1}$-(tetracycline-responsive promoter, pMF111, Fussenegger et al., 2000. supra) driven SEAP expression vector to assess the individual regulation performance of the three antibiotic-responsive gene regulation systems in CHO cells (Table 5). The maximum SEAP expression levels of the TET- and the E.REX-system are in the same range whereas the maximum expression levels of the $P_{PIR}$-driven SEAP are approx. 12-fold lower (Fussenegger et al., 2000, supra) which can be explained by the different minimal promoters of these systems: The E.REX and the tet-system use the same minimal human cytomegalovirus promoter whereas $P_{PIR}$ contains the weaker minimal promoter sequence of the *Drosophila* hsp70-promoter.

To analyze the relative regulatory characteristics, we evaluated induction factors (IF; ratio of maximal expression level to antibiotic-repressed expression level). IFs have been shown to remain largely unaffected by the choice of the minimal promoter or other promoter modifications aimed at increasing the maximum expression level (No et al., 1996, supra).

The E.REX system shows an IF of 20, whereas the tet-regulated systems shows only 13-times lower expression in the presence of tet. Therefore, the ET1/$P_{ETR3}$-based mammalian gene regulation system shows superior gene inducibility characteristics than the tet-system in CHO cells engineered to provide regulation of both systems. The Pip-system showed three-fold induction factors and a low maximum expression (approx. 12-times lower than the E.REX and tet-system).

Evaluation of antibiotic crossregulation in CHO-Triplet$_{42}$ transfected separately with $P_{ETR3}$-SEAP (pWW38), $P_{PIR}$-SEAP (pMF172), and $P_{hCvM*-1}$-SEAP (pMF111) expression constructs revealed no significant interference of $P_{ETR3}$ and $P_{hCMV*-1}$ by PI (2 µg/ml) while Tet (2 µg/ml) had only a minor repressive effect. These repressive effects are still in a range which is tolerable for use in potential medical applications. Interestingly, $P_{PIR}$ showed 1.6- and $P_{hCMV*-1}$ 2.2-fold increased maximum expression levels in the presence of EM (2 µg/ml) (Table 4).

According to these data erythromycin in combination with the erythromycin-dependent transactivator ET1 increases maximum transcriptional activity from the tetracycline- and pristinamycin-responsive promoters. This opens a novel approach for increasing the maximum expression of these two systems by coexpression of ET1 and administration of EM.

TABLE 4

Triple regulation of the erythromycin-, pristinamycin-, and tetracycline-responsive promoters in CHO-Triplet$_{42}$ cells stably expressing the three transactivators ET1, PIT and tTA. Triplicate cultures of CHO-Triplet$_{42}$ were transfected with plasmids encoding SEAP under control of erythromycin- ($P_{ETR3}$; pWW38), pristinamycin- ($P_{PIR}$; pMF172 or tetracycline- ($P_{hCMV*-1}$; pMF111) responsive promoters. Transfected cultures were grown for 48 h in the presence or absence of indicated antibiotics and assayed for SEAP activity (U/L).

| | SEAP activity [U/L] | | | |
|---|---|---|---|---|
| Plasmid | no antibiotic | +EM | +PI | +Tet |
| pMF111 ($P_{hCMV*-1}$) | 88.5 ± 2.7 | 195.1 ± 15.1 | 87.9 ± 7.0 | 6.9 ± 0.6 |
| pMF172 ($P_{PIR}$) | 6.5 ± 0.4 | 10.1 ± 1.5 | 2.2 ± 0.1 | 4.6 ± 0.4 |
| pWW38 ($P_{ETR3}$) | 75.3 ± 4.1 | 3.8 ± 0.4 | 71.9 ± 7.0 | 55.0 ± 8.3 |

Figure 4B:
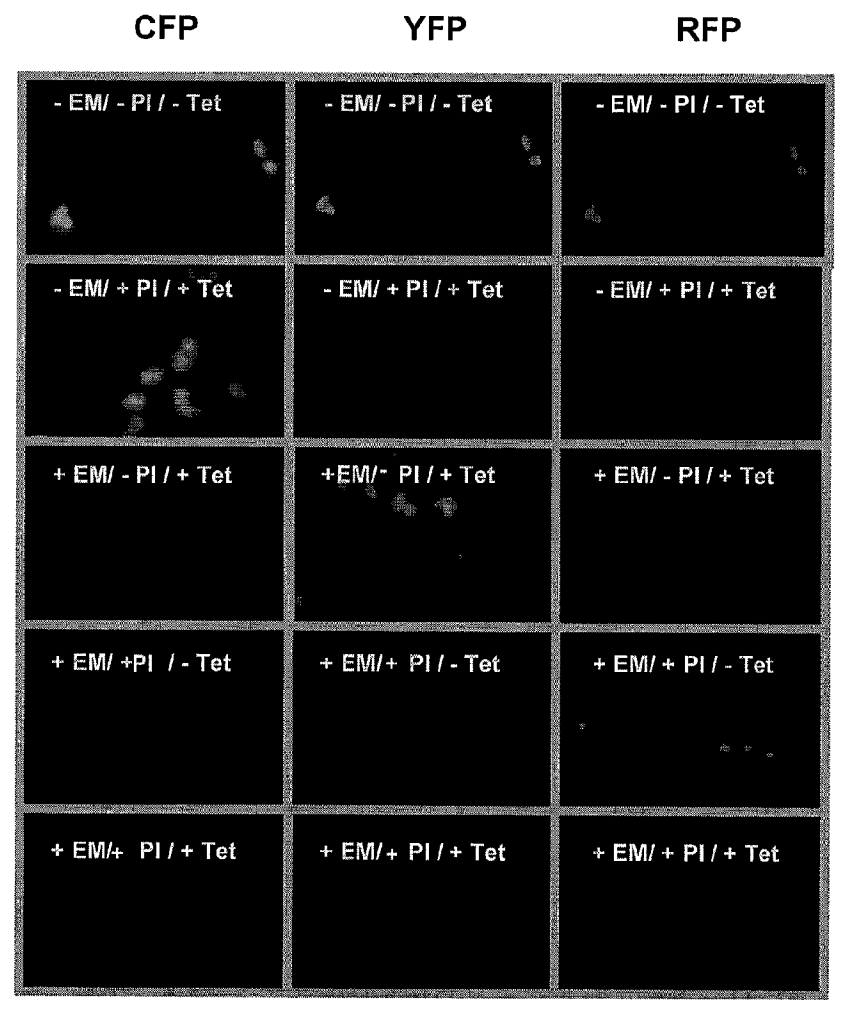

In order to demonstrate independent regulation of three transgenes in mammalian cells, we cotransfected pWW65 ($P_{hCMV*-1}$-RFP-pA$_I$-/-$P_{PIR}$-YFP-pA$_{II}$) and pWW44 ($P_{ETR3}$-CFP-PA) into CHO-Triplet$_{42}$. pWW65 contains a dual-regulated tetracycline- and streptogramin-responsive expression unit for the red (RFP) and the yellow fluorescent proteins (YFP), respectively, and pWW44 consists of $P_{ETR3}$-driven expression cassette for the cyan fluorescent protein (CFP). All three fluorescent proteins were expressed in the absence of antibiotics, and any desired expression configuration of CFP, YFP and RFP could be achieved by selective addition or omission of the appropriate antibiotics (FIG. 4b), thus demonstrating that the three antibiotic-responsive gene regulation systems $E_{OFF}$, $PIP_{OFF}$ and $TET_{OFF}$ are compatible with each other such enabling sophisticated multiregulated molecular interventions in mammalian cells.

Discussion

As demonstrated herein for the first time, molecular interactions between components evolved to provide for macrolide resistance in *Enterobacteriaceae* were successfully employed in a mammalian context for design of macrolide-repressible ($E_{OFF}$) promoters. Erythromycin-based regulated expression (E.REX), as applied in the $E_{OFF}$ (erythromycin-repressible gene expression) configuration, provided several characteristics ideally suited for human gene therapy and biopharmaceutical manufacturing: (i) low baseline expression and high induction ratio, (ii) control by a readily bioavailable, small-molecule drug showing no significant interference with host metabolism, (iii) high pharmacokinetic turnover of the regulating agent in all tissues to allow rapid reversion to the native configuration, and (iv) high modularity of regulation components to allow independent and efficient optimization of expression levels for specific therapeutic situations.

As demonstrated herein for the first time, we have engineered better erythromycin-based expression systems to achieve more efficient activation or repression of cloned genes. The development of macrolides for antibiotic therapy provides useful clinical information and derivatives. Macrolides have been chemically modified to provide improved bioavailability, pharmacokinetics and human compatibility. In addition, upon oral or intravenous administration, macrolide antibiotics reach regulation-effective concentrations throughout most of the human body. Nevertheless, macrolide antibiotics are rapidly eliminated from the blood and most tissues, with half-lives typically not exceeding four hours in humans, allowing for reversibility of possible therapeutic conditions. An entire set of clinically licensed 14-membered macrolides is available for adjusting E.REX technology, many of which have a proven track record as antibiotics or immunomodulatory agents for over half a century, such as erythromycin, clarithromycin and roxtriaxone (Williams et al., 1993. J. Antimicrob. Chemother. 31(Suppl. C), 11-26).

An important characteristic of the E.REX system is its functional compatibility with the most widely used pristinamycin and tetracycline regulation strategy. The combination of the E-, Pip- and Tet-based regulation concepts enabled independent control of three different gene activities by three different antibiotics in the same cell, which offers greater regulation flexibility compared to the recently described doxycycline inducible/repressible regulation concept (Baron et al., (1999) Proc. Natl. Acad. Sci. USA 96, 1013-1018) or to the powerful dual PIP- and Tet-based technology (Fux et al., 2001. Nucleic Acids Res. 29, e19). The availability of a third system for gene regulation extends the potential for multigene-based reprogramming of key regulatory networks of mammalian cells and thus opens new possibilities for multigene metabolic engineering as well as for the design of sophisticated gene-based therapies and tissue engineering strategies.

A mammalian gene regulation system such as the ET1/$P_{ETR3}$ configuration which responds to a class of chemically related antibiotics offers another powerful new dimension: finding new antibiotics which are urgently needed to cope with increasing prevalence of multidrug resistant bacterial pathogens. Metabolic libraries from a great variety of microorganisms like fungi could be screened using cultured mammalian cells containing the ET/$P_{ETR}$ system linked to a reporter gene to identify novel macrolides. This technology is at least one order of magnitude more sensitive than classical microbial inhibition tests and not biased by antibiotic resistance of indicator bacteria (see example 6).

Example 2

The Dual Regulation System

Most of today's gene therapy and tissue engineering strategies focus on stable integration of transgenes into human somatic cells either in vivo or ex vivo. While initial success was achieved using sophisticated gene transfer technology including attenuated viruses, site-specific recombination for targeted integration and non-immunogenic selection markers, gene transfer is not the only challenge in future gene therapy and tissue engineering. However, the success and realization of this technology will largely be dependent on flanking concepts which allow ex vivo expansion of grafted tissue followed by sustained growth control and reimplantation of treated cells or tissues. This concept requires two consecutive steps of opposite proliferation control which enables first expression of genes which activate proliferation for ex vivo expansion of tissue cells followed then by gene therapeutic operation and activation of proliferation control to allow reimplantation of genetically engineered tissue.

Using two human-compatible gene regulation systems, the macrolide- and the tetracycline-system we set out to construct a double regulation system to achieve completely externally controlled proliferation management of mammalian cells.

Materials and Methods

In order to establish a dual-regulated expression vector for independent control of two genes by tetracycline- and erythromycin-responsive promoters, pDuoRex9 was constructed which encodes for YFP (yellow fluorescent protein) and CFP (cyan fluorescent protein) under control of the erythromycin- and tetracycline-dependent promoters $P_{ETR1}$ (example 3) and $P_{hCMV*-1}$, respectively. For complete proliferation management a vector was constructed allowing expression of the cell cycle arrest gene $p27$ under control of the tetracycline-dependent promoter, whereas p27 can be expressed in antisense under control of the erythromycin-responsive regulation system.

Vector Construction pDuoRex9 (pWW94) contains converging erythromycin- and tetracycline-responsive expression units and was constructed following a multiple step cloning procedure:

a) pWW92 was constructed by excising (EcoRI/NotI) the EYFP-pA* containing cassette from pSAM222 (Fux et al., 2001. Nucleic Acids Res. 29: e19) and ligation into the corresponding sites (EcoRI/NotI) of pWW36 (see example 3) thereby replacing SEAP of pWW36. b) The $P_{ETR1}$-EYFP-pA* cassette was excised with SspI/NotI from pWW92 and ligated into the corresponding sites of pTRIDENT1 (pMF125, Fussenegger et al., 1998. Nat. Biotechnol. 16, 468-472), hence replacing $P_{hCMV*-1}$ and IRESI of pTRIDENT1 to give plasmid pWW93. c) The ECFP-pA* containing cassette was released from pSAM227 (Fux et al., 2001. Nucleic Acids Res., 29:e19) by digestion with XhoI and SrfI and was subsequently ligated to pWW93 restricted with SalI (compatible to XhoI) and SrfI to result in plasmid pDuoRex9 (FIG. 5, pWW94: $P_{ETR1}$-YFP-pA$_I$-pA$_{II}$-CFP-$P_{hCMV*-1}$).

Figure 5A:
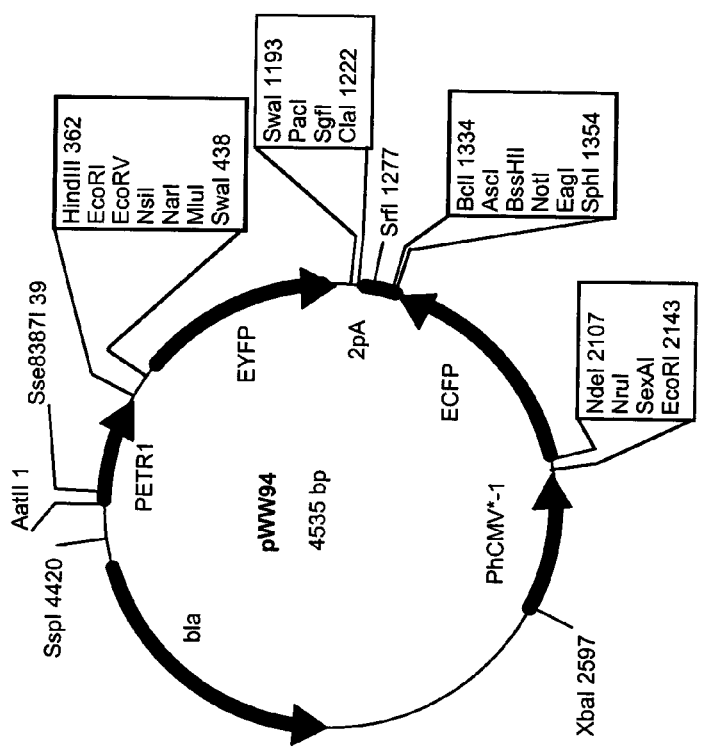
FIGS. 5a and 5b: Dual regulated expression vectors: pWW94 encodes for the yellow fluorescent protein (YFP) under control of the macrolide-responsive gene regulation system whereas expression of the cyan fluorescent protein (CFP) is controlled by the tetracycline-responsive promoter (FIG. 5a). PWW95 encodes for the cyclin-dependent kinase inhibitor p27$^{kiP1}$ which can be expressed either in antisense orientation (erythromycin-responsive promoter) or in sense orientation (tetracycline-responsive expression) for proliferation control of mammalian cell (FIG. 5b).
Figure 5B:
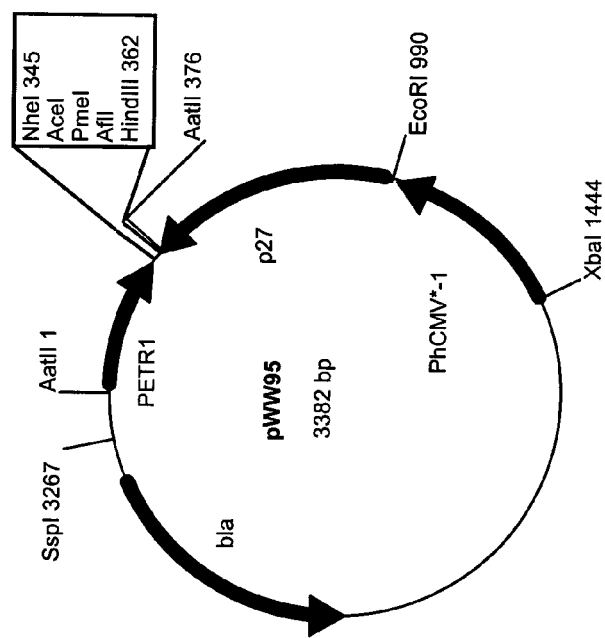
Figure 6A:
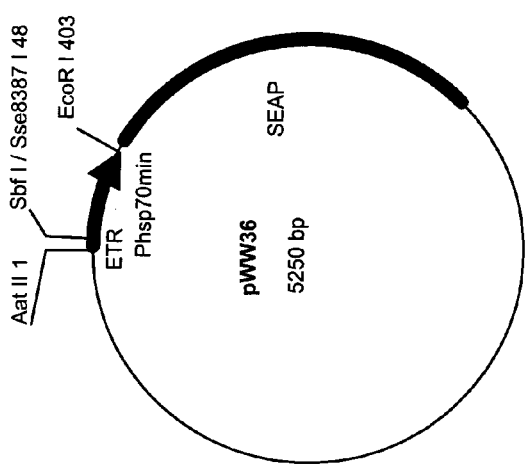
FIGS. 6a and 6b: Graphical representation of vectors pWW36 (FIG. 6a) and pWW39 (FIG. 6b). These vectors contain ETR-sequences functionally linked to the Drosophila minimum hsp70-promoter Phsp70min and the SEAP reporter gene (human placental secreted alkaline phosphatase). pWW39 contains two tandem repetitions of ETR for binding of two ETR-binding proteins.
Figure 6B:
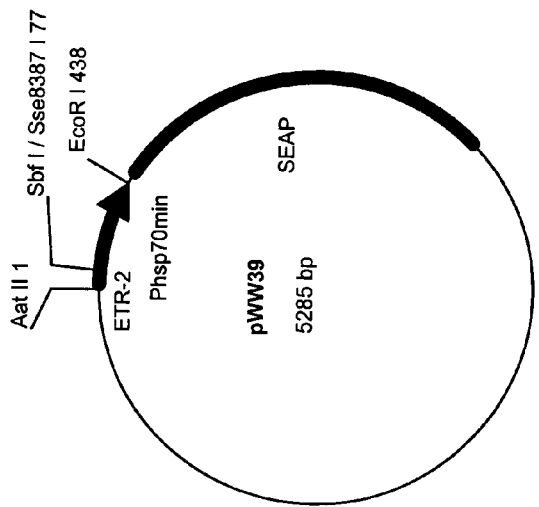

For the construction of $p27^{Kip1}$ sense-antisense expression vector pWW95, the ECFP-EYFP cassette was excised from pWW94 (pDuoRex9) by EcoRI/HindIII and replaced by the EcoRI/HindIII fragment of pMF99 (Fussenegger et al., 1997. Biotechnol. Bioeng. 55, 927-939) which encodes the cyclin-dependent kinase inhibitor. pWW95 contains a $P_{ETR1} \rightarrow p27^{Kip1} \leftarrow P_{hCMV*-1}$ sense-antisense expression unit (FIG. 5).

Results

Construction of Tetracycline- and Erythromycin-responsive Double Regulation Vectors In order to demonstrate the double regulation concept pDuoRex9 (pWW94, FIG. 5) was constructed combining tetracycline-responsive CFP and erythromycin-responsive YFP expression in a single double regulated expression unit: $P_{ETR1}$-YFP-pA$_I$-pA$_{II}$-CFP-$P_{hCMV*-1}$ ($P_{ETR1}$, see example 3). When these double regulation vectors were transiently transfected into CHO-Triplet$_{42}$-cells, independent on/off-regulation was observed in response to the respective regulating antibiotics tetracycline and erythromycin as monitored by fluorescence microscopy.

Having proofed this dual regulation concept we performed a scenario for novel gene therapy and tissue engineering concepts requiring positive and negative proliferation control We constructed pWW95 (FIG. 5), which allows sense and antisense expression of the p27 cyclin-dependent kinase inhibitor in response to the regulating antibiotics erythromycin and tetracycline, respectively. After transfection of plasmids with regulated expression of sense and antisense p27 in CHO cells expressing the corresponding transactivators, complete growth control could be achieved: expression of sense p27 leads to complete growth arrest of CHO-cells in G1-phase, whereas expression of antisense p27 induces increased specific growth rates, probably due to inhibition of endogenous p27 synthesis by expression of antisense mRNA (our data not shown, Fux et al., 2001. Nucleic Acids Res. 29: e19).

Example 3

Promoter Modification to Enhance Maximal Regulation Performance from the Macrolide-responsive System In principle, every part of the ET I/$P_{ETR3}$ system can be improved individually or exchanged by a more powerful component: (1) The MphR(A) domain of the ETs can be subjected to random mutagenesis to alter DNA binding affinity or specificity, to improve affinity to erythromycin or other macrolides or antibiotics or to reverse macrolide responsiveness of the ET/$P_{ETR3}$ system (reverse ET/$P_{ETR3}$-system), for example allow induction of gene expression upon addition of erythromycin instead of its withdrawal. (2) The VP16 domain could be exchanged by other transactivation domains such as the p65 domain of human NF-κ B (Schmitz and Baeuerle, 1991, EMBO J. 10: 3805-3817) or the E2F4 transactivation domain (see example 1) to "humanize" the regulation system and reduce immune recognition of ET or the KRAB silencing domain of the human kox1 gene (Deuschle et al., 1995, Mol. Cell Biol. 15: 1907-1914) to construct a reverse ET/$P_{ETR}$ system (see example 4). (3) The minimal promoter can be improved by introducing mutations with the aim of increasing maximum expression levels or with reducing the basal expression (leakyness) as shown in this example. (4) exchange of the minimal cytomegalovirus promoter by other minimal promoters such as the promoter of the adenoviral E1B gene or the minimal *Drosophila* hsp70 promoter as shown in this example.

Therefore the promoters $P_{ETR1}$ and $P_{ETR4}$, $P_{ETR2}$, $P_{ETR7}$, $P_{ETR8}$, $P_{ETR9}$, $P_{ETR10}$ and $P_{ETR11}$ were constructed: $P_{ETR1}$ and $P_{ETR4}$ contain one and two ETR binding motifs in 5' of the minimal *Drosophila* hsp70 promoter, respectively. The duplication of the ETR-sequence should results in higher maximum expression due to multiple binding of transactivation domains. $P_{ETR2}$ and $P_{ETR7}$-$P_{ETR11}$ contain one ETR binding motif followed by a spacer in 5' of the minimal human cytomegalovirus promoter. The lengths of the spacer segments are 0, 2, 4, 6, 8, 10 bp for $P_{ETR2}$, $P_{ETR7}$, $P_{ETR8}$, $P_{ETR9}$, $P_{ETR10}$ and $P_{ETR11}$, respectively. These spacers of different length were introduced to examine the effect of different sterical positions of the transactivation-domain to the minimal promoter.

The promoters $P_{ETR1}$ and $P_{ETR4}$ were constructed by amplification of the minimal hsp70 promoter of pTrident7 (Fussenegger et al., 1998. Biotechnol. Bioeng. 57, 1-10) with oligos OWW20: 5'-GATCGACGTCGAT-TGAATATAACCGACGTGACTGTTACATT-TAGGCCTGCAGGgagtaccctcgaccgccgg-3' (SEQ ID NO 18) and OMF57 (Fussenegger et al., 2000. supra) ($P_{ETR1}$) and oligos OWW24: 5'-GATCGACGTCGAT-TGAATATAACCGACGTGACTGTTACATT-TAGGGATTGAATATAACCGACGTGACT-GTTACATTTAGGCCTGCAGGgagtaccctcgaccgccgg-3' (SEQ ID NO 19) and OMF57 ($P_{ETR4}$) and subsequent ligation (AatII/EcoRI) into the corresponding sites of pMF111 (Fussenegger et al., 2000. supra) thus resulting in $P_{ETR1}$-SEAP (ETR-$P_{hsp70min}$-SEAP, pWW36) and $P_{ETR4}$-SEAP (ETR$_2$-$P_{hsp70min}$-SEAP, pWW39), respectively.

$P_{ETR2}$, $P_{ETR7}$-$P_{ETR11}$ were constructed by amplifying the minimal human cytomegalovirus promoter from pRevTRE (Clontech) with the oligos listed below:

$P_{ETR2}$: OWW21: GATCGACGTCGATTGAATATAAC-CGACGTGACTGTTACATTTAGGCCTG-CAGGtcgagctcggtacccgggtc (SEQ ID NO 20) and OWW22 (SEQ ID 16, supra).

$P_{ETR7}$: OBK1: gcctgcaggATtcgagctcggtacccgggtc (SEQ ID NO 21) and OWW22 (SEQ ID 16, supra).

$P_{ETR8}$: OBK2: gcctgcaggATCGtcgagctcggtacccgggtc (SEQ ID NO 22) and OWW22 (SEQ ID 16, supra).

$P_{ETR9}$: OBK3: gcctgcaggATCGTAtcgagctcggtacccgggtc (SEQ ID NO 23) and OWW22 (SEQ ID 16, supra).

$P_{ETR10}$: OBK4: gcctgcaggATCGTAATtcgagctcgg-tacccgggtc (SEQ ID NO 24) and OWW22 (SEQ ID 16, supra).

$P_{ETR11}$: OBK5: gcctgcaggATCGTAATCGtcgagctcg-gtacccgggtc (SEQ ID NO 25) and OWW22 (SEQ ID 16, supra).

The $P_{ETR2}$-containing PCR fragment was cloned (AatII/EcoRI) into the corresponding sites of pMF111 (Fussenegger et al., 2000, supra) thus resulting in plasmid pWW37 (FIG. 3) encoding SEAP under control of $P_{ETR2}$. The PCR fragments containing $P_{ETR7}$-$P_{ETR11}$ were subsequently cloned (Sse8387I/EcoRI) into the corresponding sites (Sse8387I/EcoRI) of pWW36 (above) thus resulting in plasmids pBP10-pBP14 (FIG. 3) which encode SEAP under control of the different promoters: $P_{ETR7}$-SEAP: pBP10, $P_{ETR8}$-SEAP: pBP11, $P_{ETR9}$-SEAP: pBP12, $P_{ETR10}$-SEAP: pBP13, $P_{ETR11}$-SEAP: pBP14.

To analyze the regulatory performance of promoters $P_{ETR1}$ and $P_{ETR4}$, an ET1-encoding vector (pWW35) was cotransfected with pWW36 and pWW39 into CHO-K1 cells. The cells were cultured in the absence and presence of erythromycin (10 µg/ml) and SEAP activity was measured after 48 hrs. The results are shown in Table 6 together with the values of an ET1/$P_{ETR3}$ transfection (Table 5) for better comparison.

TABLE 5

Comparison of different erythromycin-responsive promoters. Triplicate cultures of CHO-K1 cells were cotransfected with the indicated plasmids. Transfected cultures were grown in the presence or absence of erythromycin (10 µg/ml) for 48 hrs before measuring SEAP activity.

| Cell line and plasmids | SEAP activity [U/L] | |
|---|---|---|
| | −Erythromycin | +Erythromycin [10 µg/ml] |
| CHO + pWW35 + pWW38 (ET1 + $P_{ETR3}$-SEAP) | 106.4 ± 11.4 | 5.2 ± 0.5 |
| CHO + pWW35 + pWW36 (ET1 + $P_{ETR1}$-SEAP) | 44.7 ± 3.0 | 5.3 ± 0.6 |
| CHO + pWW35 + pWW39 (ET1 + $P_{ETR4}$-SEAP) | 179.4 ± 9.6 | 29.3 ± 0.6 |

$P_{ETR1}$- and $P_{ETR3}$-driven SEAP constructs show the same low basal expression, whereas the maximum expression of the $P_{ETR1}$-driven construct was approx. twofold lower. Therefore this construct is suitable in a context where low basal expression is needed but where also high expression levels could show deleterious effects. This could be the case in mammalian cell reprogramming tasks, where too strong overexpression of regulatory genes leads to undesired side-effects. The $P_{ETR4}$-driven SEAP construct showed the highest expression, probably due to the double ETR binding motif, which leads to the recruitment of more transactivation domains. Therefore this configuration is promising in recombinant protein expression, where strong promoters are requested for high yield production.

The effect of the different spacer length in promoters $P_{ETR2}$ and $P_{ETR7}$-$P_{ETR11}$ were examined by transfecting the corresponding plasmids (pWW37, pBP10-pBP14) into a CHO cell line stably transfected with the transactivator ET1 (MphR(A)-VP 16, see example 1). The cells were cultured for 48 h in the presence and absence of erythromycin (2 µg/ml) before assaying SEAP activity (Table 6).

TABLE 6

Regulation characteristics of different erythromycin-repressible promoters. These data show the effect of spacer fragments between the minimal promoter and the ETR-binding site on maximum expression as well as on the leakyness of the system (basal expression in repressed state).

| Plasmid (Promoter, spacer) | SEAP activity [U/L] + EM | SEAP activity [U/L] − EM |
|---|---|---|
| pWW37 ($P_{ETR2}$, 0 bp) | 8.3 ± 0.2 | 252.2 ± 50.9 |
| pBP10 ($P_{ETR7}$, 2 bp) | 4.2 ± 1.0 | 94.0 ± 18.9 |
| pBP11 ($P_{ETR8}$, 4 bp) | 11.6 ± 2.6 | 295.8 ± 43.0 |
| pBP12 ($P_{ETR9}$, 6 bp) | 8.4 ± 1.6 | 219.8 ± 2.2 |
| pBP13 ($P_{ETR10}$, 8 bp) | 19.7 ± 1.4 | 278.3 ± 50.2 |
| pBP14 ($P_{ETR11}$, 10 bp) | 12.5 ± 0.8 | 272.4 ± 23.5 |

It can be seen that the maximum expression of all constructs is more or less the same (except for pBP10), but that the basal expression in the repressed state varies significantly. Depending on the requirements for a specific application the optimal promoter can therefore be chosen, giving rise to high maximum expression or to drastically reduced leakyness in the repressed state.

Example 4

Construction of an Erythromycin-inducible Expression System With Enhanced Regulation Characteristics The classical ET/$P_{ETR}$ system belongs to the "OFF" family of regulation concepts since gene expression is activated upon withdrawal of the regulating antibiotic. However, in some applications such as gene therapy and tissue engineering an "ON" system that is induced upon addition of macrolide antibiotics is more desirable. We therefore constructed a new MphR(A)-based binary EON system which consists of a $P_{ETR}$ON promoter and a set of two different transrepressors. Two different $P_{ETR}$ON promoters were constructed: $P_{ETR}$ON4 consists of an ETR4 (four tandem repetitions of ETR, SEQ ID NO 26) placed downstream of the strong viral SV40 promoter. $P_{ETR}$ON8 contains eight tandem repetitions (SEQ ID NO 27) of ETR instead of four.

Transrepressors such as ET4 (SEQ ID NO 10, example 1, FIG. 2), which consists of a protein fusion between MphR(A) and the KRAB silencing domain of the human kox-1 gene (Deuschle et al., 1995, Mol. Cell Biol. 15: 1907-1914) or MphR(A) alone, bind to ETR in front of $P_{SV40}$ and block transcription of this promoter. Besides sterical transcription blocking, the silencing domain of ET4 can additionally downregulate $P_{SV40}$ activity.

Materials and Methods

Figure 7:
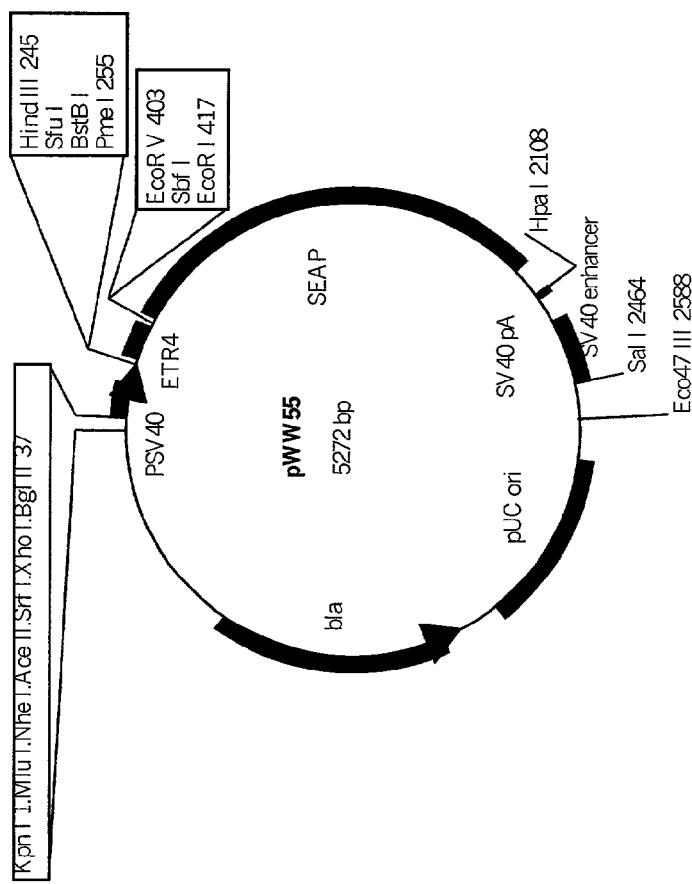
FIG. 7: Graphical representation of the EON expression vectors pWW55. This vector contains four (ETR4, pWW55) tandem repetitions of ETR in 3' of the constitutive SV40 promoter ($P_{ETR}$ON4). Plasmid pWW56 carrying the $P_{ETR}$ON8-promoter is based on pWW55 and contains eight (ETR8, pWW56) ETR tandem repetitions instead of four (not shown).

The ETR4 sequence (SEQ ID NO: 26) was excised from the WEBE Gene vector (custom synthesized by Operon Technologies Inc.) by SfuI and EcoRI and ligated into the corresponding sites of pMF208 (Fussenegger et al., 2000. supra) thus resulting in plasmid pWW55 (FIG. 7) containing the $P_{SV40}$-ETR4-SEAP cassette. The combination of $P_{SV40}$ and ETR4 is designated $P_{ETR}$ON4. For construction of $P_{ETR}$ON8, ETR4 was excised (PmeI/EcoRI) from pWW55 and cloned into pWW55 restricted with (EcoRV/EcoRI) thus resulting in SV40-ETR8-SEAP (pWW56).

Sequence of ETR4 as contained in the WEBE Gene vector (Operon Technologies, the four tandem repetitions of ETR are marked in upper case, one ETR-motif in italics. The lower case sequences contain restriction sites. SEQ ID NO 26):

gacgtcttcgaagtttaaacGAT-
TGAATATAACCGACGTGACTGTTACATT-
TAGGGATTGA ATATAACCGACGTGACTGTTACATT-
TAGGGATTGAATATAACCGACGTGACTGTTAC
ATTTAGGGATTGAATATAACCGACGT-
GACTGTTACATTTAGGgatatcctgcagggaattc Sequence of ETR8 as present in pWW56, fusion product of two ETR4 sequences (Tandem repetitions in upper case, linker between the two ETR4-sequences in lower case. SEQ ID NO 27):

GATTGAATATAACCGACGTGACTGTTACATTTAGGGATTGAATATAACCG

ACGTGACTGTTACATTTAGGGATTGAATATAACCGACGTGACTGTTACAT

TTAGGGATTGAATATAACCGACGTGACTGTTACATTTAGGgataaacGAT

TGAATATAACCGACGTGACTGTTACATTTAGGGATTGAATATAACCGACG

TGACTGTTACATTTAGGGATTGAATATAACCGACGTGACTGTTACATTTA

GGGATTGAATATAACCGACGTGACTGTTACATTTAGG.

ET4, the MphR(A)-KRAB fusion protein was constructed as described in example 1 (SEQ ID NO 10). For expression of MphR(A) pWW29 (SEQ ID NO 4) was used. The stop codon of the original MphR(A) has been mutated in order to allow fusion to the various transactivating and transrepressing domains. Because of the mutation of this stop codon the mphR(A) gene contained in pWW29 is terminated a few bp downstream at the next stop codon encountered in the vector sequence. However, the resulting MphR(A) protein preserves its role as transcriptional repressor in the EON configuration.

Results

Regulation Characteristics of the $E_{ON}$ System

The regulation performance of $P_{ETR}$ON4 ($P_{SV40}$-ETR4-SEAP-pA; pWW55) and $P_{ETR}$ON8 ($P_{SV40}$-ETR8-SEAP-pA; pWW56) was assessed in CHO-K1 cells harboring the MphR(A) expression vector pWW29 ($P_{EF1\alpha}$-E-pA) (Table 7).

In order to further enhance its repressing activity, MphR (A) was fused to the transsilencing domain (KRAB) of the human kox1 gene. The resulting transrepressor ET4 (E-KRAB; pWW43, $P_{hCMV}$-ET4-pA) showed 25-fold lower basal expression from $P_{ETR}$ON4 compared to the isogenic MphR(A)/$P_{ETR}$ON4 configuration (Table 7).

The induction factors (expression in induced state to expression in repressed state) are in the range of 5 for both, $P_{ETR}$-ON4 and $P_{ETR}$-ON8 when repressed by MphR(A). This factor is increased for both promoters by using ET4 as transrepressor, which results in almost complete suppression of transcriptional activity. The difference in their regulation characteristics enables the use of the four tested EON configurations for a broad range of different applications. In configurations which require high expression levels the use of the MphR(A)/$P_{ETR}$ON4 configuration is advantageous whereas situations which require tightest repression of basal expression of the transgene, the ET4/$P_{ETR}$ON4/8 concept is the preferred system.

The modular setup of $P_{ETR}$ON consisting of an independent operator sequence (ETR4 or ETR8) and a fully functional promoter element allows straightforward exchange of $P_{SV40}$ of $P_{PIR}$ON by any type of promoter to enable, for example, tissue-specific regulated expression or adaptation of this inducible regulation concept to other organisms such as yeast, insects and plants.

TABLE 7

Regulation characteristics of the erythromycin-regulated expression system. CHO-K1 cells were transiently cotransfected in triplicate (i) with a SEAP expression vector driven by the indicated promoter and (ii) with a transrepressor-encoding vector. After culturing for 48 hrs. in the absence or presence of erythromycin (2 µg/ml) SEAP activity was measured.

| | | SEAP activity [U/L] | |
|---|---|---|---|
| Promoter | Transrepressor | −Erythromycin | +Erythromycin [2 µg/L] |
| $P_{ETR}$-ON4 | MphR(A) | 36.0 ± 2.4 | 175.7 ± 6.2 |
| $P_{ETR}$-ON4 | ET4 | 1.4 ± 0.04 | 35.7 ± 4.7 |
| $P_{ETR}$-ON8 | MphR(A) | 16.5 ± 1.9 | 81.6 ± 4.3 |
| $P_{ETR}$-ON8 | ET4 | 2.2 ± 0.4 | 55.4 ± 1.8 |

Example 5

Construction of Multi-Purpose Expression Vectors

In order to use the erythromycin-responsive mammalian gene regulation system in a wide variety of applications, a set of 6 mammalian gene expression vectors which are compatible with the use of all erythromycin-dependent transactivators (ET1, ET2, ET3, ET5, ET6, ET7) and transrepressors (MphR(A), ET4) was constructed. The first set of vectors, pWW71 and pWW72, consists of monocistronic expression vectors containing the $P_{ETR1}$ (pWW71) and $P_{ETR}$ON8 (pWW72) promoters followed by a multiple cloning site of up to 22 unique restriction sites 6 of which are rare-cutting sites for enzymes recognizing 8 bp (FIG. 8a).

The second set of vectors is shown in FIG. 8b and contains the same promoters $P_{ETR3}$ and $P_{ETR}$ON8 integrated in the pTRIDENT family of tricistronic expression vectors (Fussenegger et al. 1998, Biotechnol. Bioeng. 57,1-10). pTRIDENT vectors contain a single tricistronic expression unit which is driven either by $P_{ETR3}$ (pTRIDENT20, pWW73 and pTRIDENT21, pWW74) or $P_{ETR}$ON8 (pTRIDENT22, pWW75 and pTRIDENT 23, pWW76). While the first cistron is translated in the classical cap-dependent manner, the following two cistrons rely on cap-independent translation initiation mediated by internal ribosome binding sites of the encephalomyocarditis virus or of poliovirol origin (IRES). While pTRIDENT20 (pWW73, $P_{ETR3}$) and pTRIDENT22 (pWW75, $P_{ETR}$ON8) contain two IRES elements, pTRIDENT21 (pWW74, $P_{ETR3}$) and pTRIDENT23 (pWW76, $P_{ETR}$ON8) contain an IRES as well as a CITE element. Both IRES elements are among the strongest currently available, showing high translation initiation in a wide variety of mammalian cells and tissues (Borman et al., 1997. Virology 273:129-136; Fussenegger et al., 1998, Biotechnol. Bioeng. 57,1-10, Fussenegger et al., 1998, Nat. Biotechnol. 16,468-472). Both IRES elements are flanked by large polylinkers which allow convenient movement of genes into pTRIDENT derivatives. pTRIDENT vectors have proven to be useful tools for a wide variety of applications (Fussenegger et al., 1998, Biotechnol. Bioeng. 57,1-10; Fussenegger et al., 1998, Nat. Biotechnol. 16, 468-472)

Construction of Multi-Purpose Expression Vectors pWW71 was constructed by excising the ETR-containing SspI/Sse8387I fragment from pWW36 and ligation of this fragment into the corresponding sites (SspI/Sse8387I) of pMF189 (Disclosed in PCT application no. 00/65080) thereby replacing the PIR binding motif and resulting in $P_{ETR1}$ followed by a large multiple cloning site (FIG. 8a).

Construction of pWW72: Eight tandem repetitions of ETR (ETR8) were excised from pWW56 (HindIII/EcoRI) and ligated into pMF229 (Disclosed in PCT application no. 00/65080) (HindIII/EcoRI) thereby replacing the trimeric PIR3 binding motif.

For construction of the tricistronic pTRIDENT expression vectors (FIG. 8b) the $P_{ETR3}$ promoter was excised from pWW38 by SspI/EcoRI and the $P_{ETR}$ON8 promoter was excised from pWW72 by SspI/EcoRI.

The $P_{ETR3}$ promoter elements were subsequently cloned:
1. into the SspI/EcoRI sites of pTRIDENT1 to replace $P_{hCVM*-1}$ and result in pTRIDENT20 (pWW73, $P_{ETR3}$-MCSI-IRESI-MCSIII-IRESII-MCSIII-pA).
2. into the SspI/EcoRI sites of pTRIDENT3 to replace $P_{hCVM*-1}$ and result in pTRIDENT21 (pWW74, $P_{ETR3}$-MCSI-IRES-MCSII-CITE-MCSIII-pA).

The $P_{ETR}$ON8 promoter elements were subsequently cloned:
1. into the SspI/EcoRI sites of pTRIDENT1 to replace $P_{hCVM*-1}$ and result in pTRIDENT22 (pWW75, $P_{ETR}$ON8-MCSI-IRESI-MCSII-IRESII-MCSIII-pA).
2. into the SspI/EcoRI sites of pTRIDENT3 to replace $P_{hCVM*-1}$ and result in pTRIDENT23 (pWW76, $P_{ETR}$ON8-MCSI-IRES-MCSII-CITE-MCSIII-pA).

Construction of the Positive Feedback Regulation System Using the Macrolide-Responsive Regulation Concept In contrast to the classical ET/$P_{ETR}$ system in which an ET and $P_{ETR}$ reside on different plasmids, the positive feedback regulation concept places both elements in a single, often multicistronic, expression unit. In particular, the transactivator ET is placed under control of its target promoter $P_{ETR}$ (FIG. 8c).

In this configuration initial transcripts originating from the leakiness of the $P_{ETR}$ promoter lead to few ET molecules which are inactivated in the presence of macrolides.

However, in the absence of this class of antibiotics initial ET molecules can bind to and induce $P_{ETR}$. Since an ET transcript is produced in every round of transcription, a principle called positive feedback, ET accumulates in the cell and ensures high-level expression of the transgene of interest, yet this system retains full regulatability. Advantages of the positive feedback regulation system over classical binary regulated expression systems are:

1. Tighter repression of gene expression since ET is not expressed constitutively but originates from rare leaky transcripts. Therefore, in the repressed situation (in the presence of macrolides) little ET is present in the cell which initiate transcription from $P_{ETR}$ in contrast to the situation in which ET is constitutively expressed from a separate vector.
2. The positive feedback system produces an ET molecule in every round of transcription leading to higher intracellular ET levels and therefore also higher expression of the transgene of interest.
3. The positive feedback regulation concept establishes regulated gene expression in a single step. The classical binary ET/$P_{ETR}$ expression systems requires first installation of ET and then installation of the $P_{ETR}$-responsive gene. Two subsequent rounds of transfection and selection is not only tedious and time consuming but also undesired for advanced future therapies such as tissue engineering and gene therapy since the genome is changed significantly more than in a one-step engineering approach.

These positive feedback regulation vectors that were constructed contain both the cyan fluorescent protein CFP and ET1 in a dicistronic, $P_{ETR3}$-driven configuration. When pWW46 ($P_{ETR3}$-CFP-IRES-ET1-pA, FIG. 8c) was transfected in CHO-K1, HeLa, COS-7 or HEK 293-T cells bright cyan fluorescence could be observed by fluorescence microscopy in the absence of erythromycin whereas CFP-expression was completely repressed in the presence of erythromycin (2 µg/ml).

Also constructed was pTRIDENT-ET1 (pWW78), which contains the erythromycin-dependent transactivator ET1 in the first cistron of pTRIDENT20 (pWW73). Cistrons 2 and 3 of pTRIDENT-ET1 could accommodate two different genes of interest. Therefore, pTRIDENT-ET1 derivatives enable one-step installation of macrolide-responsive expression of up to two independent genes (FIG. 8c).

Construction of the Positive Feedback Regulation Vectors

For construction of the auto-regulated CFP expression vector pWW46, CFP was excised from pTFT2 (Moser et al., 2000. Biotechnol. Prog. 16, 724-735) by EcoRI and HindIII and cloned into the corresponding sites of pWW38 resulting in pWW44. The SspI/NotI fragment of pWW35 (containing ET1) was fused to the $P_{ETR3}$-CFP-IRES containing SspI/NotI fragment excised from pWW44 containing a $P_{ETR3}$-CFP expression unit, resulting in pWW46.

For construction of pTRIDENT-ET1, ET1 was excised from pWW35 (EcoRI/HinDIII) and ligated into pMF168 (EcoRI/HinDIII) thereby replacing PIT and resulting in ET1 under control of $P_{hCMV^*-1}$ (pWW77). Then $P_{ETR3}$ was excised from pWW38 by SspI/EcoRI and ligated into pWW77 (SspI/EcoRI) thereby replacing $P_{hCMV^*-1}$ and resulting in the autoregulated pTRIDENT-ET1 (pWW78).

Example 6

Detection of Novel Antibiotic Activities Using the Macrolide-responsive Expression Technology Erythromycin (EM), the prototype of macrolide antibiotics, has been successfully used for over half a century as broad-spectrum antibiotic against Gram-positive and a few Gram-negative human pathogenic bacteria including Helicobacter, Bordetella and Legionella pp 22. (Williams and Sefton, 1993. J Antimicrob. Chemother. 31(Suppl. C): 11-26; Labro and Abdelghaffar, 2001. J. Chemother. 13: 3-8) In addition, erythromycin-derived 14-membered macrolides show immunomodulatory activities. In recent years numerous macrolide-based antibiotics have been synthesized by creating derivatives of erythromycin showing better bioavailability as well as improved bacteriostatic and bactericidal effects on antibiotic resistant bacteria.

Macrolide antibiotics have extensively been used for growth promotion of food animals. This intensive antibiotic application lead to a drastic increase in antibiotic resistant pathogens (up to 80% of Enterococcae in pigs were resistant to erythromycin, Aarestrup et al., 2001. Antimicrob. Agents Chemother. 45: 2054-2059) in environment presenting a major problem in human antibiotic therapy (Jensen and Aarestrup, 2001. Antimicrob. Agents Chemother. 45: 371-372; Aarestrup et al., 2000. Diag. Microb. Infect. Dis. 37: 127-137). For this reason many antibiotics have recently been banned in the European Union for use in food animals, like the macrolide antibiotics spiramycin and tylosin (Aarestrup et al., 2001. Antimicrob. Agents Chemother. 45: 2054-2059). This ubiquitous antibiotic resistance in combination with the recent ban of antibiotic-use in animals implies two challenges for analytic science: a) screening systems must be set up for the discovery of novel antibiotic compounds, preferably in a high-throughput screening format, to obtain new weapons against resistant pathogens and b) to impose the antibiotic-ban, simple and cheap analytical methods are a prerequisite for effective control of antibiotic residues in meat and milk by regulating authorities.

For streptogramin antibiotics, which have partly been banned from use in animals, such an analytical system has been developed recently (PCT application no. 00/65080 and Aubel et al., 2001. J. Antibiot., 54: 44-55). This system, which can be applied either in high-throughput assays for detection of novel antibiotics or for analytical purposes, is based on the pristinamycin-induced protein PIP, which binds to its cognate DNA-sequence in the absence of antibiotics whereas dissociation thereof is mediated upon streptogramin-binding. A mammalian screening system was set up, in which addition of antibiotics releases the PIP-protein from its cognate DNA-sequence placed in proximity to a eukaryotic promoter. This release results in transcription of a reporter-gene, the activity of which can be measured and corresponds to the concentration of antibiotic added to the assay.

This system shows high analogy to the macrolide inducible gene regulation system (example 4). Since the macrolide-responsive gene regulation system is sensitive to all tested macrolide antibiotics (example 1), we conclude, that the MphR(A) protein recognizes the macrolide motif in general and may therefore be suited for establishment of a novel macrolide antibiotic detection system, which can be either used in high-throughput screening or for analytical purposes. Therefore we set up the following system, which can be used in three modifications:

a.) Single colony assay: This setup is well suited for high-throughput assays, it requires only one colony of a candidate strain, which is to be assayed for macrolide antibiotic production. Prior to analysis CHO-wt cells are transiently or stably transfected with the macrolide-inducible gene regulation system (plasmids pWW29 ($P_{EF1\alpha}$-MphR(A)-pA) and pWW55 ($P_{hCMV}$-ETR4-SEAP-pA), see example 4). Transfected cells are seeded into the high-throughput-suitable 96-well format. Strains to be assayed for antibiotic-production are grown for 40 hours on suitable agar plates in single colonies. For assaying, one colony is sampled with a Pasteur pipette tip (1 mm diameter) and added in one well of the transfected cells. After only 17 hours, SEAP activity is detected with a highly sensitive chemiluminescence assay (Roche Molecular Biochemicals).

b.) Transwell assay: This assay is suitable for screening of antibiotics as well as for analytical purposes for detection of antibiotics e.g. in food samples. Like in a.) CHO-wt cells are transfected with the macrolide-inducible gene regulation system and subsequently seeded into a 24-well plate. The samples (either microorganisms grown on agar or food sample after appropriate treatment (homogenization etc.)) are placed in transwell chambers (3 µm pore size, Costar 3496, Cambridge, Mass.) and applied to the CHO-cells in the 24-well plate. Macrolide antibiotics diffuse through the membrane into the cell culture medium, where SEAP-expression is induced. This setup eliminates direct contact between the sample and the cells, thus reducing possible interference leading to false-positive or false-negative results.

These two assay systems shown 3 key advantages, making them highly suitable for the detection of novel antibiotics: i.) MphR(A) is thought to recognize macrolides in general with higher sensitivity than other tests (antibiogram tests, see analogy with the streptogramin screening system, Aubel et al., 2001. J. Antibiot. 54: 44-55) ii.) This system has an inherent assay for membrane permeability of the test-compound, a prerequisite for effective antibiotic activity of macrolides, which act at intracellular targets (ribosome). iii.) The system also offers a cytotoxicity-assay: cytotoxic test compounds are likely to decrease reporter-gene activity by toxic interference with cellular components.

Despite these advantages, the requirement for mammalian cell culture makes the assay too complex for a fast detection system, which can be used at the point of care for example in field studies on farms etc. Therefore we set up an in-vitro assay procedure:

c.) The macrolide-responsive protein MphR(A) is immobilized in microtiter-plates, on beads, magnetic beads or test-strips and is bound to its cognate DNA sequence, which is labeled for easy quantification by fluorophores, dyes or reporter enzymes like alkaline phosphatase, or peroxidases. When a macrolide-containing sample is added to this complex, dissociation of MphR(A) and its cognate DNA-sequence is induced, thus separating the solid phase (microtiter plate, beads) from the labeled DNA. The readout is performed by assaying the amount of labeled DNA on the solid phase or in the sample-containing liquid phase. A decrease in labeled DNA on the solid phase therefore indicates the presence of macrolide-structures in the test sample. This assay is much faster than the cell based system (few hours), it is not dependent on complex cell culture requirements (laminar flow, incubators . . . ) and therefore well suited for analytical wherever required. However the inherent cell-toxicity and cell permeability tests of the two above set-ups are not included in this in-vitro system.

Example 7

Macrolide-responsive Expression Systems for Plant Cells

The ability to regulate transgene expression in plant cells or entire plants is an important tool for functional genomic research, repression of cloned genes which may be toxic (especially during the regeneration process) and production of protein therapeutics in plant tissue cultures (Martinez et al., 1999, Plant J. 19: 97-106). Therefore two novel plant gene regulation systems were designed.

Material and Methods

Cloning of the EpOFF and EpON Systems

The EpOFF and EpON systems are binary systems, which require a transactivator/transrepressor and a responsive target promoter. Here we describe the construction of the EpOFF system comprising the erythromycin-dependent transactivator (ET1) and the cognate plant-specific erythromycin-repressible promoters $P_{ETRp1}$ and $P_{ETRp8}$ and the EpON system which is based on plant expression constructs encoding the erythromycin-inducible protein MphR(A)/ MphR(A)-NLS and the erythromycin-inducible plant promoters $P_{ETR}pON4$ and $P_{ETR}pON8$.

Figure 9A:
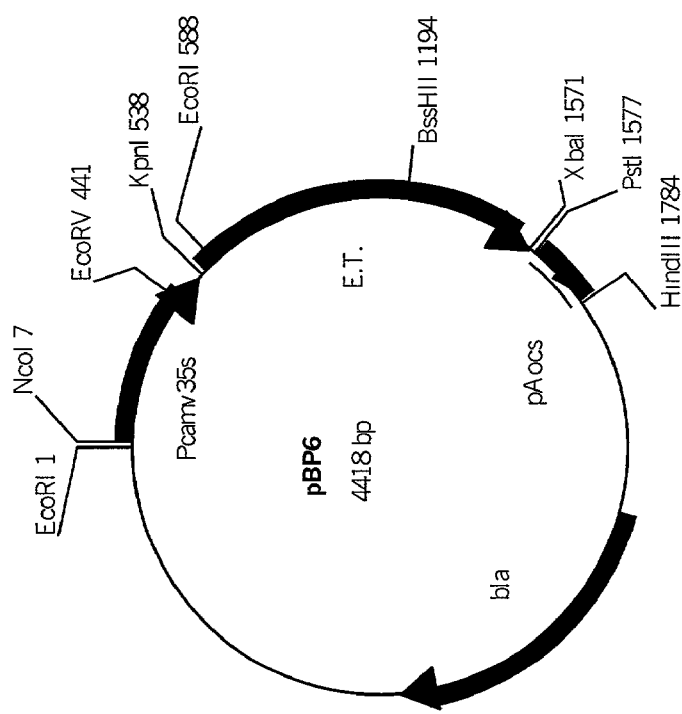
FIG. 9a: Graphical representation of the Ep$_{OFF}$ expression vector pBP6. pBP6 harbours the ET expression unit which is driven by the constitutive promoter of the cauliflower mosaic virus gene 35S($P_{CaMV35S}$) and terminated by the polyadenylation site derived from the octopine synthase gene (pA$_{ocs}$). ET is a fusion protein of the Escherichia coli Tf481A MphR(A) protein (Noguchi et al., 2000. J. Bacteriol. 182: 5052-5058) and the VP16 transactivation domain of the Herpes simplex virus.
Figure 10A:
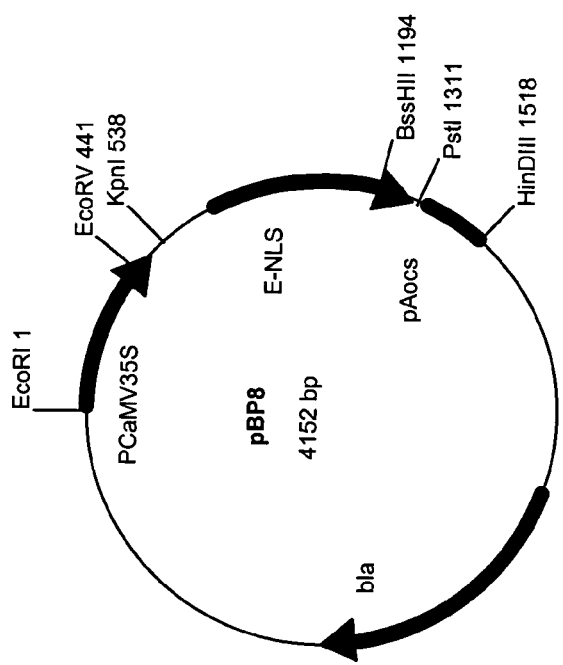
FIGS. 10a, 10b, 10c and 10d: Graphical representation of the erythromycin inducible EP$_{ON}$ plant expression vectors pBP8 (FIG. 10a), pBP9 (FIG. 10b), pBP15 (FIG. 10c) and pBP35 (FIG. 10d). pBP8 and pBP9 are MphR (A) expression vectors encoding MphR (A) alone (pBP9) or as a fusion protein to the nuclear localization signal (NLS) derived from the plant transcription factor TGA1b (pBP8). The MphR (A) or MphR(A)-NLS expression units are driven by $P_{CaMv}35s$ and terminated by the polyadenylation site derived from the octopine synthase gene ($pA_{ocs}$). The macrolide-inducible promoter comprise the ETR4 or ETR8 element containing four or eight ETR binding sites placed in 3' of $P_{CaMV}35s$ (pBP15 and pBP35, respectively) which drives the β-glucuronidase reporter-encoding expression unit which is terminated by a polyadenylation site derived from the octopine synthase gene ($pA_{ocs}$).
Figure 10B:
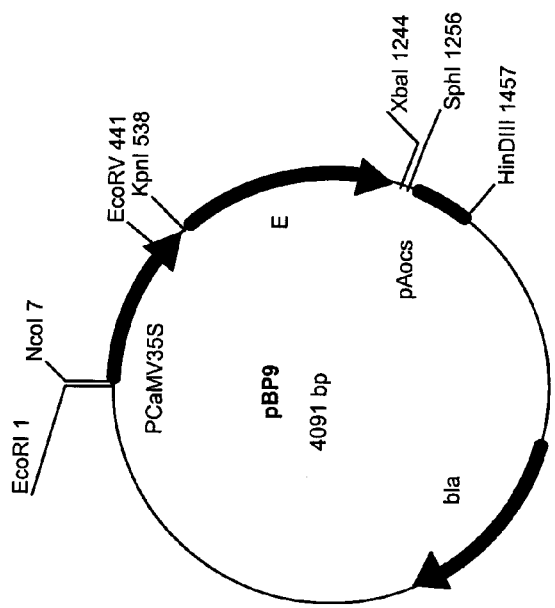
Figure 10C:
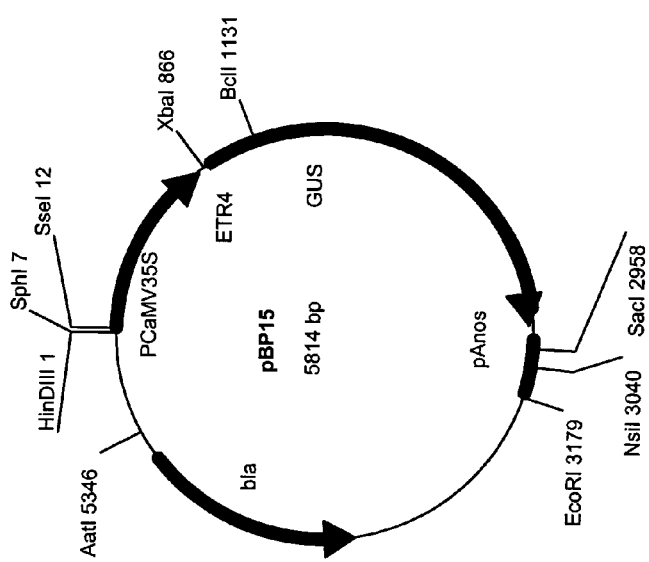
Figure 10D:
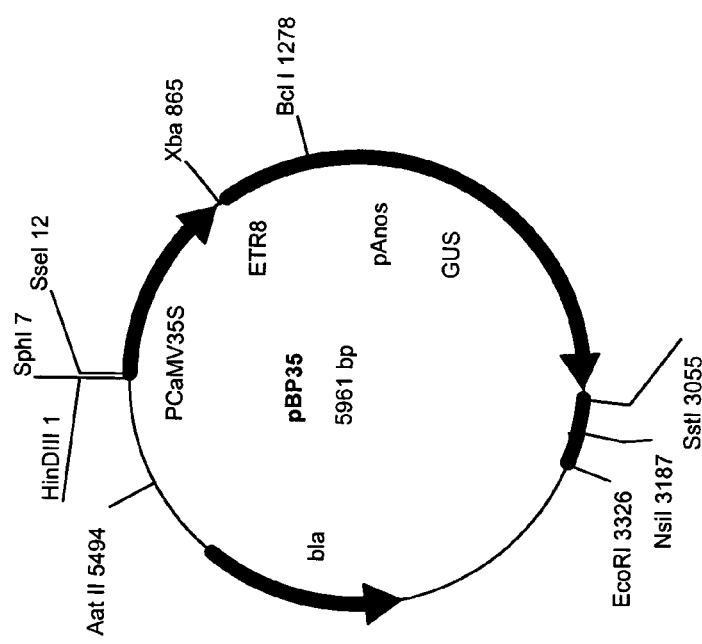

EpOFF a). ET1: Construction of a plant-specific expression configuration of ET1 (ET-VP16; SEQ ID NO:5; Example 1) was accomplished by excising MphR(A) (KpnI/BssHII) from pWW29 (example 1) and ligating it into the corresponding sites (KpnI/BssHII) of pMF276 (Disclosed in PCT application no. 00/65080) thereby replacing PIP and resulting in pBP6. The ET1-encoding expression unit encoded on pBP6 is driven by the constitutive cauliflower mosaic virus 35S promoter ($P_{CaMV35S}$; Odell et al., 1985, Nature 313: 810-812) and contains a 3' poly-adenylation signal derived from the octopine synthase gene ($pA_{ocs}$; Gatz et al., 1991, Mol. Gen. Genet 227: 229-237) (pBP6: $P_{CaMV35S}$-PIT-$pA_{ocs}$; FIG. 9a).

b). The PETRp1 promoter containing one ETR motif upstream of a TATA-box was constructed in a three-step cloning procedure:

The plant TATA-box was amplified from pTT-GUS (Bohner et al., 1999, Plant J. 19: 87-95) with oligo OBK6 (SEQ ID NO 28): gcGAATTCgattgaatataaccgacgt-gactgttacatttaggGTTAACattcgagctcggtacaactcc and oligo OBK7 (SEQ ID NO 29): TCCAAGGTtGAGCAGAAC-CTAC. OBK6 contains in its extension one ETR binding motif. The resulting PCR fragment was cloned into pEF6/V5-His TOPO (Invitrogen) in sense orientation thus resulting in pBP7. The ETR-TATA-box containing fragment was excised from pBP7 (EcoRI/XbaI) and ligated into the EcoRI/SpeI (XbaI and SpeI have compatible cohesive ends) sites of pTT-GUS resulting in pBP17. A stuffer fragment remaining from the pEF6/V5-His vector was finally eliminated by StuI restriction of pBP 17 and subsequent circularization of the vector backbone thus resulting in pBP18: ETR-TATA-GUS-$pA_{35}$S. This erythromycin repressible promoter was designated as $P_{ETRp1}$. For introduction of more ETR binding motifs the ETR8 containing fragment was excised (PmeI/EcoRI) from pWW56 (SEQ ID NO 27, example 4) and ligated into pBP18 (EcoRI/HpaI) thereby replacing the single ETR sequence and resulting in pBP36: ETR8-TATA-GUS-$pA_{35S}$. This promoter was named $P_{ETRp8}$. In these constructs the reporter gene is GUS, the *E. coli* β-glucuronidase (GUS; Vancanneyt et al., 1990, Mol. Gen. Genet. 220: 245-250), which is terminated by a poly-adenylation signal ($pA_{35S}$) derived from the cauliflower mosaic virus 35S gene (Vancanneyt et al., 1990, Mol. Gen. Genet. 220: 245-250). The TATA-box-containing minimal $P_{CaMV35}$ promoter ($P_{CaMV35Smin}$) used here, has been previously optimized for low background activity in tetracycline-responsive plant gene expression systems (positions -48/+1; Zuo and Chua, 2000, Curr. Opin. Biotechnol. 11: 146-151). In addition, $P_{CaMV35Smin}$ harbors a C to A transition at position -45 to eliminate the potential CG methylation site thought to be responsible for the silencing phenomenon associated with this promoter (Bohner et al., 1999, Plant J. 19: 87-95; Weinmann et al., 1994, Plant J. 5: 559-569).

EpON a). MphR(A)/MphR(A)-NLS: Cloning of the transrepressor MphR(A) (SEQ ID NO: 4; Example 1) into a plant cell-specific expression configuration was performed by excising the mphR(A)-containing fragment from pWW29 (example 1) (KpnI/XbaI) and subsequent ligation into the corresponding sites (KpnI/XbaI) of pMF275 (Frey et al., 2001. Biotechnol Bioeng. 74(2):154-63) thereby replacing PIP and resulting in pBP9: $P_{CaMV35S}$-mphR(A)-pA$_{ocs}$ (FIG. 10). For construction of MphR(A)-NLS, the mphR(A)-containing KpnI/BssHII fragment was excised from pWW29 (example 1) and ligated into pMF273 (Frey et al., 2001. Biotechnol Bioeng. 74(2):154-63) (KpnI/BssHII) thereby replacing PIP and resulting in pBP8 (FIG. 10): $P_{CaMV35S}$-mphR(A)-NLS-pA$_{ocs}$. The NLS sequence is described in Bohner et al., 1999, Plant J. 19: 87-95.

b). $P_{ETR}$pON4 and $P_{ETR}$pON8: The erythromycin-inducible plant gene promoter ($P_{ETR}$pON) was constructed following a two-step cloning procedure: (i) The $P_{CaMV35S}$-MCS-GUS-pA$_{nos}$ cassette which contains a polyadenylation site derived from the nopaline synthase gene (Bevan et al., 1983, Nucleic Acids Res. 11: 369-385) was excised from pBI121 (Jefferson et al., 1987, EMBO J. 6: 3901-3907) by HindIII/EcoRI and cloned into pUC18 which resulted in pMF252. (ii) pMF252 was linearized by SmaI and ligated to the ETR4 MphR(A)-binding module excised from pETR4 (PmeI/EcoRV) to result in pBP15 (FIG. 19): $P_{ETR}$pON4, $P_{CaMV35S}$-ETR4-GUS-pA$_{nos}$. For construction of $P_{ETR}$pON8 the ETR8 module was excised (PmeI/EcoRV) from pWW56 (SEQ ID NO 27, example 4) and ligated into the SmaI-site of pMF252 thus resulting in pBP35 (FIG. 10): $P_{ETR}$pON8, $P_{CaMV35S}$-ETR8-GUS-pA$_{nos}$.

Construction of the Nicotiana tabacum Cell Line SR1 and Cultivation

Callus formation was induced by placing leaf discs of in vitro-propagated Nicotiana tabacum SR1 plantlets on solidified LS (Linsmaier-Skoog) medium supplemented with sucrose (30 g/l), 2,4-dichlorophenoxyacetic acid (0.2 mg/l) and naphtalene acetic acid (0.19 mg/l). Leaf discs were incubated in the dark at 25° C. Developed callus tissue was removed from the discs and transferred to liquid media and adapted to single-cell suspension by shaking at 110 rpm.

Nicotiana tabacum suspension cultures were grown at 25° C. in the dark in Linsmeyer-Skoog (LS) medium supplemented with sucrose (30 g/l) and: Thiamine (9.9 mg/ml), Mio-Inositol (100 mg/ml), 2,4-Dichlorophenoxyacetic acid (1 mg/ml), 1-Naphtalene acetic acid (2 mg/ml) under constant rocketing at 110 rpm. All ingredients were obtained from Sigma or Duchefa (Haarlem, NL). The suspension culture was maintained by splitting every 10 days 1:10 and removing cell aggregates by filtration using a metal sieve with a pore size of 0.125 mm.

Transient Transformation of Tobacco Cells

The transformation protocol of SR1 cells was adapted from Wu and Feng (1999, Plant Cell Reports 18: 381-386). In brief, 200 mg of exponentially growing SR1 cells were harvested by centrifugation. The cells were incubated for 15 min. in 2% DMSO and washed twice in fresh medium. Cells were subsequently resuspended in electroporation buffer (5 mM CaCl$_2$; 10 mM NaCl$_2$; 0.4 M sucrose; 8.7% glycerol; 4 mM ascorbate; 10 mM HEPES; pH 6.8) and mixed with desired DNA at a concentration of 0.2 µg/µl. The cell-DNA mixture was incubated for 10 min. on ice electroporated at 700 V/cm and 980 µF using a BioRad Gene Pulser and appropriate cuvettes. Following electroporation, cells were kept on ice for 10 min. and deplasmolyzed by 4 subsequent additions of 100 µl LS medium at 5 min. intervals. Transformation rates 20%±5% are typically reached with SR1 cells using this modified protocol.

Quantification of β-Glucuronidase (GUS) Expression Levels

Transformed SR1 cells were incubated at 25° C. for 48 h while rocking at 110 rpm. During this time, GUS expression was induced (EpON) or repressed (EpOFF) by addition of 250 µg/ml of the human licensed antibiotic erythromycin. Cells were lysed in extraction buffer (50 mM NaH$_2$PO$_4$; 10 mM EDTA; 0.1% Triton X-100; 0.1% sodium lauryl sarcosine; 10 mM β-mercaptoethanol; pH 7.0) by freezing them in liquid nitrogen and grinding them using a micropestle. Soluble protein extract was collected by centrifugation for 20 min. at 15,000 rpm and 4° C. Protein concentration of plant extracts was determined using a Bradford assay (Bradford, 1976, Anal. Biochem. 72: 248-254). The GUS expression assay was performed following a modified protocol by Jefferson et al. (1987; EMBO J. 6: 3901-3907). In brief, 100 µl of cell extract were incubated in extraction buffer (see above) also containing 1 mM of the β-glucuronidase substrate 4-methylumbelliferyl glucuronide (MUG; Duchefa, NL). The reaction mixture was incubated at 37° C. and 100 µl aliquots were removed at appropriate time intervals and the reaction stopped by addition of 1.9 ml of 0.2 M K$_2$CO$_3$. The fluorescence time course was determined using typical 365 nm/455 nm excitation/emission profiles and a Shimadzu RF-5001 PC spectrofluorophotometer.

Results

Construction of an Erythromycin-repressible Gene Regulation System for Plant Cells (EpOFF)

The erythromycin-repressible plant gene expression technology (EpOFF) is based on an erythromycin-responsive plant transactivator (ET1; SEQ ID NO: 5; Example No: 1) which binds and activates chimeric plant promoters ($P_{ETRp}$) in an antibiotic-dependent manner. ET 1 comprises the E. coli MphR(A) repressor protein (SEQ ID NO: 4) fused to the VP 16 transactivation domain of Herpes simplex virus and has been successfully used for macrolide-responsive gene expression in mammalian cells. For use in plant cells, ET1 has been cloned into a plant-specific expression configuration (pBP6: $P_{CaMV35S}$-ET1-pA$_{ocs}$, FIG. 9a).

The ET1-responsive plant promoters $P_{ETRp1}$ and $P_{ETRp8}$ were constructed by fusing one ETR binding motif (pBP18, $P_{ETRp1}$) or eight tandem repetitions of ETR (ETR8, pBP36, $P_{ETRp8}$) to a TATA-box (TATATAA) element derived from $P_{CaMV35S}$ (−48/+1; Böhner et al., 1999, Plant J. 19: 87-95; Odell et al., 1985, Nature 313: 810-812). Expression vectors pBP18 and pBP36 harbor $P_{ETRp1}$-($P_{ETRp1}$-GUS-pA$_{35S}$) and $P_{ETRp8}$-($P_{ETRp8}$-GUS-pA$_{35S}$) driven GUS expression units, respectively (FIG. 9b).

Regulation Performance of the Erythromycin Repressible Plant Gene Regulation System (EpOFF) in Tobacco Suspension Cultures pBP6 ($P_{CaMV35S}$-ET1-pA$_{ocs}$, FIG. 9a) was cotransformed either with pBP 18 ($P_{ETRp1}$-GUS-pA$_{35S}$; FIG. 9b) or pBP36 ($P_{ETRp8}$-GUS-pA$_{35S}$; FIG. 9b) by electroporation into the Nicotiana tabacum cell line SR1. GUS activity was assessed after 48 hours using a fluorescence-based detection technology. Whereas in the presence of erythromycin (250 μg/ml) the erythromycin-repressible plant promoters $P_{ETRp1}$ and $P_{ETRp8}$ showed typical basal GUS expression levels (32.2±3.9 and 44.2±4.6 pmoles 4-MU min$^{-1}$ mg$^{-1}$ protein$^{-1}$, respectively) comparable with untransfected control cells (28.3±3.1 pmoles 4-MU min$^{-1}$ mg$^{-1}$ protein$^{-1}$), reporter gene expression was induced in the absence of erythromycin (90.4±10.2 and 153.7±17.8 pmoles 4-MU min$^{-1}$ mg$^{-1}$ protein$^{-1}$, respectively)

Construction of Erythromycin-Inducible Plant Gene Regulation Systems (EpON)

For regulated expression in transgenic plants and plant tissue culture an inducible rather than a repressible gene regulation system would be desirable. This enables induction of transgene repression by addition of the antibiotic rather than by its withdrawal. We therefore constructed an erythromycin-inducible plant gene regulation system (EpON) which consisted of the E. coli MphR(A) repressor protein (SEQ ID NO: 4) which binds, in the absence of macrolide antibiotics, to the ETR binding module cloned downstream of a strong constitutive plant promoter ($P_{CaMV}$35S). Binding of MphR(A) to the ETR module blocks $P_{CaMV35}$S-mediated target gene expression. In the presence of erythromycin, MphR(A) dissociates from ETR and full $P_{CaMV35}$S-driven expression is induced. For construction of EpON, MphR(A) was cloned in a plant-specific expression configuration (pBP9, $P_{CaMV35}$S-MphR(A)-pA$_{ocs}$; FIG. 10). In order to increase MphR(A) concentrations in the plant nucleus which is expected to reduce basal expression levels of the EpON system, MphR(A) was fused to a nuclear localization signal (NLS) derived from the plant transcription factor TGA1b (PEKKRARLVRNRESAQLSRQRKKLEST ) (SEQ ID NO:33); Katagiri et al., 1989, Nature 340: 727-730; Van der Krol and Chua, 1991, Plant Cell 3: 667-675) (pBP8, $P_{CaMV35S}$-MphR(A)-NLS-pA$_{ocs}$; FIG. 10).

The erythromycin-inducible plant promoters $P_{ETR}$pON4 (pBP15) and $P_{ETR}$pON8 (pBP35) were constructed by cloning four and eight copies of the ETR element (SEQ ID NO: 26, 27) downstream of the $P_{CaMV35S}$ promoter, respectively (FIG. 10). Expression vectors pBP15 and pBP35 contain $P_{ETR}$pON4 ($P_{CaMV35S}$-ETR4-GUS-pA$_{nos}$) and $P_{ETR}$pON8 ($P_{CaMV35S}$-ETR8-GUS-pA$_{nos}$) driven GUS expression units (FIG. 10). Both plasmids show expression levels similar to the isogenic construct pMF252 ($P_{CaMV35S}$-MCS-PA$_{nos}$) in the absence of a MphR(A)-encoding construct or in the presence of erythromycin (see below).

Regulation Performance of the EpON System in Tobacco Suspension Cultures

The EpON system was introduced into SR1 tobacco suspension cultures by cotransformation of various combinations of transrepressor-encoding plasmids pBP8 ($P_{CaMV35S}$-MphR(A)-NLS-pA$_{ocs}$) or pBP9 ($P_{CaMV35S}$-MPhR(A)-pA$_{ocs}$) and $P_{ETR}$-pON-driven reporter constructs pBP15 ($P_{ETR}$pON4: $P_{CaMV35S}$-ETR4-GUS-pA$_{nos}$) or pBP35 ($P_{ETR}$pON8: $P_{CaMV35S}$-$P_{ETR8}$-GUS-pA$_{nos}$). In all EpON configurations tested (pBP8/pBP15; pBP8/pBP35; pBP9/pBP15; pBP9/pBP35) the strong constitutive viral promoter $P_{CaMV35S}$ was strongly repressed in the absence of erythromycin (pBP8/pBP15: 41.4±4.2; pBP8/pBP35: 36.4±3.9; pBP9/pBP15: 40.2±5.3; pBP9/pBP35: 34.3±4.8 pmoles 4-MU min$^{-1}$ mg$^{-1}$ protein$^{-1}$). However, upon addition of 250 μg/ml erythromycin to the cell culture medium the MphR(A)-based transrepressors are released from the ETR module as shown in mammalian cells. Addition of the macrolide antibiotic erythromycin to the plant tissue culture resulted in induction of GUS activity and maximum expression levels comparable to $P_{CaMV35S}$-driven expression (pBP8/pBP15: 313.5±39.6; pBP8/pBP35: 283.6±24.7; pBP9/pBP15: 305.2±24.9; pBP9/pBP35: 276.7±34.1; pMF252 ($P_{CaMV35S}$-GUS-pA$_{nos}$): 329.3±41.9 pmoles 4-MU min$^{-1}$ mg$^{-1}$ protein$^{-1}$). Fusion of MphR(A) to a NLS (pBP8) neither increased the overall regulation performance of the EpON systems nor reduced their basal expression levels.

Discussion

We have established an alternative antibiotic-inducible gene regulation technology by adapting determinants of an E. coli macrolide antibiotic resistance operon for use in plant cells. Ideal plant and mammalian cell-specific gene regulation systems share several characteristics. For example, they should show high induction ratios (low basal expression levels and high expression levels upon induction), rapid kinetics (fast induction and repression), and no pleiotropic effects or cytotoxicity.

Transgenic plants grown in contained greenhouses and plant tissue culture (mainly tobacco suspension culture) become increasingly important for the production of protein pharmaceuticals such as human interleukin (IL)-2 and IL-4 (Magnuson et al., 1998, Protein Expr. Purif. 13: 45-52), various therapeutic antibodies (Ma et al., 1998; Nature Med. 4: 601-606) or edible human vaccines (Tacket et al., 1998; Nature Med. 4: 607-609). This is due to the simple and inexpensive cultivation technology and the absence of contaminating animal viruses, bloodborne pathogens, oncogenes and bacterial toxins. In this context, plant gene regulation systems may be essential for safe production of difficult-to-express proteins and agriculture-based large-scale expression of desired proteins in a particular developmental stage.

We have demonstrated here the successful use of novel plant gene regulation systems, which are based on an E. coli macrolide antibiotic resistance operon. The erythromycin-responsive plant expression technology offers an attractive alternative to existing gene regulation technologies for challenging applications in basic plant research, agricultural applications and biopharmaceutical manufacturing.

Example 8

Retroviral Expression Vectors Containing Macrolide-dependent Transactivators

Successful gene therapy requires reliable delivery of therapeutic transgenes into a variety of human cell types. Replication-incompetent retroviruses are ideal vectors since they mediate DNA transfer, single-copy chromosomal integrations and expression of therapeutic transgenes in target cell lines (Ausubel et al. 1995, Current Protocols in Molecular Biology (John Wiley &Sons, NY). In combination with pantropic packaging systems (Yee et al., 1994, Methods Cell Biol. 43: 99-112; Bums et al., 1993; Proc. Natl. Acad. Sci. USA 90: 8033-8037) retroviruses can be produced which infect a wide variety of cell types.

We have constructed lentiviral vectors based on those developed by Reiser et al. (1996. Proc. Natl. Acad. Sci USA 93: 15266-15271), Reiser et al. (2000. J. Virol. 74: 10589-

10599), Mochizuki et al. (1998. J. Virol. 72: 8873-8883) which can deliver the macrolide-dependent transactivator to a variety of mammalian cell lines.

Figure 11:
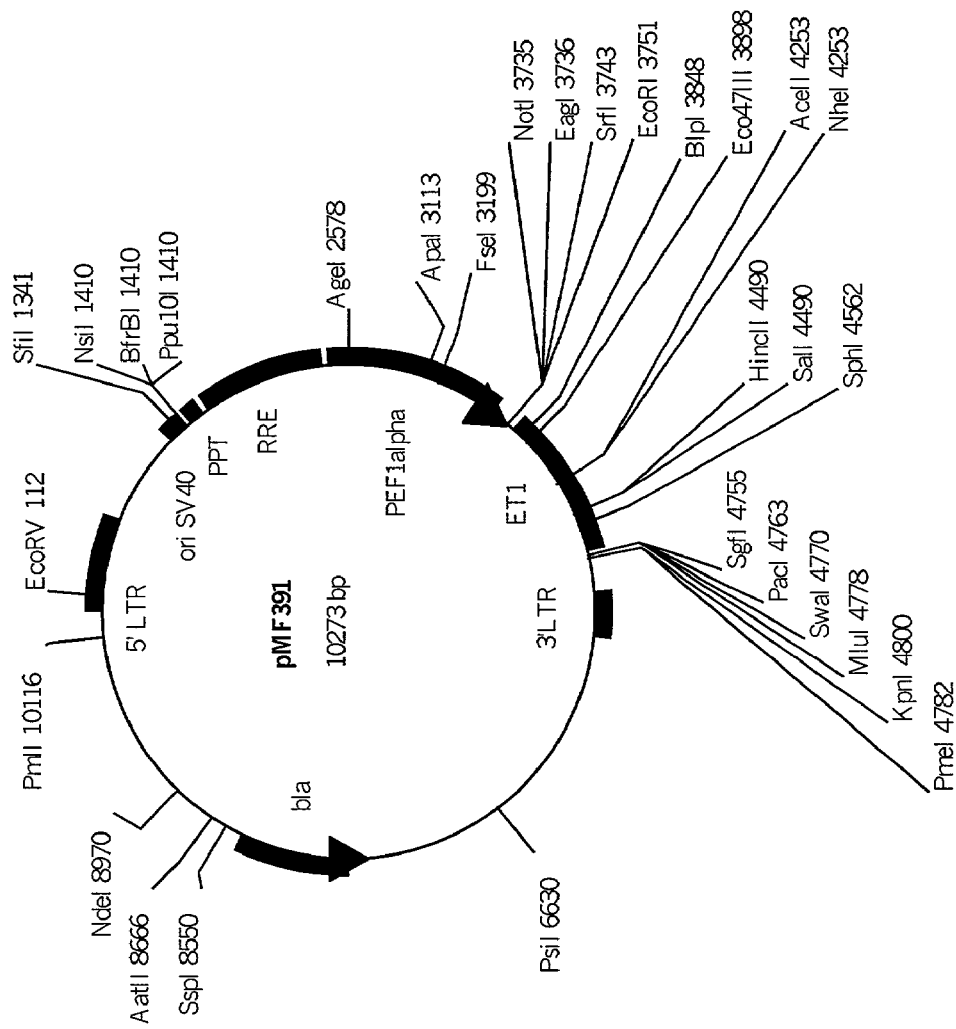
FIG. 11: Graphical representation of the lentiviral vector pMF391 encoding the macrolide-repressible transactivator ET1 under control of the human elongation factor 1α promoter ($P_{EF1\alpha}$). The vector contains the following elements: 5'LTR-Ψ⁺-RRE-$P_{EF1\alpha}$-ET1-3'LTR$_{AU3}$: 5'LTR: 5'long terminal repeat, Ψ⁺ packaging signal, RRE: nuclear RNA export signal, 3'LTR$_{AU3}$: 3' long terminal repeat containing a deletion in the U3 region (self-inactivating phenotype).

The macrolide-responsive transactivator ET1 (MphR(A)-VP16, see example 1) was cloned into a lentiviral vector: ET1 was excised (EcoRI/XbaI) from pWW35 and cloned (EcoRI/SpeI) into pMF359 thus resulting in ET1 under control of the human elongation factor 1α promoter ($P_{EF1\alpha}$). The corresponding lentiviral vector pMF391 (FIG. 11) contains the following elements: 5'LTR-Ψ⁺-RRE-$P_{EF1\alpha}$-ET1-3'LTR$_{\Delta U3}$: 5'LTR: 5'long ter Ψ⁺ packaging signal, RRE: nuclear RNA export signal, 3'LTR$_{\Delta U3}$: 3' long terminal repeat containing a deletion in the U3 region (self-inactivating phenotype).

For production of replication-incompetent, self-inactivating lentiviruses a mixture containing 94 µl DMEM, 6 µl FUGENE (Roche Diagnostics AG, Rotkreuz, Switzerland), 25 mM chloroquine, 1.5 µg pLTR-G (encoding the pseudotyping envelope protein VSV-G of the vesicular stomatitis virus; Reiser et al., 1996. Proc. Natl. Acad. Sci. USA 93, 15266-15271), 1.5 µg of the helper construct pCD/NL-BH* (Mochizicki et al., 1998. J. Virol. 72: 8873-8883) and 1.5 µg of the ET1-encoding lentiviral expression vector pMF391 was transfected into human embryonic kidney cells (HEK293-T). The medium was replaced after 24 hours and virus particles were produced for another 48 h. Viral particles were collected from the HEK293-T supernatant by filtration through a 0.45 µm filter (Schleicher & Schuell GmbH, Dassel, Germany: FP030/2) yielding typical titers of $2 \times 10^7$ viral particles per ml.

For functional analysis 100'000 CHO cells per 6-well were infected with 200 µl viral supernatant also containing 8 µg/ml polybrene (hexadimethrine bromide; Sigma Chemie, Buchs, Switzerland). These cells were subsequently cotransfected with pWW44 (see example 1) encoding the cyan fluorescent protein under control of the macrolide-responsive promoter $P_{ETR3}$. In the absence of erythromycin, cells showed bright cyan fluorescence whereas addition of 2 µg/ml erythromycin resulted in complete repression of CFP expression.

Example 9

Macrolide-responsive Gene Expression in Transgenic Mice

In order to demonstrate the potential of macrolide-responsive expression technology in vivo, we produced transgenic mice. The expression units $P_{EF1-\alpha}$-ET1-pA and $P_{ETR3}$-CFP-pA were excised from pWW83 (a pWW35 derivative: The human EF1α (elongation factor 1α) promoter ($P_{EF1-\alpha}$) was excised from pEF4/Myc-His A (Invitrogen) with SspI/EcoRI and cloned SspI/EcoRI into pWW35 thereby replacing $P_{SV40}$) and pWW44, respectively and independently injected into mouse oocytes. These oocytes were reimplanted into separate pseudo-pregnant foster mice. Offspring were screened by PCR for $P_{EF1-\alpha}$-ET1-pA- and $P_{ETR3}$-CFP-pA-containing offsprings (Hogan et al., 1994, Manipulating the mouse embryo, 2nd edition, Cold Spring Harbor Laboratory Press, Cold Spring Harbor, N.Y.). Positive offsprings were crossed to generate double transgenic mice which contain the $P_{EF1-\alpha}$-ET1-pA as well as the $P_{ETR3}$-CFP-pA expression units. Vibratome sections of different organs of positive double transgenic offsprings were analyzed by CFP-mediated fluorescence. Double transgenic mice containing $P_{EF1-\alpha}$-ET1-pA and $P_{ETR3}$-CFP-pA expression units showed no CFP-mediated fluorescence in different organs (including muscle and brain) when macrolides were supplemented in the drinking water. However, when these mice were watered with macrolide-free drinking water, high level CFP expression could be observed.

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims. All references cited herein are incorporated by reference.

What is claimed is:

1. An isolated mammalian cell comprising a nucleic acid, the nucleic acid comprising an erythromycin-responsive ("ETR") operator sequence from an *Eseherichia coli* erythromycin-regulatable promoter operatively linked to a first eukaryotic promoter, wherein an *Escherichia coli* MphR(A) polypeptide binds to the ETR operator sequence in the absence of a cognate antibiotic, and the binding between the MphR(A) polypeptide and the ETR operator sequence is disrupted when the cognate antibiotic is present.

2. The mammalian cell of claim 1 further comprising a nucleic acid that encodes the *Escherichia coli* MphR(A) polypeptide.

3. The mammalian cell of claim 2, wherein the *Escherichia coli* MphR(A) polypeptide has the amino acid sequence SEQ ID NO: 32.

4. The mammalian cell of claim 2, wherein the *Escherichia coli* MphR(A) polypeptide is encoded by SEQ ID NO: 4.

5. The mammalian cell of claim 2, wherein the *Escherichia coli* MphR(A) polypeptide further comprises an operably linked second or third polypeptide capable of activating transcription in eukaryotic cells.

6. The mammalian cell of claim 5, wherein the second or third polypeptide capable of activating transcription is selected from the group consisting of a VP16 activating domain, a GAL4 activating domain, a CTF/NF1 activating domain, an AP2 activating domain, an ITF1 activating domain, an ITF2 activating domain, an Oct1 activating domain, a Sp1 activating domain, an E2F4 activating domain, and a p65 domain of NF-κB.

7. The mammalian cell of claim 2, wherein the first eukaryotic promoter is operatively linked to a first coding sequence.

8. The mammalian cell of claim 7, wherein the nucleic acid comprising the ETR operator sequence further comprises a second or third eukaryotic promoter.

9. The mammalian cell of claim 8, wherein the nucleic acid comprising the ETR operator sequence further comprises a tetracycline-regulated or a pristinamycin-regulated operator sequence operatively linked to the second or third eukaryotic promoter.

10. The mammalian cell of claim 8, wherein the second or third eukaryotic promoter is operatively linked to a second or third coding sequence.

11. The mammalian cell of claim 10, wherein the first, second or third coding sequence contains an internal ribosome entry site (IRES).

12. The mammalian cell of claim 10, wherein the first, second or third coding sequence encodes the *Escherichia coli* MphR(A) polypeptide.

13. The mammalian cell of claim 12, wherein the *Escherichia coli* MphR(A) polypeptide is encoded by SEQ ID NO: 4.

14. A method for regulating expression of an ETR-linked gene in the mammalian cell of claim 2, comprising modulating the concentration of the cognate antibiotic that contacts the cell, thereby regulating expression of the gene.

15. The method of claim 14, wherein the *Escherichia coli* MphR(A) polypeptide further comprises an operably linked second or third polypeptide capable of activating transcription in eukaryotic cells.

16. The method of claim 15, wherein the second or third polypeptide capable of activating transcription is selected from the group consisting of a VP16 activating domain, a GAL4 activating domain, a CTF/NF1 activating domain, an AP2 activating domain, an ITF1 activating domain, an ITF2 activating domain, an Oct1 activating domain, a Sp1 activating domain, an E2F4 activating domain, and a p65 domain of NF-κB.

17. A process for producing a protein comprising:
a) culturing the mammalian cell of claim 7, wherein the first coding sequence encodes the protein, and
b) modulating the concentration of the cognate antibiotic that contacts the cell thereby regulating expression of the ETR-linked gene.

18. The process of claim 17, further comprising the step of collecting the protein produced by the cell.

19. The process of claim 18, wherein the *Escherichia coli* MphR(A) polypeptide is operably linked to a polypeptide capable of activating transcription in eukaryotic cells.

20. The method of claim 14, wherein the cognate antibiotic is erythromycin, clarithromycin, azithromycin, tylosin, or roxithromycin.

21. The process of claim 17, wherein the cognate antibiotic is erythromycin, clarithromycin, azithromycin, tylosin, or roxithromycin.

22. An isolated mammalian cell comprising a nucleic acid, the nucleic acid comprising an erythromycin-responsive ("ETR") operator sequence operatively linked to a first eukaryotic promoter, wherein the ETR operator sequence comprises the sequence GATTGAATATAACCGACGTGACTGTTACATTTAGG (SEQ ID NO: 31).

23. The mammalian cell of claim 22 that further comprises a nucleic acid that encodes an *Escherichia coli* MphR(A) polypeptide.

24. The mammalian cell of claim 23, wherein the first eukaryotic promoter is operatively linked to a first coding sequence.

25. The mammalian cell of claim 24, wherein the nucleic acid comprising an ETR operator sequence further comprises a second or third eukaryotic promoter.

26. The mammalian cell of claim 25, wherein the nucleic acid comprising the ETR operator sequence further comprises a tetracycline-regulated or a pristinamycin-regulated operator sequence operatively linked to the second or third eukaryotic promoter.

27. The mammalian cell of claim 25, wherein the second or third eukaryotic promoter is operatively linked to a second or third coding sequence.

28. The mammalian cell of claim 27, wherein the first, second or third coding sequence contains an internal ribosome entry site (IRES).

29. The mammalian cell of claim 27, wherein the first, second or third coding sequence encodes the *Escherichia coli* MphR(A) polypeptide.

30. The mammalian cell of claim 29, wherein the *Eseherichia coli* MphR(A) polypeptide is encoded by SEQ ID NO: 4.

31. The mammalian cell of claim 23, wherein the *Escherichia coli* MphR(A) polypeptide has the amino acid sequence SEQ ID NO: 32.

32. The mammalian cell of claim 23, wherein the *Escherichia coli* MphR(A) polypeptide is encoded by SEQ ID NO: 4.

33. The mammalian cell of claim 23, wherein the *Escherichia coli* MphR(A) polypeptide further comprises an operably linked second or third polypeptide capable of activating transcription in eukaryotic cells.

34. The mammalian cell of claim 33, wherein the second or third polypeptide capable of activating transcription is selected from the group consisting of a VP16 activating domain, a GAL4 activating domain, a CTF/NF1 activating domain, an AP2 activating domain, an ITF1 activating domain, an ITF2 activating domain, an Oct1 activating domain, a Sp1 activating domain, an E2F4 activating domain, and a p65 domain of NF-κB.

35. A method for regulating expression of an ETR-linked gene in the mammalian cell of claim 23, comprising modulating the concentration of a cognate antibiotic that contacts the cell, wherein the cognate antibiotic binds to the *Escherichia coli* MphR(A) polypeptide, thereby regulating expression of the gene.

36. The method of claim 35, wherein the *Escherichia coli*MphR(A) polypeptide further comprises an operably linked second or third polypeptide capable of activating transcription in eukaryotic cells.

37. The method of claim 36, wherein the second or third polypeptide capable of activating transcription is selected from the group consisting of a VP16 activating domain, a GAL4 activating domain, a CTF/NF1 activating domain, an AP2 activating domain, an ITF1 activating domain, an ITF2 activating domain, an Oct1 activating domain, a Sp1 activating domain, an E2F4 activating domain, and a p65 domain of NF-κB.

38. The method of claim 35, wherein the cognate antibiotic is erythromycin, clarithromycin, azithromycin, tylosin, or roxithromycin.

39. A process for producing a protein comprising:
a) culturing the mammalian cell of claim 24, wherein the first coding sequence encodes the protein, and
b) modulating the concentration of a cognate antibiotic that contacts the cell thereby regulating expression of the ETR-linked gene, wherein the cognate antibiotic binds to the *Escherichia coli* MphR(A) polypeptide.

40. The process of claim 39, further comprising the step of collecting the protein produced by the cell.

41. The process of claim 40, wherein the *Eseherichia coli* MphR(A) polypeptide is operably linked to a polypeptide capable of activating transcription in eukaryotic cells.

42. The process of claim 39, wherein the cognate antibiotic is erythromycin, clarithromycin, azithromycin, tylosin, or roxithromycin.

* * * * *